United States Patent
Xu et al.

(10) Patent No.: US 6,465,611 B1
(45) Date of Patent: Oct. 15, 2002

(54) COMPOUNDS FOR IMMUNOTHERAPY OF PROSTATE CANCER AND METHODS FOR THEIR USE

(75) Inventors: Jiangchun Xu, Bellevue, WA (US); Davin C. Dillon, Redmond, WA (US); Jennifer Lynn Mitcham, Redmond, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/232,149

(22) Filed: Jan. 15, 1999

Related U.S. Application Data

(63) Continuation-in-part of application No. 09/159,812, filed on Sep. 23, 1998, which is a continuation-in-part of application No. 09/115,453, filed on Jul. 14, 1998, which is a continuation-in-part of application No. 09/030,607, filed on Feb. 25, 1998, now Pat. No. 6,262,245, which is a continuation-in-part of application No. 09/020,956, filed on Feb. 9, 1998, now Pat. No. 6,261,562, which is a continuation-in-part of application No. 08/904,804, filed on Aug. 1, 1997, now abandoned, which is a continuation-in-part of application No. 08/806,099, filed on Feb. 25, 1997, now abandoned.

(51) Int. Cl.[7] .......................... A61K 38/00; C07K 1/00; A01N 37/18
(52) U.S. Cl. .............................. 530/300; 530/350; 514/2
(58) Field of Search ................................. 530/300, 350; 435/69.1

(56) References Cited

U.S. PATENT DOCUMENTS 5,786,148 A  7/1998  Bandman et al. ............... 435/6

FOREIGN PATENT DOCUMENTS

| WO | WO 98/37039 |   | 8/1998 |
| WO | WO 98/37093 | * | 8/1998 |
| WO | WO 00/04149 |   | 1/2000 |
| WO | WO 01/25272 |   | 4/2001 |
| WO | WO 01/34802 |   | 5/2001 |
| WO | WO 01/51633 |   | 7/2001 |

OTHER PUBLICATIONS

Bandman et al. (Geneseq Database entry, Accerssion No. AC W60592, Sep. 7, 1998).*
GenBank Accession No. AF047020, Feb. 1, 1999.
Schmidt–Wolf et al., "Activated T cells and cytokine–induced CD3+ CD56+ killer cells," *Annals of Hematology* 74:51–56, 1997.
Hara et al., "Characterization of cell phenotype by a novel cDNA library subtraction system: expression of CD8α in a mast cell–derived interleukin–4–dependent cell line," *Blood* 84(1): 189–199, Jul. 1, 1994.
Lalvani et al., "Rapid effector function in CD8+ memory cells," *J. Exp. Med.* 186(6): 859–865, Sep. 15, 1997.
Nelson et al., Genbank Accession No. NP_004908, Mar. 18, 2000.
Sherman et al., "Selecting T cell receptors with high affinity for self–MHC by decreasing the contribution of CD8," *Science* 258(5083): 815–818, Oct. 30, 1992.
Theobald, et al., "Targeting p53 as a general tumor antigen," *Proc. Natl. Sci. USA* 92(25): 11993–11997, Dec. 5, 1995.
Van Tsai et al., "In vitro immunization and expansion of antigen–specific cytotoxic T lymphocytes for adoptive immunotherapy using peptide–pulsed dendritic cells," *Critical Reviews in Immunology* 18:65–75, 1998.
Vasmatzis et al., "Discovery of three genes specifically expressed in human prostate by expressed sequence tag database analysis," *Proc. Natl. Acad. Sci. USA* 95(1):300–304, Jan. 6, 1998.

* cited by examiner

Primary Examiner—Kenneth R. Horlick
Assistant Examiner—Young Kim
(74) *Attorney, Agent, or Firm*—SEED Law Group PLLC

(57) ABSTRACT

Compounds and methods for treating prostate cancer are provided. The inventive compounds include polypeptides containing at least a portion of a prostate tumor protein. Vaccines and pharmaceutical compositions for immunotherapy of prostate cancer comprising such polypeptides, or DNA molecules encoding such polypeptides, are also provided, together with DNA molecules for preparing the inventive polypeptides.

6 Claims, 4 Drawing Sheets

US 6,465,611 B1

COMPOUNDS FOR IMMUNOTHERAPY OF PROSTATE CANCER AND METHODS FOR THEIR USE

CROSS REFERENCE TO RELATED APPLICATIONS

This application is a continuation-in-part of U.S. patent application Ser. No. 09/159,812, filed Sep. 23, 1998, which is a continuation-in-part of U.S. patent application Ser. No. 09/115,453, filed Jul. 14, 1998, which is a continuation-in-part of U.S. patent application Ser. No. 09/030,607, filed Feb. 25, 1998, U.S. Pat. No. 6,262,245 which is a continuation-in-part of U.S. patent application Ser. No. 09/020,956, filed Feb. 9, 1998 U.S. Pat. No. 6,261,562, which is a continuation-in-part of U.S. patent application Ser. No. 08/904,804, filed Aug. 1, 1997 abandoned, which is a continuation-in-part of U.S. patent application Ser. No. 08/806,099, filed Feb. 25, 1997 abandoned.

TECHNICAL FIELD

The present invention relates generally to compositions and methods for the treatment of prostate cancer. The invention is more particularly related to polypeptides comprising at least a portion of a prostate tumor protein and to polynucleotide molecules encoding such polypeptides. Such polypeptides may be used in vaccines and pharmaceutical compositions for treatment of prostate cancer.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved vaccines and treatment methods for prostate cancer. The present invention fulfills these needs and further provides other related advantages.

SUMMARY OF THE INVENTION

The present invention provides compounds and methods for immunotherapy of prostate cancer. In one aspect, isolated polypeptides are provided comprising at least an immunogenic portion of a prostate tumor protein or a variant thereof that differs only in one or more substitutions, deletions, additions and/or insertions, such that the ability of the variant to react with protein-specific antisera is not substantially diminished. Within certain embodiments, the prostate tumor protein comprises an amino acid sequence encoded by a polynucleotide sequence selected from the group consisting of SEQ ID NO: 2, 3, 8–29, 41–45, 47–52, 54–65, 70, 73–74, 79, 81, 87,90,92,93,97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 25 332, and 334, and complements of such polynucleotides.

In related aspects, isolated polynucleotides encoding the above polypeptides or portions thereof are provided. In specific embodiments, such polynucleotides may comprise a sequence provided in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 332, or 334. The present invention further provides expression vectors comprising the above polynucleotides and host cells transformed or transfected with such expression vectors. In preferred embodiments, the host cells are selected from the group consisting of *E. coli*, yeast and mammalian cells.

In another aspect, the present invention provides fusion proteins comprising at least one polypeptide as described above, in combination with a second polypeptide as described above and/or a known prostate tumor antigen. Polynucleotides encoding such fusion proteins are further provided.

The present invention also provides pharmaceutical compositions comprising one or more of the above polypeptides, or a polynucleotide molecule encoding such polypeptides, and a physiologically acceptable carrier, together with vaccines comprising one or more of such polypeptide or polynucleotide molecules in combination with a non-specific immune response enhancer.

Within other aspects, the present invention provides pharmaceutical compositions comprising (a) an antibody that specifically binds to a prostate tumor protein that comprises an amino acid sequence that is encoded by a polynucleotide sequence selected from the group consisting of (i) nucleotide sequences recited in any one of SEQ ID NOS: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 332, or 334; and (ii) complements of the foregoing polynucleotide sequences; and (b) a physiologically acceptable carrier. Vaccines are also provided, comprising one or more such antibodies in combination with a non-specific immune response enhancer.

Within other aspects, the present invention provides pharmaceutical compositions comprising (a) a T cell that specifically reacts with a prostate tumor protein that comprises an amino acid sequence that is encoded by a polynucleotide sequence selected from the group consisting of (i) nucleotide sequences recited in any one of SEQ ID NOS: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 332, or 334 ; and (ii) complements of the foregoing polynucleotide sequences; and (b) a physiologically acceptable carrier. Vaccines are also provided, comprising one or more such T cells in combination with a non-specific immune response enhancer.

In yet a further aspect, methods for the treatment of prostate cancer in a patient are provided, the methods comprising obtaining PBMC from the patient, incubating the PBMC with a polypeptide of the present invention (or a polynucleotide that encodes such a polypeptide) to provide incubated T cells and administering the incubated T cells to the patient. The present invention additionally provides methods for the treatment of prostate cancer that comprise incubating antigen presenting cells with a polypeptide of the present invention (or a polynucleotide that encodes such a polypeptide) to provide incubated antigen presenting cells and administering the incubated antigen presenting cells to the patient. In certain embodiments, the antigen presenting cells are selected from the group consisting of dendritic cells and macrophages. Compositions for the treatment of prostate cancer comprising T cells or antigen presenting cells that have been incubated with a polypeptide or polynucleotide of the present invention are also provided.

In yet another aspect, methods are provided for inhibiting the development of prostate cancer in a patient, comprising administering an effective amount of at least one of the above pharmaceutical compositions and/or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

In FIG. 2A, data is presented for fibroblasts pulsed with the P2S-12 peptide, as compared to fibroblasts pulsed with a control E75 peptide. In FIG. 2B, data is presented for fibroblasts expressing P506, as compared to fibroblasts expressing HER-2/neu.

DETAILED DESCRIPTION OF THE INVENTION

Figure 1:
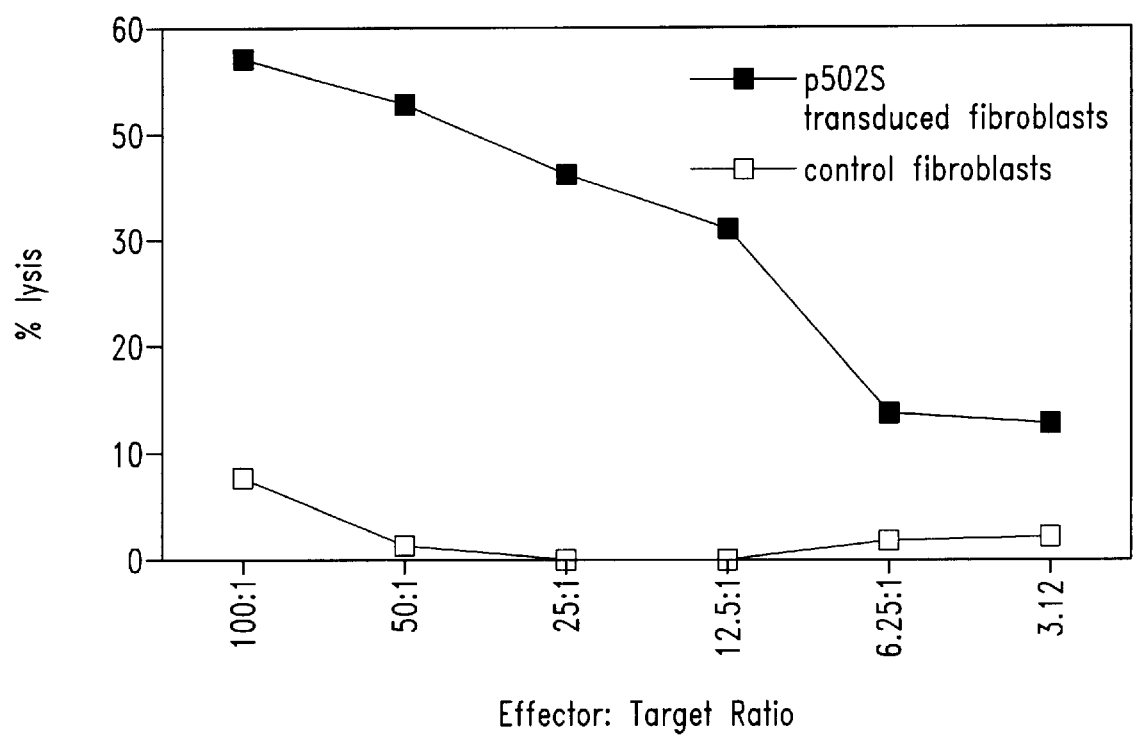
FIG. 1 is a graph illustrating the ability of T cells to kill fibroblasts expressing the representative prostate tumor polypeptide P502S, as compared to control fibroblasts. The % lysis is shown at a series of effector:target ratios, as indicated.

As noted above, the present invention is generally directed to compositions and methods for the therapy of cancer, such as prostate cancer. The compositions described herein may include one or more prostate tumor polypeptides, nucleic acid sequences encoding such polypeptides, binding agents such as antibodies that bind to a polypeptide and/or immune system cells (e.g., T cells). Prostate tumor polypeptides of the present invention generally comprise at least a portion of a prostate tumor protein or a variant thereof, such that the therapeutic, antigenic and/or immunogenic properties of the polypeptide are not substantially diminished relative to the native prostate tumor protein. A "prostate tumor protein" is a protein that is overexpressed (i.e., mRNA and/or protein is present at a level that is at least two fold higher) in prostate tumor tissue, relative to normal prostate tissue and/or relative to other tissues (e.g., brain, heart, kidney, liver, lung, pancreas, ovary, placenta, skeletal muscle, spleen and/or thymus). Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a polypeptide as described above. T cells that may be employed within such compositions are generally T cells that are specific for a polypeptide as described above.

The present invention is based on the discovery of previously unknown human prostate tumor proteins. Partial sequences of polynucleotides encoding specific prostate tumor proteins (or complementary to such coding sequences) are provided in SEQ ID NOs:2, 3, 8–29, 41–45, 47–52, 54–65, 70, 73–74, 79, 81, 87, 90, 92, 93, 97, 103, 104, 107, 109–111, 115–160, 181, 188, 191, 193, 194, 198, 203, 204, 207–228, 229–305, 307–315, 326, 328, 330, 332, and 334.

Prostate Tumor Polynucleotides

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

Any polynucleotide that encodes a prostate tumor protein or a portion or other variant thereof as described herein is encompassed by the present invention. Preferred polynucleotides comprise at least 10 consecutive nucleotides, and preferably at least 30 consecutive nucleotides, that encode a portion of a prostate tumor protein. More preferably, a polynucleotide encodes an immunogenic portion of a prostate tumor protein. Polynucleotides complementary to any such sequences are also encompassed by the present invention.

Polynucleotides may comprise a native sequence (i e., an endogenous sequence that encodes a prostate tumor protein or a portion thereof) or may comprise a variant of such a sequence. Polynucleotide variants may contain one or more substitutions, additions, deletions and/or insertions such that the therapeutic, antigenic and/or immunogenic properties are not substantially diminished, relative to a native prostate tumor protein. Such modifications may be readily introduced using standard mutagenesis techniques, such as oligonucleotide-directed site-specific mutagenesis as taught, for example, by Adelman et al. (*DNA*, 2:183, 1983). Preferably, the antigenicity or immunogenicity of a polypeptide variant is not substantially diminished. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native prostate tumor protein or a portion thereof. The percent identity may be readily determined by comparing sequences using computer algorithms well known to those of ordinary skill in the art, such as Megalign, using default parameters. Certain variants are substantially homologous to a native gene, or a portion or complement thereof. Such polynucleotide variants are capable of hybridizing under moderately stringent conditions to a naturally occurring DNA sequence encoding a native prostate tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, more preferably 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees Mol. *Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) Rapid similarity searches of nucleic acid and protein data banks *Proc. Natl. Acad., Sci.* USA 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence.

Polynucleotides may be prepared using any of a variety of techniques. For example, a polynucleotide may be identified, as described in more detail below, using a PCR-based subtraction protocol. Alternatively, polypeptides may be amplified via polymerase chain reaction (PCR) from cDNA prepared from prostate tumor cells. For this approach, sequence-specific primers may be designed based on the sequences provided herein, and may be purchased or synthesized.

An amplified portion may be used to isolate a full length gene from a suitable library (e.g., a prostate tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987; Erlich ed., *PCR Technology*, Stockton Press, NY, 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nuci. Acids. Res.* 19:3055–60, 1991). Transcription-Mediated Amplification, or TMA is another method that may be utilized for the amplification of DNA, rRNA, or mRNA, as described in Patent No. PCT/US91/03184. This autocatalytic and isothermic non-PCR based method utilizes two primers and two enzymes: RNA polymerase and reverse transcriptase. One primer contains a promoter sequence for RNA polymerase. In the first amplification, the promoter-primer hybridizes to the target rRNA at a defined site. Reverse transcriptase creates a DNA copy of the target rRNA by extension from the 3' end of the promoter-primer. The RNA in the resulting complex is degraded and a second primer binds to the DNA copy. A new strand of DNA is synthesized from the end of the primer by reverse transcriptase creating double stranded DNA. RNA polymerase recognizes the promoter sequence in the DNA template and initiates transcription. Each of the newly synthesized RNA amplicons re-enters the TMA process and serves as a template for a new round of replication leading to the expotential expansion of the RNA amplicon. Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of prostate tumor proteins are provided in SEQ ID NOS: 1–107, 109–111, 115–171, 173–175, 177, 179–228, 229–305, 307–326, 328, 330, and 332–335. The polynucleotides recited herein, as well as full length polynucleotides comprising such sequences, other portions of such full length polynucleotides, and sequences complementary to all or a portion of such full length molecules, are specifically encompassed by the present invention.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a prostate tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a prostate tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g, promoter, enhancer or transcription initiation site), and block transcription of the gene; or to block translation by inhibiting binding of a transcript to ribosomes.

A portion of a coding sequence or a complementary sequence may also be designed as a probe or primer to detect gene expression. Probes may be labeled by a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length. Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g, avian pox virus). Techniques for incorporating polynucleotides into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (ie., an artificial membrane vesicle). The preparation and use of such systems is well known in the art.

Prostate Tumor Polypeptides

Within the context of the present invention, polypeptides may comprise at least a portion of a prostate tumor protein or a variant thereof, as described herein. As noted above, a "prostate tumor protein" is a protein that is overexpressed by prostate tumor cells, relative to normal prostate cells and/or other tissues such as brain, heart, kidney, liver, lung, pancreas, ovary, placenta, skeletal muscle, spleen and/or thymus. Such polypeptides should comprise a portion of a prostate tumor protein such that the therapeutic, antigenic and/or immunogenic properties of the polypeptide are not substantially diminished, relative to the full length protein. Within certain preferred embodiments, a polypeptide comprises an immunogenic portion of a native prostate tumor protein (i.e., the immunogenic properties of the polypeptide are not substantially diminished). As used herein, the term "polypeptide" encompasses amino acid chains of any length, including full length proteins, wherein the amino acid residues are linked by covalent peptide bonds. In addition to a portion of a prostate tumor protein, additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a prostate tumor protein or a variant thereof Immunogenic portions of prostate tumor proteins provided herein may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the antigen in an ELISA or other immunoassay, and do not react detectably with unrelated proteins). Such antisera and antibodies may be prepared as described herein, and using well known techniques. An immunogenic portion of a native prostate tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Alternatively, an immunogenic portion may react within such assays at a level that is diminished by less than 50%, and preferably less than 20%, relative to the full length polypeptide. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a polypeptide may comprise a variant of a native prostate tumor protein. A polypeptide "variant," as used herein, is a polypeptide that differs from a native prostate tumor protein in one or more substitutions, deletions, additions and/or insertions, such that the therapeutic, antigenic and/or immunogenic properties are not substantially diminished. Preferably, the immunogenic properties are not substantially diminished. In other words, the ability of a variant to react with antigen-specific antisera may be enhanced or unchanged, relative to the native antigen, or may be diminished by less than 50%, and preferably less than 20%, relative to the native antigen. Polypeptide variants preferably exhibit at least about 70%, more preferably at least about 90% and most preferably at least about 95% identity to polypeptides encoded by polynucleotides specifically recited herein. Identity may be determined by comparing sequences using computer algorithms well known to those of skill in the art, such as Megalign, using default parameters. For prostate tumor polypeptides with immunoreactive properties, variants may generally be identified by modifying one of the above polypeptide sequences and evaluating the reactivity of the modified polypeptide with antigen-specific antibodies or antisera as described herein. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants containing substitutions may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by polynucleotide sequences as described above may be readily prepared from the polynucleotide sequences using any of a variety of expression vectors known to those of ordinary skill in the art. Expression may be achieved in any appropriate host cell that has been transformed or transfected with an expression vector containing a polynucleotide molecule that encodes a recombinant polypeptide. Suitable host cells include prokaryotes, yeast and higher eukaryotic cells. Preferably, the host cells employed are *E. coli*, yeast or a mammalian cell line, such as CHO cells. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known prostate tumor antigen, or a variant of such an antigen. A fusion protein generally comprises at least one of the above immunogenic portions and one or more additional immunogenic prostate tumor sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

Fusion proteins may generally be prepared using standard techniques. For example, a fusion protein may be prepared recombinantly. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence may be incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated polynucleotide sequences are operably linked to suitable transcriptional or translational regulatory elements. The regulatory elements responsible for expression of polynucleotide are located only 5' to the polynucleotide sequence encoding the first polypeptides. Similarly, stop codons required to end translation and transcription termination signals are only present 3' to the polynucleotide sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a prostate tumor protein. As used herein, an agent is said to "specifically bind" to a prostate tumor protein if it reacts at a detectable level (within, for example, an ELISA) with a prostate tumor protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents are further capable of detecting metastatic prostate tumors and differentiating between patients with and without prostate cancer, using a representative assay provided herein. In other words, antibodies or other binding agents that bind to a prostate tumor protein will generate a signal indicating the presence of prostate cancer in at least about 20% of patients with the disease, and will generate a negative signal indicating the absence of the disease in at least about 90% of individuals without the cancer. To determine whether a binding agent satisfies this requirement, biological samples (e.g, blood, blood-associated tumor cells, sera, urine, biopsies and/or prostate secretions) from patients with and without prostate cancer (as determined using standard clinical tests) may be assayed as described herein for the presence of polypeptides or polynucleotides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

If an immunogenic portion is employed, the resulting antibody should indicate the presence of prostate cancer in substantially all (i.e., at least 80%, and preferably at least 90%) of the patients for which prostate cancer would be indicated using an antibody raised against the full length antigen. The antibody should also indicate the absence of prostate cancer in substantially all of those samples that would be negative when tested with an antibody raised against the full length antigen. The representative assays provided herein, such as the two-antibody sandwich assay, may generally be employed for evaluating the ability of an antibody to detect prostate cancer.

Binding agents may be further linked to a reporter group, to facilitate diagnostic assays. Suitable reporter groups will be apparent to those of ordinary skill in the art, and include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Such antibodies may be polyclonal or monoclonal. In addition, the antibodies may be single chain, chimeric, CDR-grafted or humanized.

Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process within, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{112}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. U.S. Pat. No. 4,673,562, to Davison et al. discloses representative chelating compounds and their synthesis.

A variety of routes of administration for the antibodies and immunoconjugates may be used. Typically, administration is intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Pharmaceutical Compositions and Vaccines

Within certain aspects, polypeptides, polynucleotides and/or binding agents may be incorporated into pharmaceutical compositions or vaccines. Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain polynucleotides encoding one or more of the polypeptides as described above, such that the polypeptide is generated in situ. As noted above, the polynucleotides may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N. Y. Acad Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., PNAS 91:215–219, 1994; Kass-Eisler et al., PNAS 90:11498–11502, 1993; Guzman et al., *Circulation* 88:2838–2848, 1993; and Guzman et al., *Cir. Res.* 73:1202–1207, 1993. Techniques for incorporating polynucleotides into such expression systems are well known to those of ordinary skill in the art. The polynucleotides may also be "naked," as described, for example, in Ulmer et al., *Science* 259:1745–1749, 1993 and reviewed by Cohen, *Science* 259:1691–1692, 1993. The uptake of naked polynucleotides may be increased by coating the polynucleotides onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration including, for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g, glucose, mannose, sucrose or dextrans), mannitol, proteins, polypeptides or amino acids such as glycine, antioxidants, chelating agents such as EDTA or glutathione, adjuvants (e.g, aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, Bortadella pertussis or Mycobacterium tuberculosis derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Cancer Therapy

In further aspects of the present invention, the pharmaceutical compositions and vaccines described herein may be used for immunotherapy of cancer, such as prostate cancer, in a patient. Polypeptides for use within such compositions and vaccines generally comprise an immunogenic portion of a prostate tumor protein, or a variant thereof. Such polypeptides may stimulate the patient's own immune response to prostate tumor cells. Alternatively, a pharmaceutical composition or vaccine may comprise one or more fusion proteins comprising one or more such polypeptides and/or polynucleotides encoding such one or more such polypeptides. Monoclonal antibodies of the present invention may also be used as therapeutic reagents, to diminish or eliminate prostate tumors. The antibodies may be used on their own (for instance, to inhibit metastases) or coupled to one or more therapeutic agents, as described above.

Within such methods, pharmaceutical compositions and vaccines are typically administered to a patient. As used herein, a "patient" refers to any warm-blooded animal, preferably a human. A patient may be afflicted with a disease, or may be free of detectable disease. Accordingly, the above pharmaceutical compositions and vaccines may be used to prevent the development of prostate cancer or to treat a patient afflicted with prostate cancer. Prostate cancer may be diagnosed using criteria generally accepted in the art. Pharmaceutical compositions and vaccines may be administered either prior to or following surgical removal of primary tumors and/or treatment such as administration of radiotherapy or conventional chemotherapeutic drugs.

Routes and frequency of administration, as well as dosage, will vary from individual to individual, and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or polynucleotide that is effective to raise an immune response (cellular and/or humoral) against prostate tumor cells in a treated patient. A suitable immune response is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, the amount of polypeptide present in a dose (or produced in situ by the polynucleotides molecule in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 mL. A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or trnasduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited, " *Immunological Reviews*, 157:177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.*, 22(3), 213, 1996). Cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from tumor specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother*, 45(3–4):131–6, 1997 and Hwu, P., et al, *Cancer Res*, 55(15):3369–73, 1995. Another embodiment may include the transfection of tumor antigen specific alpha and beta T cell receptor chains into alternate T cells, as in Cole, D J, et al, *Cancer Res*, 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al, *Immunological Reviews*, 157:177, 1997).

Additionally, vectors expressing the disclosed polynucleotides may be introduced into stem cells taken from the patient and clonally propagated in vitro for autologous transplant back into the same patient.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a prostate tumor protein generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more prostate tumor proteins and/or polynucleotides encoding such proteins in a biological sample obtained from the patient. In other words, such proteins may be used as markers to indicate the presence or absence of prostate cancer. The binding agents provided herein generally permit detection of the level of protein that binds to the agent in the biological sample. Alternatively, polynucleotide primers and probes may be used to detect the level of mRNA encoding an antigen, which is also indicative of the presence or absence of prostate cancer.

There are a variety of assay formats known to those of ordinary skill in the art for using a binding agent to detect polypeptide markers in a sample. See, e.g., Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length prostate tumor proteins and portions thereof to which the binding agent binds, as described above.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value for the detection of prostate cancer is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of prostate cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would. be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or binding agents of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, the cancer is not progressing when the level of reactive polypeptide either remains constant or decreases with time.

As noted above, prostate cancer may also, or alternatively, be detected based on the level of mRNA encoding a prostate tumor protein in a biological sample. For example, at least two oligonucleotide primers may be employed in a polymerase chain reaction (PCR) based assay to amplify a portion of a prostate tumor protein cDNA derived from a biological sample, wherein at least one of the oligonucleotide primers is specific for (i.e., hybridizes to) a polynucleotide encoding the prostate tumor protein. The amplified cDNA is then separated and detected using techniques well known in the art, such as gel electrophoresis. Similarly, oligonucleotide probes that specifically hybridize to a polynucleotide encoding a prostate tumor protein may be used in a hybridization assay to detect the presence of polynucleotide encoding the antigen in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a prostate tumor protein that is at least 10 nucleotides, and preferably at least 20 nucleotides, in length. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule recited herein. Techniques for both PCR based assays and hybridization assays are well known in the art (see, for example, Mullis et al., *Cold Spring Harbor Symp. Quant. Biol.,* 51:263, 1987; Erlich ed., *PCR Technology,* Stockton Press, NY, 1989).

One preferred assay employs RT-PCR, in which PCR is applied in conjunction with reverse transcription. Typically, RNA is extracted from a sample tissue and is reverse transcribed to produce cDNA molecules. PCR amplification using at least one specific primer generates a cDNA molecule, which may be separated and visualized using, for example, gel electrophoresis. Amplification may be performed on samples obtained from biological samples taken from a test patient and an individual who is not afflicted with prostate cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple prostate tumor protein markers may be assayed within a given sample. It will be apparent that binding agents specific for different antigens provided herein may be combined within a single assay. Further, multiple primers or probes may be used concurrently. The selection of antigen markers may be based on routine experiments to determine combinations that results in optimal sensitivity. In addition, or alternatively, assays for antigens provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a prostate tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a prostate tumor protein in a biological sample. Such kits generally comprise at least one oligonucleotide probe or primer, as described above, that hybridizes to a polynucleotide encoding a prostate tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a prostate tumor protein.

The following Examples are offered by way of illustration and not by way of limitation.

EXAMPLES

Example 1

Isolation and Characterization of Prostate Tumor Polypeptides

This Example describes the isolation of certain prostate tumor polypeptides from a prostate tumor cDNA library.

A human prostate tumor cDNA expression library was constructed from prostate tumor poly $A^+$ RNA using a Superscript Plasmid System for cDNA Synthesis and Plasmid Cloning kit (BRL Life Technologies,.Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif.), the cDNA was ligated into the EcoRI/NotI site of pCDNA3.1 (Invitrogen) and transformed into ElectroMax E. coli DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of $H_2O$, heat-denatured and mixed with 100 μl (100 μg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl $H_2O$ to form the driver DNA.

To form the tracer DNA, 10 μg prostate tumor cDNA library was digested with BamHI and XhoI, phenol chloroform extracted and passed through Chroma spin-400 columns (Clontech). Following ethanol precipitation, the tracer DNA was dissolved in 5 μl $H_2O$. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl $H_2O$, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK⁻ (Stratagene, La Jolla, Calif. 92037) and transformed into ElectroMax E. Coli DH10B cells by electroporation to generate a prostate tumor specific subtracted cDNA library (prostate subtraction 1).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 µg each of human glandular kallikrein, PSA and mitochondria cytochrome C oxidase subunit II cDNAs in pCDNA3. 1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J 1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, 28–29 respectively).

Subsequent studies led to the isolation of full length cDNA sequences for J1-17, L1-12 and N1-1 862 (SEQ ID NOS: 109–111, respectively). The corresponding predicted amino acid sequences are provided in SEQ ID NOS: 112–114. L1-12 is also referred to as P501S.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene.

Four additional clones, hereinafter referred to as V1-3686, R1-2330, IB-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 114810, 1I-4811, 1J-4876, 1K-4884 and 1K-4896. The determined cDNA sequences for these clones are provided in SEQ ID NOS: 77–92, respectively. Comparison of these sequences with those in the gene bank as described above, revealed no significant homologies to 1G-4741, 1G-4734, 114807, 1J-4876 and 1K-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 11–4810 and 1I-4811, provided in SEQ ID NOS: 189 and 190, respectively.

Additional studies with prostate subtraction spike 2 resulted in the isolation of three more clones. Their sequences were determined as described above and compared to the most recent Genbank. All three clones were found to have homology to known genes, which are Cysteine-rich protein, KIAA0242, and KIAA0280 (SEQ ID NO: 317, 319, and 320, respectively). Further analysis of these clones by Synteni microarray (Synteni, Palo Alto, Calif.) demonstrated that all three clones were overexpressed in most prostate tumors and prostate BPH, as well as in the majority of normal prostate tissues tested, but low expression in all other normal tissues.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D-1-4278, ID-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Additionally, the full-length cDNA sequence for P509S (SEQ ID NO: 223) is provided in SEQ ID NO: 332.

Example 2

Determination of Tissue Specificity of Prostate Tumor Polypeptides

Using gene specific primers, mRNA expression levels for the representative prostate tumor polypeptides F1-16, H1-1, J1-17 (also referred to as P502S), L1-12 (also referred to as P501S), F1-12 (also referred to as P504S) and N1-1862 (also referred to as P503S) were examined in a variety of normal and tumor tissues using RT-PCR.

Briefly, total RNA was extracted from a variety of normal and tumor tissues using Trizol reagent as described above. First strand synthesis was carried out using 1–2 μg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 (P502S) and L1-12 (P501S) appear to be specifically over-expressed in prostate, with both genes being expressed at high levels in prostate tumor and normal prostate but at low to undetectable levels in all the other tissues examined. N1-1862 (P503S) was found to be over-expressed in 60% of prostate tumors and detectable in normal colon and kidney. The RT-PCR results thus indicate that F1-16, H1-1, J1-17 (P502S), N1-1862 (P503S) and L1-12 (P501S) are either prostate specific or are expressed at significantly elevated levels in prostate.

Further RT-PCR studies showed that F1-12 (P504S) is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 (P501S) is over-expressed in prostate tumors and normal prostate, while being undetectable in other normal tissues tested. J1-17 (P502S) was detected in two prostate tumors and not in the other tissues tested. N1-1862 (P503S) was found to be over-expressed in three prostate tumors and to be expressed in normal prostate, colon and kidney, but not in other tissues tested. F1-12 (P504S) was found to be-highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 (P501S) was found to be over-expressed in normal prostate and prostate tumor, with some expression being detected in normal skeletal muscle. Both J1-12and F1-12 (P504S) were found to be over-expressed in prostate tumor, with expression being lower or undetectable in all other tissues tested. N1-1862 (P503S) was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Further studies to specifically address the extent to which P501S (SEQ ID NO: 110) was expressed in breast tumor by microarray analysis revealed moderate over-expression in not only breast tumor, but also in metastatic breast tumor (2/31), with negligable to low expression in normal tisssues. This data suggests that P501S may be over-expressed in various breast tumors as well as in prostate tumors.

Example 3

Isolation and Characterization of Prostate Tumor Polypeptides by PCR-Based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' E. coli (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P79 and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. Larger cDNA clones containing the P20 sequence represent splice variants of a gene referred to as P703P. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively. mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20, a portion of the P703P gene, was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8, 10-h10, 10-c8, 7-g6, 8-b5, 8-b6, 8-d4, 8-d9h11 , 9-f12 and 9-f3. The determined DNA sequences for 10-d8, 10-h10, 11-c8, 8-d4, 8-d9, 8-h11, 9-f12 and 9-f3 are provided in SEQ ID NO: 207, 208, 209, 216, 217,.220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-f12 were found to show some homology to previously identified genes. Further characterization of 7-G6 and 8-G3 showed identity to the known genes PAP and PSA, respectively.

mRNA expression levels for these clones were determined using the micro-array technology described above. The clones 7-G6, 8-G3, 8-B5, 8-B6, 8-D4, 8-D9, 9-F3, 9-F1 2, 9-H3, 10-A2, 10-A4, I 1-C9 and 1 1-F2 were found to be over-expressed in prostate tumor and normal prostate, with expression in other tissues tested being low or undetectable.

Increased expression of 8-F11 was seen in prostate tumor and normal prostate, bladder, skeletal muscle and colon. Increased expression of 10-H10 was seen in prostate tumor and normal prostate, bladder, lung, colon, brain and large intestine. Increased expression of 9-B1 was seen in prostate tumor, breast tumor, and normal prostate, salivary gland, large intestine and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RT-PCR. The determined cDNA sequence of this clone (referred to as 9-A11) is provided in SEQ ID NO: 226. Comparison of this sequence with those in the public databases revealed 99% identity to the known gene HOXB 13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

PCR and hybridization-based methodologies were employed to obtain longer cDNA sequences for clone P20 (also referred to as P703P), yielding three additional cDNA fragments that progressively extend the 5' end of the gene. These fragments, referred to as P703PDE5, P703P6.26, and P703PX-23 (SEQ ID NO: 326, 328, and 330, with the predicted corresponding amino acid sequences in SEQ ID NO: 327, 329, and 331, respectively) contain additional 5' sequence. P703PDE5 was recovered by screening of a cDNA library (#141-26) with a portion of P703P as a probe. P703P6.26 was recovered from a mixture of three prostate tumor cDNAs and P703PX__23 was recovered from cDNA library (#438–48). Together, the additional sequences include all of the putative mature serine protease along with the majority of the putative signal sequence. Further studies using a PCR-based subtraction library of a prostate tumor pool subtracted against a pool of normal tissues (referred to as JP: PCR subtraction) resulted in the isolation of thirteen additional clones, seven of which did not share any significant homology to known Genbank sequences. The determined cDNA sequences for novel clones P711P, P712P, novel 23, P774P, P775P, P710P, and P768P are provided in SEQ ID NO: 307–311, 313, and 315, respectively. The remaining six clones (SEQ ID NO: 316, and 321–325) were shown to share homology to known genes. By microarray analysis, all thirteen clones showed three or more fold over-expression in prostate tissues, including prostate tumors, BPH, and normal prostate as compared to normal non-prostate tissues. Clones P711P, P712P, novel 23, and P768P showed over-expression in most prostate tumors and BPH tissues tested (n=29), and in the majority of normal prostate tissues (n=4), but background to low expression levels in all normal tissues. Clones P774P, P775P, and P710P showed comparatively lower expression and expression in fewer prostate tumors and BPH samples, with negative to low expression in normal prostate.

Using PCR and hybridization-based methodologies, additional cDNA sequence information was derived for two clones described above, 11-C9 and 9-F3, herein after referred to as P707P, and P714P, respectively (SEQ ID NO: 333 and 334). After comparison with the most recent Genbank, P707P was found to be a splice variant of the known gene HoxB13. While there are some differences in the published sequence and the derived cDNA sequence, the differences are likely due to allelic variation. In contrast, P714P does not share homology with a any known gene sequences and therefore is novel.

Additionally, clones 8-B3, P89, P98, P130, and P201 (as disclosed in U.S. patent application Ser. No. 09/020,956, filed Feb. 9, 1998) were found to be contained within one contiguous sequence, referred to as P705P (SEQ ID NO: 335, with the predicted amino acid sequence provided in SEQ ID NO: 336), which was determined to be a splice variant of the known gene NKX 3.1.

Example 4

Synthesis of Polypeptides

Polypeptides may be synthesized on a Perkin Elmer/Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 5

Further Isolation and Characterization of Prostate Tumor Polypeptides by PCR-Based Subtraction A cDNA library generated from prostate primary tumor mRNA as described above was subtracted with cDNA from normal prostate. The subtraction was performed using a PCR-based protocol (Clontech), which was modified to generate larger fragments. Within this protocol, tester and driver double stranded cDNA were separately digested with five restriction enzymes that recognize six-nucleotide restriction sites (MluI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cDNAs, (b) tester cDNAs hybridized to other tester cDNAs, (c) tester cDNAs hybridized to driver cDNAs and (d) unhybridized driver cDNAs. The two separate hybridization reactions were then combined, and rehybridized in the presence of additional denatured driver cDNA. Following this second hybridization, in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are overexpressed in prostate tumor tissue may be recoverable. Such transcripts would be difficult to recover by traditional subtraction methods.

In addition to genes known to be overexpressed in prostate tumor, seventy-seven novel clones were identified. Sequences of these partial cDNAs are provided in SEQ ID NOs:229 to 305. Most of these clones had no significant homology to database sequences. Exceptions were JPTPN23 (SEQ ID NO:231; similarity to pig valosin-containing protein), JPTPN30 (SEQ ID NO:234; similarity to rat mRNA for proteasome subunit), JPTPN45 (SEQ ID NO:243; similarity to rat norvegicus cytosolic NADP-dependent isocitrate dehydrogenase), JPTPN46 (SEQ ID NO:244; similarity to human subclone H8 4 d4 DNA sequence), JP1D6 (SEQ ID NO:265; similarity to *G. gallus* dynein light chain-A), JP8D6 (SEQ ID NO:288); similarity to human BAC clone RG016J04), JP8F5 (SEQ ID NO:289; similarity to human subclone H8 3 b5 DNA sequence) and JP8E9 (SEQ ID NO:299; similarity to human Alu sequence).

The novel clones identified were:

| | |
|---|---|
| JPTPN13 | SEQ ID NO:229 |
| JPTPN14 | SEQ ID NO:230 |
| JPTPN23 | SEQ ID NO:231 |
| JPTPN24 | SEQ ID NO:232 |
| JPTPN25 | SEQ ID NO:233 |
| JPTPN30 | SEQ ID NO:234 |
| JPTPN34 | SEQ ID NO:235 |
| JPTPN35 | SEQ ID NO:236 |
| JPTPN36 | SEQ ID NO:237 |
| JPTPN38 | SEQ ID NO:238 |
| JPTPN39 | SEQ ID NO:239 |
| JPTPN40 | SEQ ID NO:240 |
| JPTPN41 | SEQ ID NO:241 |
| JPTPN42 | SEQ ID NO:242 |
| JPTPN45 | SEQ ID NO:243 |
| JPTPN46 | SEQ ID NO:244 |
| JPTPN51 | SEQ ID NO:245 |
| JPTPN56 | SEQ ID NO:246 |
| JPTPN64 | SEQ ID NO:247 |
| JPTPN65 | SEQ ID NO:248 |
| JPTPN67 | SEQ ID NO:249 |
| JPTPN76 | SEQ ID NO:250 |
| JPTPN84 | SEQ ID NO:251 |
| JPTPN85 | SEQ ID NO:252 |
| JPTPN86 | SEQ ID NO:253 |
| JPTPN87 | SEQ ID NO:254 |
| JPTPN88 | SEQ ID NO:255 |
| JP1F1 | SEQ ID NO:256 |
| JP1F2 | SEQ ID NO:257 |
| JP1C2 | SEQ ID NO:258 |
| JP1B1 | SEQ ID NO:259 |
| JP1B2 | SEQ ID NO:260 |
| JP1D3 | SEQ ID NO:261 |
| JP1A4 | SEQ ID NO:262 |
| JP1F5 | SEQ ID NO:263 |
| JP1E6 | SEQ ID NO:264 |
| JP1D6 | SEQ ID NO:265 |
| JP1B5 | SEQ ID NO:266 |
| JP1A6 | SEQ ID NO:267 |
| JP1E8 | SEQ ID NO:268 |
| JP1D7 | SEQ ID NO:269 |
| JP1D9 | SEQ ID NO:270 |
| JP1C10 | SEQ ID NO:271 |
| JP1A9 | SEQ ID NO:272 |
| JP1F12 | SEQ ID NO:273 |
| JP1E12 | SEQ ID NO:274 |
| JP1D11 | SEQ ID NO:275 |
| JP1C11 | SEQ ID NO:276 |
| JP1C12 | SEQ ID NO:277 |
| JP1B12 | SEQ ID NO:278 |
| JP1A12 | SEQ ID NO:279 |
| JP8G2 | SEQ ID NO:280 |
| JP8H1 | SEQ ID NO:281 |
| JP8H2 | SEQ ID NO:282 |
| JP8A3 | SEQ ID NO:283 |
| JP8A4 | SEQ ID NO:284 |
| JP8C3 | SEQ ID NO:285 |
| JP8G4 | SEQ ID NO:286 |
| JP8B6 | SEQ ID NO:287 |
| JP8D6 | SEQ ID NO:288 |
| JP8F5 | SEQ ID NO:289 |
| JP8A8 | SEQ ID NO:290 |
| JP8C7 | SEQ ID NO:291 |
| JP8D7 | SEQ ID NO:292 |
| JP8D8 | SEQ ID NO:293 |
| JP8E7 | SEQ ID NO:294 |
| JP8F8 | SEQ ID NO:295 |
| JP8G8 | SEQ ID NO:296 |
| JP8B10 | SEQ ID NO:297 |
| JP8C10 | SEQ ID NO:298 |
| JP8E9 | SEQ ID NO:299 |
| JP8E10 | SEQ ID NO:300 |
| JP8F9 | SEQ ID NO:301 |
| JP8H9 | SEQ ID NO:302 |
| JP8C12 | SEQ ID NO:303 |
| JP8E11 | SEQ ID NO:304 |
| JP8E12 | SEQ ID NO:305 |

Additional studies using the PCR-based subtraction library consisting of a prostate tumor pool subtracted against a normal prostate pool (referred to as PT-PN PCR subtraction) yielded three additional clones. Comparison of the cDNA sequences of these clones with the most recent Genbank revealed two to be novel, herein after referred to as P715P and P767P (SEQ ID NO: 312 and 314). The remaining clone was shown to share homology to the known gene KIAA0056 (SEQ ID NO: 318). Using microarray analysis to measure mRNA expression levels in various tissues, all three clones were found to be over-expressed in prostate tumors and BPH tissues. Specifically, clone P715P was over-expressed in most prostate tumors and BPH tissues by a factor of three or greater, with elevated expression seen in the majority of normal prostate samples and in fetal tissue, but negative to low expression in all other normal tissues. Clone P767P was over-expressed in several prostate tumors and BPH tissues, with moderate expression levels in half of the normal prostate samples, and background to low expression in all other normal tissues tested.

Example 6

Peptide Priming of Mice and Propagation of CTL Lines 6.1. This Example illustrates the preparation of a CTL cell line specific for cells expressing the P502S gene.

Mice expressing the transgene for human HLA A2.1 (provided by Dr L. Sherman, The Scripps Research Institute, La Jolla, Calif.) were immunized with P2S #12 peptide (VLGWVAEL; SEQ ID NO: 306), which is derived from the P502S gene (also referred to herein as J1-17, SEQ ID NO:8), as described by Theobald et al., *Proc. Natl. Acad Sci. USA* 92:11993–11997, 1995 with the following modifications. Mice were immunized with 100μg of P2S #12 and 120μg of an I-A$^b$ binding peptide derived from hepatitis B Virus protein emulsified in incomplete Freund's adjuvant. Three weeks later these mice were sacrificed and using a nylon mesh single cell suspensions prepared. Cells were then resuspended at 6×106 cells/ml in complete media (RPMI-1640(Gibco BRL, Gaithersburg, Md.) containing 10% FCS, 2mM Glutamine (Gibco BRL), sodium pyruvate (Gibco BRL), non- essential amino acids (Gibco BRL, 2×10$^{-5}$ M 2-mercaptoethanol, 50 U/ml penicillin and streptomycin) and cultured in the presence of irradiated (3000rads) P2S#12 pulsed (5 mg/ml P2S #12 and 10mg/ml β2-microglobulin) LPS blasts (A2 transgenic spleens cells cultured in the presence of 7 μg/ml dextran sulfate and 25 μg/ml LPS for 3 days). Six days later cells (5×10$^5$ /ml) were restimulated with 2.5×10$^6$ /ml peptide pulsed irradiated (20,000rads) EL4A2Kb cells (Sherman et al, *Science* 258:815–818, 1992) and 3×10$^6$ /ml A2 transgenic spleen feeder cells. Cells were cultured in the presence of 20 U/ml IL-2. Cells were continued to be restimulated on a weekly basis as mentioned, in preparation for cloning the line.

P2S#12 line was cloned by limiting dilution analysis with peptide pulsed EL4 A2Kb tumor cells (1×10$^4$ cells/ well) as stimulators and A2 transgenic spleen cells as feeders (5×10$^5$ cells/ well) grown in the presence of 30 U/ml IL-2. On day 14, cells were restimulated as before. On day 21, clones that were growing were isolated and maintained in culture. Several of these clones demonstrated reactivity (lysis) against human fibroblasts (HLA A2.1 expressing) transduced with P502S gene significantly higher than control fibroblasts. An example is presented in FIG. 1.

This data indicates that P2S #12 represents a naturally processed epitope of the P502S protein that is expressed in the context of the human HLA A2.1 molecule.

6.2. This Example illustrates the preparation of murine CTL lines and CTL clones specific for cells expressing the P501S gene.

Figure 3:
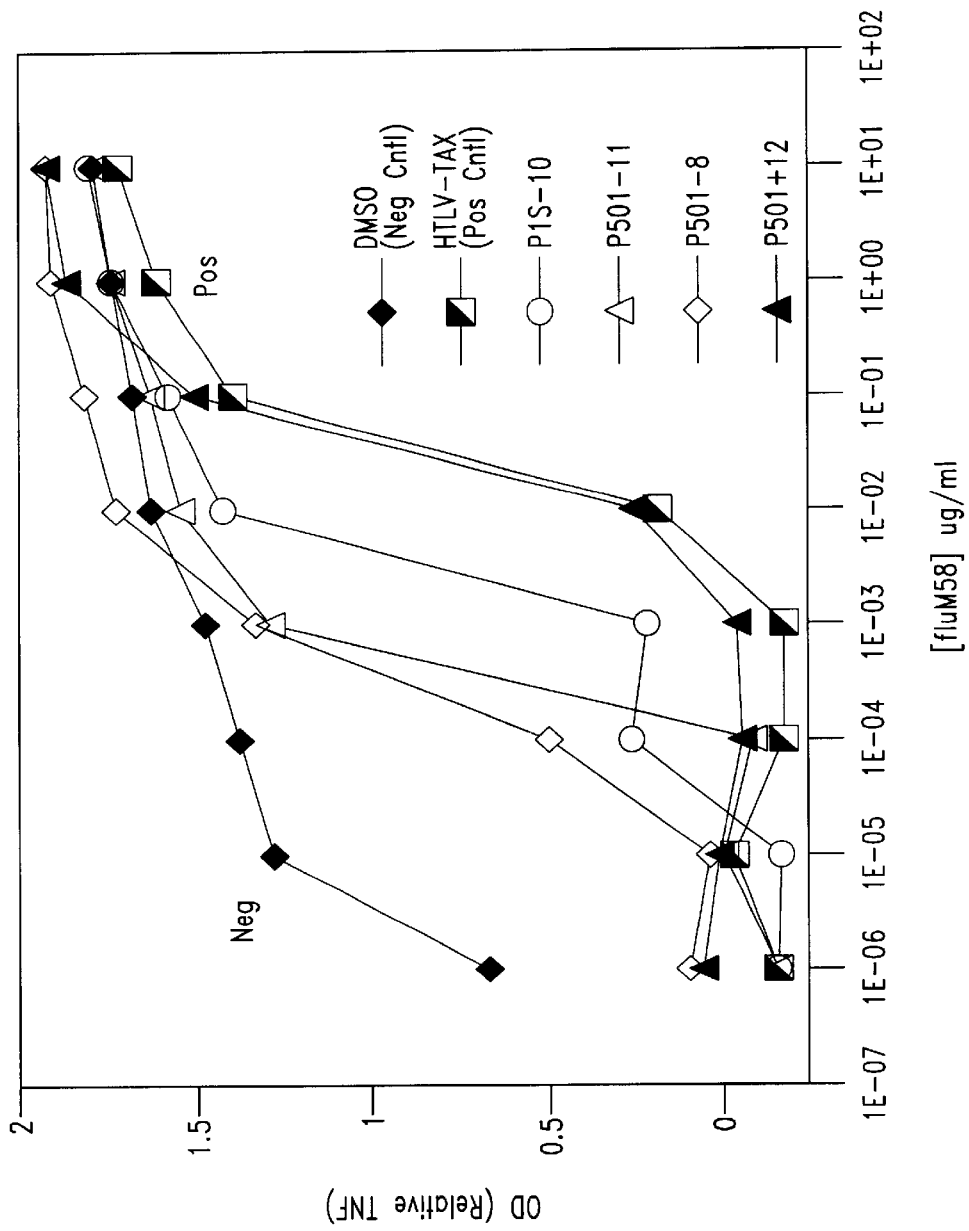
FIG. 3 represents a peptide competition binding assay showing that the P1S#10 peptide, derived from P501S, binds HLA-A2. Peptide P1S#10 inhibits HLA-A2 restricted presentation of fluM58 peptide to CTL clone D150M58 in TNF release bioassay. D150M58 CTL is specific for the HLA-A2 binding influenza matrix peptide fluM58.

This series of experiments were performed similarly to that described above. Mice were immunized with the P1S#10 peptide (SEQ ID NO: 337), which is derived from the P501S gene (also referred to herein as L1-12, SEQ ID NO: 110). The P1S#10 peptide was derived by analysis of the predicted polypeptide sequence for P501S for potential HLA-A2 binding sequences as defined by published HLA-A2 binding motifs (Parker, K C, et al, J. Immunol., 152:163, 1994). P1S#10 peptide was synthesized by methods described in Example 4, and empirically tested for HLA-A2 binding using a T cell based competition assay. Predicted A2 binding peptides were tested for their ability to compete HLA-A2 specific peptide presentation to an HLA-A2 restricted CTL clone (D150M58), which is specific for the HLA-A2 binding influenza matrix peptide fluM58. D150M58 CTL secretes TNF in response to self-presentation of peptide fluM58. In the competition assay, test peptides at 100–200 ug/ml were added to cultures of D150M58 CTL in order to bind HLA-A2 on the CTL. After thirty minutes, CTL cultured with test peptides, or control peptides, were tested for their antigen dose response to the fluM58 peptide in a standard TNF bioassay. FIG. 3 shows peptide P1S#10 competes HLA-A2 restricted presentation of fluM58, demonstrating that peptide P1S#10 binds HLA-A2.

Figure 4:
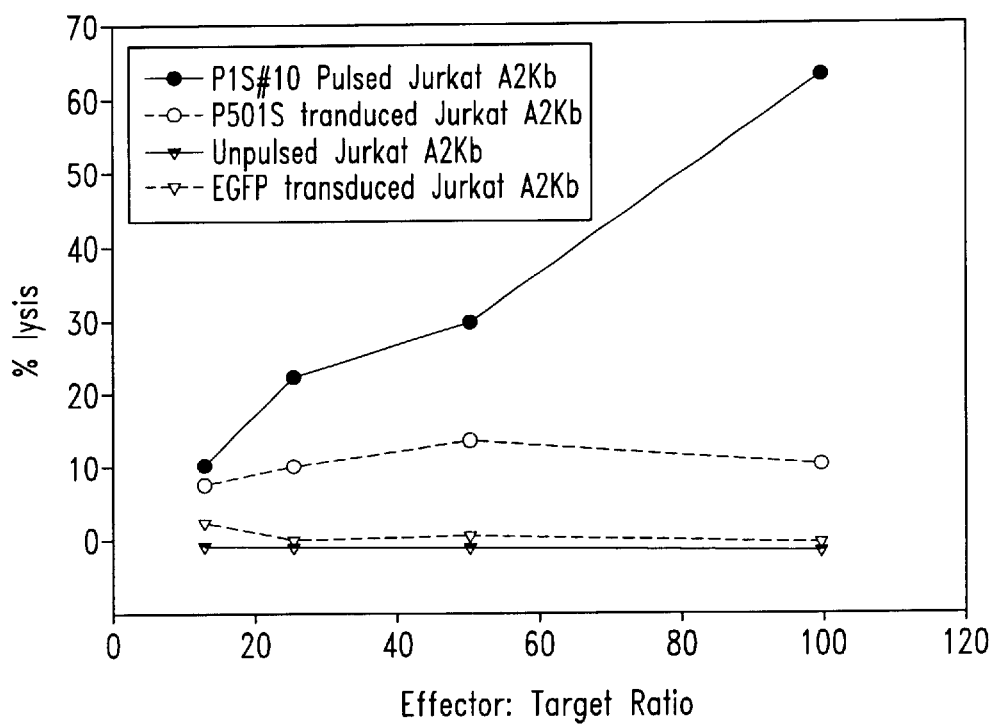
FIG. 4 is a graph illustrating the ability of T cell lines generated from P1S#10 immunized mice to specifically lyse PlS#10-pulsed Jurkat A2Kb targets and P501S-transduced Jurkat A2Kb targets, as compared to EGFP-transduced Jurkat A2Kb. The percent lysis is shown as a series of effector to target ratios, as indicated.

Mice expressing the transgene for human HLA A2.1 were immunized as described by Theobald et al., *Proc. Natl. Acad. Sci. USA* 92:11993–11997, 1995 with the following modifications. Mice were immunized with 62.5 μg of P1S #10 and 120 μg of an I-A$^b$ binding peptide derived from Hepatitis B Virus protein emulsified in incomplete Freund's adjuvant. Three weeks later these mice were sacrificed and using a nylon mesh single cell suspensions prepared. Cells were then resuspended at 6×10$^6$ cells/ml in complete media (as described above) and cultured in the presence of irradiated (3000rads) P1S#10 pulsed (2 μg/ml P1S#10 and 10 mg/ml β2-microglobulin) LPS blasts (A2 transgenic spleens cells cultured in the presence of 7 μg/ml dextran sulfate and 25 μg/ml LPS for 3 days). Six days later cells (5×10$^5$/ml) were restimulated with 2.5×10$^6$/ml peptide-pulsed irradiated (20,000rads) EL4A2Kb cells, as described above, and 3×10$^6$/ml A2 transgenic spleen feeder cells. Cells were cultured in the presence of 20 U/ml IL-2. Cells were restimulated on a weekly basis in preparation for cloning. After three rounds of in vitro stimulations, one line was generated that recognized P1S#10-pulsed Jurkat A2Kb targets and P501S-transduced Jurkat targets as shown in FIG. 4.

Figure 5:
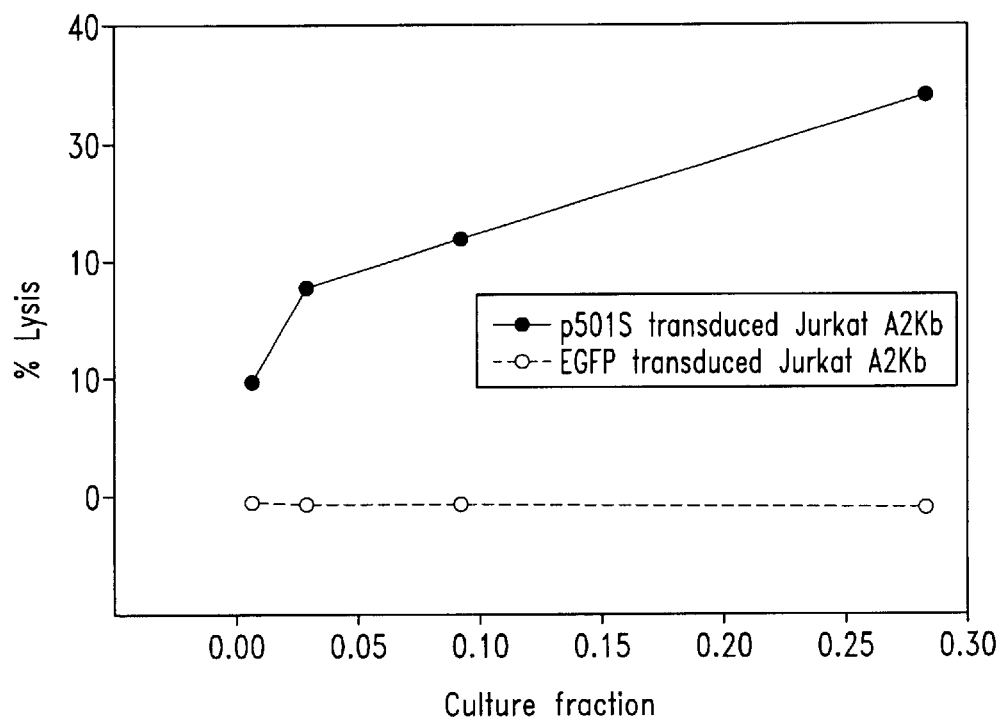
FIG. 5 illustrates the ability of a T cell clone to recognize and specifically lyse Jurkat A2Kb cells expressing the representative prostate tumor polypeptide P501S, thereby demonstrating that the P1S#10 peptide may be a naturally processed epitope of the P501S polypeptide.

A P1S#10-specific CTL line was cloned by limiting dilution analysis with peptide pulsed EL4 A2Kb tumor cells (1×10$^4$ cells/ well) as stimulators and A2 transgenic spleen cells as feeders (5×10$^5$ cells/ well) grown in the presence of 30 U/ml IL-2. On day 14, cells were restimulated as before. On day 21, viable clones were isolated and maintained in culture. Five of these clones demonstrated specific cytolytic reactivity against P501S-transduced Jurkat A2Kb targets. As shown in FIG. 5, this data indicates that P1S#10 represents a naturally processed epitope of the P501S protein that is expressed in the context of the human HLA-A2.1 molecule.

Example 7

Ability of Human T Cells to Recognize Prostate Tumor Polypeptides

This Example illustrates the ability of T cells specific for a prostate tumor polypeptide to recognize human tumor.

Figure 2A:
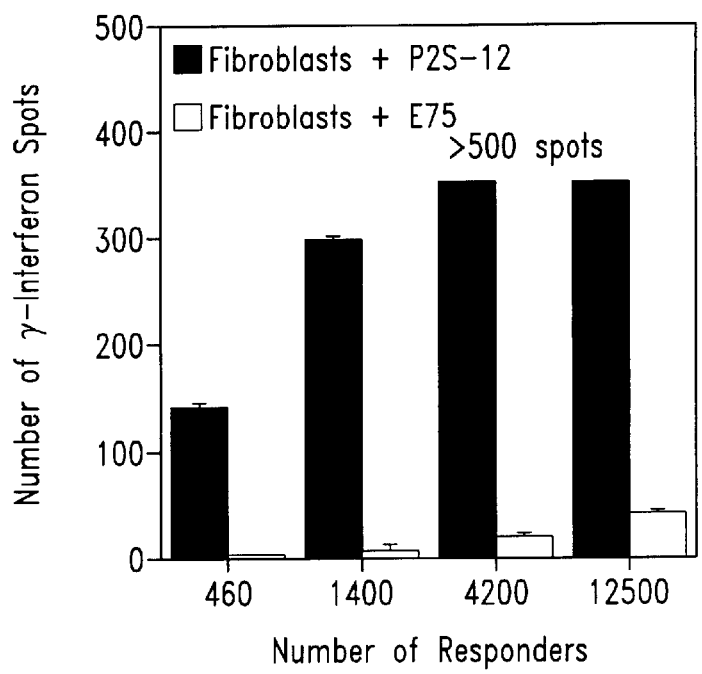
FIGS. 2A and 2B are graphs illustrating the ability of T cells to recognize cells expressing the representative prostate tumor polypeptide P502S. In each case, the number of γ-interferon spots is shown for different numbers of responders.
Figure 2B:
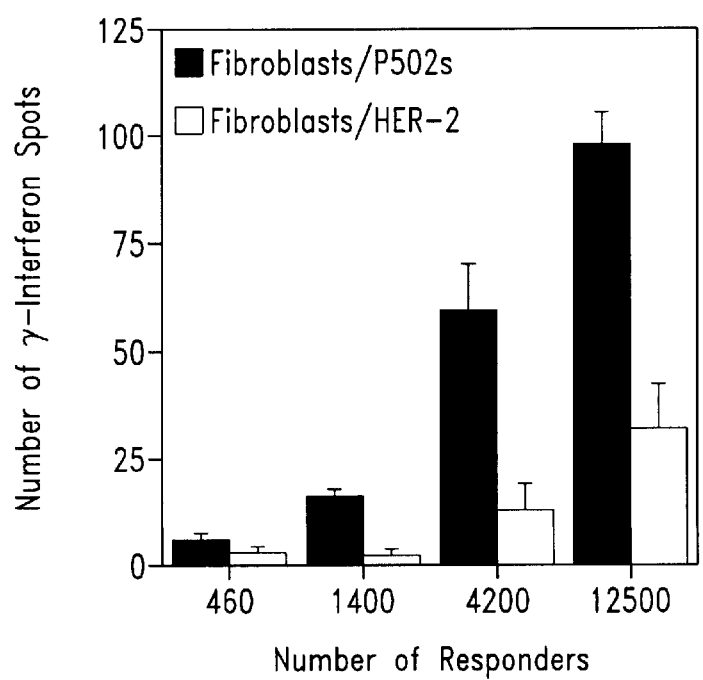

Human CD8$^+$ T cells were primed in vitro to the P2S-12 peptide (VLGWVAEL; SEQ ID NO:306) derived from the P502S (J1-17) gene using dendritic cells according to protocol set forth by Van Tsai et al., *Critical Reviews in Immunology* 18:65–75, 1998. The resulting CD8$^+$ T cell microcultures were tested for their ability to recognize the P2S-12 peptide presented by autologous fibroblasts or fibroblasts which were transduced to express the P502S gene in a γ-interferon ELISPOT assay (see Lalvani et al., *J. Experimental Medicine* 186:859–865, 1997). Briefly, titrating numbers of T cells were assayed in duplicate on 10$^4$ fibroblasts in the presence of 3 μg/ml human β$_2$-microglobulin and 1 μg/ml P2S-12 peptide or control E75 peptide. In addition, T cells were simultaneously assayed on autologous fibroblasts transduced with the P502S gene or as a control, fibroblasts transduced with HER-2/neu. Prior to the assay, the fibroblasts were treated with 10 ng/ml γ-interferon for 48 hours to upregulate class I MHC expression. One of the microcultures (#5) demonstrated strong recognition of both peptide pulsed fibroblasts as well as transduced fibroblasts in a γ-interferon ELISPOT assay. FIG. 2A demonstrates that there was a strong increase in the number of γ-interferon spots with increasing numbers of T cells on fibroblasts pulsed with the P2S-12 peptide (solid bars) but not with the control E75 peptide (open bars). This shows the ability of these T cells to specifically recognize the P2S-12 peptide. In FIG. 2B, this microculture also demonstrated an increase in the number of γ-interferon spots with increasing numbers of T cells on fibroblasts transduced to express the P502S gene but not the HER-2/neu gene. These results provide additional confirmatory evidence that the P2S-12 peptide is a naturally processed epitope of the P502S protein. Furthermore, this also demonstrates that there exists in the human T cell repertoire, high affinity T cells which are capable of recognizing this epitope. These T cells should also be capable of recognizing human tumors which express the P502S gene.

Example 8

Priming of CTL In Vivo Using Naked DNA Immunization with a Novel Prostate Antigen The novel prostate tumor antigen L1-12, as described above, is also referred to as P501S. HLA A2Kb Tg mice, (provided by Dr L. Sherman, The Scripps Research Institute, La Jolla, Calif.) were immunized with 100 ug VR10132-P501S either intramuscularly or intradermally. The mice were immunized three times, with a two week interval between immunizations. Two weeks after the last immunization, immune spleen cells were cultured with Jurkat A2Kb-P501S transduced stimulator cells. CTL lines were stimulated weekly. After two weeks of in vitro stimulation, CTL activity was assessed against P501S transduced targets. The results show that 2/8 mice developed strong anti-P501S CTL responses. These results demonstrate that P501S contains at least one naturally processed A2-restricted CTL epitope.

Example 9

Generation of Human CTL In Vitro Using Whole Gene Priming and Stimulation Techniques with Novel Prostate Tumor Antigen The novel prostate antigen L1-12, as described above, is also referred to as P501S. Using in vitro whole-gene priming with P501S-retrovirally transduced autologous fibroblasts, (see, for example, Yee et al, *The Journal of Immunology*, 157(9):4079–86, 1996) human CTL lines were derived that specifically recognize autologous fibroblasts transduced with P501S, as determined by interferon-γ ELISPOT analysis (as described above). Using a panel of HLA-mismatched fibroblast lines transduced with P501S, these CTL lines were shown to be restricted HLA-A2 class I allele. Specifically, dendritic cells (DC) were differentiated from monocyte cultures derived from PBMC of normal human donors by growth for five days in RPMI medium containing 10% human serum and 50 ng/ml human GM-CSF and 30 ng/ml human IL-4. Following culture, DC were infected overnight with recombinant PS50S vaccinia virus at a multiplicity of infection (M.O.I) of five, and matured overnight by the addition of 3 υg/ml. CD40 ligand. Virus was inactivated by U.V. irradiation and CD8+ T cells were isolated using a magnetic bead system, and priming cultures were initiated using standard culture techniques. Cultures were restimulated every 7–10 days using autologous primary fibroblasts retrovirally transduced with P501S. Following four stimulations cycles, CD8+ T cell lines could be identified that specifically produced interferon-γ when stimulated with P501S-transduced autologous fibroblasts; the P501S-specific activity could be sustained by the continued stimulation of the cultures with P501S-transduced fibroblasts in the presence of IL-15. A panel of HLA-mismatched fibroblast lines transduced with P501S were generated to define the restriction allele of the response. By measuring Interferon-γ in an ELI SPOT assay, the P501S specific response was shown to be restricted by HLA-A2. These results demonstrate that a CD8+ CTL response to P501S can be elicited.

Example 10

Identification of a Naturally Processed CTL Epitope Contained Within a Novel Prostate Tumor Antigen The novel prostate antigen P20, as described above, is also referred to as P703P. The 9-mer peptide, p5, having an amino acid sequence of LLANDLMLI, (SEQ ID NO: 338) was derived from the P703P antigen. The p5 peptide is immunogenic in human HLA-A2 donors and is a naturally processed epitope. Antigen specific CD8+ T cells can be primed following repeated in vitro stimulations with monocytes pulsed with p5 peptide. These CTL specifically recognize p5-pulsed target cells in both ELISPOT (described above), and chromium release assays. Additionally, in HLA-A2 transgenic mice (described above), immunization with p5 leads to the generation of CTL lines which recognize a variety of P703P transduced target cells expressing either HLA-A2Kb or HLA-A2. Specifically, HLA-A2 transgenic mice were immunized subcutaneously in the footpad with 100 ug of p5 peptide formulated together with 140 ug of hepatitis B virus core peptide (a Th peptide) in Freund's incomplete adjuvant. Three weeks post immunization, spleen cells from immunized mice were stimulated in vitro with peptide-pulsed LPS blasts. CTL activity was assessed by chromium release assay five days after primary in vitro stimulation. Retrovirally transduced cells expressing P703P, or control antigen, and HLA-A2Kb were used as targets. CTL lines specifically recognized both p5-pulsed targets as well as P703P-expressing targets have been identified.

Human in vitro priming experiments have been conducted that demonstrate the p5 peptide is immunogenic in humans. Dendritic cells (DC) were differentiated from monocyte cultures derived from PBMC of normal human donors by culturing for five days in RPMI medium containing 10% human serum and 50 ng/ml human GM-CSF and 30 ng/ml human IL-4. Following culture, the DC were pulsed with p5 peptide and cultured with GM-CSF and IL-4 together with CD8+ T cell enriched PBMC. CTL lines were restimulated in a weekly basis using p5-pulsed monocytes in subsequent stimulations. Five to six weeks after initiation of the CTL cultures, CTL recognition of p5-pulsed target cells was demonstrated.

From the foregoing, it will be appreciated that, although specific embodiments of the invention have been described herein for the purposes of illustration, various modifications may be made without deviating from the spirit and scope of the invention. Accordingly, the present invention is not limited except as by the appended claims.

What is claimed is:

1. An isolated polypeptide consisting of SEQ ID NO: 327.

2. An isolated polypeptide encoded by SEQ ID NO:326.

3. The isolated polypeptide of claim 1, said polypeptide being present in a formulation comprising a physiologically acceptable carrier and an adjuvant.

4. An isolated polypeptide effective for eliciting a human T-cell response consisting of the naturally processed HLA-A2 epitope of amino acid residues 78–86 of SEQ ID NO:327, said polypeptide being present in a formulation comprising a physiologically acceptable carrier and an adjuvant.

5. An isolated polypeptide consisting of SEQ ID NO: 327 or a fragment of SEQ ID NO: 327 comprising at least the naturally processed HLA-A2 T-cell epitope of amino acid residues 78–86 of SEQ ID NO: 327, said polypeptide being present in a formulation comprising a physiologically acceptable carrier and an adjuvant.

6. An isolated polypeptide effective for eliciting a human T-cell response, said polypeptide having at least 95% identity to the entirety of SEQ ID NO: 327 and comprising no more than 220 amino acid residues, said polypeptide being present in a formulation comprising a physiologically acceptable carrier and an adjuvant.

* * * * *

SEQUENCE LISTING

<160> NUMBER OF SEQ ID NOS: 338

<210> SEQ ID NO 1
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1

| | | | | | |
|---|---|---|---|---|---|
| tttttttttt | tttttcacag | tataacagct | ctttatttct | gtgagttcta | ctaggaaatc | 60 |
| atcaaatctg | agggttgtct | ggaggacttc | aatacacctc | ccccatagt | gaatcagctt | 120 |
| ccagggggtc | cagtccctct | ccttacttca | tccccatccc | atgccaaagg | aagaccctcc | 180 |
| ctccttggct | cacagccttc | tctaggcttc | ccagtgcctc | caggacagag | tgggttatgt | 240 |
| tttcagctcc | atccttgctg | tgagtgtctg | gtgcgttgtg | cctccagctt | ctgctcagtg | 300 |
| cttcatggac | agtgtccagc | acatgtcact | ctccactctc | tcagtgtgga | tccactagtt | 360 |
| ctagagcggc | cgccaccgcg | gtggagctcc | agcttttgtt | ccctttagtg | agggttaatt | 420 |
| gcgcgcttgg | cgtaatcatg | gtcataactg | tttcctgtgt | gaaattgtta | tccgctcaca | 480 |
| attccacaca | acatacgagc | cggaagcata | aagtgtaaag | cctggggtgc | ctaatgagtg | 540 |
| anctaactca | cattaattgc | gttgcgctca | ctgnccgctt | tccagtcngg | aaaactgtcg | 600 |
| tgccagctgc | attaatgaat | cggccaacgc | ncggggaaaa | gcggtttgcg | ttttgggggc | 660 |
| tcttccgctt | ctcgctcact | nantcctgcg | ctcggtcntt | cggctgcggg | gaacggtatc | 720 |
| actcctcaaa | ggnggtatta | cggttatccn | naaatcnggg | gatacccngg | aaaaaanttt | 780 |
| aacaaagggg | cancaaaggg | cngaaacgta | aaaa | | | 814 |

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2

| | | | | | |
|---|---|---|---|---|---|
| acagaaatgt | tggatggtgg | agcacctttc | tatacgactt | acaggacagc | agatggggaa | 60 |
| ttcatggctg | ttggagcaat | agaacccag | ttctacgagc | tgctgatcaa | aggacttgga | 120 |
| ctaaagtctg | atgaacttcc | caatcagatg | agcatggatg | attggccaga | aatgaagaag | 180 |
| aagtttgcag | atgtatttgc | aaagaagacg | aaggcagagt | ggtgtcaaat | ctttgacggc | 240 |
| acagatgcct | gtgtgactcc | ggttctgact | tttgaggagg | ttgttcatca | tgatcacaac | 300 |
| aaggaacggg | gctcgtttat | caccagtgag | gagcaggacg | tgagccccg | ccctgcacct | 360 |
| ctgctgttaa | acaccccagc | catcccttct | ttcaaaaggg | atccactagt | tctagaagcg | 420 |
| gccgccaccg | cggtggagct | ccagcttttg | ttccctttag | tgagggttaa | ttgcgcgctt | 480 |
| ggcgtaatca | tggtcatagc | tgtttcctgt | gtgaaattgt | tatccgctca | caattccccc | 540 |
| aacatacgag | ccggaacata | aagtgttaag | cctggggtgc | ctaatgantg | agctaactcn | 600 |
| cattaattgc | gttgcgctca | ctgcccgctt | tccagtcggg | aaaactgtcg | tgccactgcn | 660 |
| ttantgaatc | ngccacccc | cgggaaaagg | cggttgcntt | ttgggcctct | tccgctttcc | 720 |

| | |
|---|---|
| tcgctcattg atcctngcnc ccggtcttcg gctgcggnga acggttcact cctcaaaggc | 780 |
| ggtntnccgg ttatccccaa acngggata cccnga | 816 |

<210> SEQ ID NO 3
<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3

| | |
|---|---|
| cttttgaaag aagggatggc tgggtgttt aacagcagag gtgcagggcg ggggctcacg | 60 |
| tcctgctcct cactggtgat aaacgagccc cgttccttgt tgtgatcatg atgaacaacc | 120 |
| tcctcaaaag tcagaaccgg agtcacacag gcatctgtgc cgtcaaagat ttgacaccac | 180 |
| tctgccttcg tcttctttgc aaatacatct gcaaacttct tcttcatttc tggccaatca | 240 |
| tccatgctca tctgattggg aagttcatca gactttagtc canntccttt gatcagcagc | 300 |
| tcgtagaact ggggttctat tgctccaaca gccatgaatt ccccatctgc tgtcctgtaa | 360 |
| gtcgtataga aaggtgctcc accatccaac atgttctgtc ctcgagggg ggcccggtac | 420 |
| ccaattcgcc ctatantgag tcgtattacg cgcgctcact ggccgtcgtt ttacaacgtc | 480 |
| gtgactggga aaaccctggg cgttaccaac ttaatcgcct tgcagcacat cccccttttcg | 540 |
| ccagctgggc gtaatancga aaaggcccgc accgatcgcc cttccaacag ttgcgcacct | 600 |
| gaatgggnaa atgggacccc cctgttaccg cgcattnaac ccccgcnggg tttngttgtt | 660 |
| accccacnt nnaccgctta cactttgcca gcgccttanc gcccgctccc tttcnccttt | 720 |
| cttcccttcc tttcncnccn cttccccg gggtttcccc cntcaaaccc cna | 773 |

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4

| | |
|---|---|
| cctcctgagt cctactgacc tgtgctttct ggtgtggagt ccagggctgc taggaaaagg | 60 |
| aatgggcaga cacaggtgta tgccaatgtt tctgaaatgg gtataatttc gtcctctcct | 120 |
| tcggaacact ggctgtctct gaagacttct cgctcagttt cagtgaggac acacacaaag | 180 |
| acgtgggtga ccatgttgtt tgtggggtgc agagatggga gggtggggc ccaccctgga | 240 |
| agagtggaca gtgacacaag gtggacactc tctacagatc actgaggata agctggagcc | 300 |
| acaatgcatg aggcacacac acagcaagga tgacnctgta aacatagccc acgctgtcct | 360 |
| gnggcactg gaagcctan atnaggccgt gagcanaaag aaggggagga tccactagtt | 420 |
| ctanagcggc cgccaccgcg gtgganctcc anctttgtt ccctttagtg agggttaatt | 480 |
| gcgcgcttgg cntaatcatg gtcatanctn tttcctgtgt gaaattgtta tccgctcaca | 540 |
| attccacaca acatacgagc cggaaacata antgtaaac ctggggtgcc taatgantga | 600 |
| ctaactcaca ttaattgcgt tgcgctcact gcccgctttc caatcnggaa acctgtcttg | 660 |
| ccncttgcat tnatgaatcn gccaacccc ggggaaaagc gtttgcgttt tgggcgctct | 720 |

| | |
|---|---|
| tccgcttcct cnctcantta ntccctncnc tcggtcattc cggctgcngc aaaccggttc | 780 |
| accncctcca aaggggtat tccggtttcc ccnaatccgg gganancc | 828 |

<210> SEQ ID NO 5
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5

| | |
|---|---|
| tttttttttt tttttactga tagatggaat ttattaagct tttcacatgt gatagcacat | 60 |
| agttttaatt gcatccaaag tactaacaaa aactctagca atcaagaatg cagcatgtt | 120 |
| attttataac aatcaacacc tgtggctttt aaaatttggt tttcataaga taatttatac | 180 |
| tgaagtaaat ctagccatgc ttttaaaaaa tgctttaggt cactccaagc ttggcagtta | 240 |
| acatttggca taaacaataa taaaacaatc acaatttaat aaataacaaa tacaacattg | 300 |
| taggccataa tcatatacag tataaggaaa aggtggtagt gttgagtaag cagttattag | 360 |
| aatagaatac cttggcctct atgcaaatat gtctagacac tttgattcac tcagccctga | 420 |
| cattcagttt tcaaagtagg agacaggttc tacagtatca ttttacagtt tccaacacat | 480 |
| tgaaaacaag tagaaaatga tgagttgatt tttattaatg cattacatcc tcaagagtta | 540 |
| tcaccaaccc ctcagttata aaaattttc aagttatatt agtcatataa cttggtgtgc | 600 |
| ttatttttaaa ttagtgctaa atggattaag tgaagacaac aatggtcccc taatgtgatt | 660 |
| gatattggtc atttttacca gcttctaaat ctnaactttc aggcttttga actggaacat | 720 |
| tgnatnacag tgttccanag ttncaaccta ctggaacatt acagtgtgct tgattcaaaa | 780 |
| tgttattttg ttaaaaatta aattttaacc tggtggaaaa ataatttgaa atna | 834 |

<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6

| | |
|---|---|
| tttttttttt tttttttttt aagaccctca tcaatagatg gagacataca gaaatagtca | 60 |
| aaccacatct acaaaatgcc agtatcaggc ggcggcttcg aagccaaagt gatgtttgga | 120 |
| tgtaaagtga atattagtt ggcggatgaa gcagatagtg aggaaagttg agccaataat | 180 |
| gacgtgaagt ccgtggaagc ctgtggctac aaaaaatgtt gagccgtaga tgccgtcgga | 240 |
| aatggtgaag ggagactcga agtactctga ggcttgtagg agggtaaaat agagacccag | 300 |
| taaaattgta ataagcagtg cttgaattat ttggtttcgg ttgttttcta ttagactatg | 360 |
| gtgagctcag gtgattgata ctcctgatgc gagtaatacg gatgtgttta ggagtgggac | 420 |
| ttctagggga tttagcgggg tgatgcctgt tgggggccag tgccctccta gttgggggt | 480 |
| aggggctagg ctggagtggt aaaaggctca gaaaaatcct gcgaagaaaa aaacttctga | 540 |
| ggtaataaat aggattatcc cgtatcgaag gccttttggg acaggtggtg tgtggtggcc | 600 |
| ttggtatgtg ctttctcgtg ttacatcgcg ccatcattgg tatatggtta gtgtgttggg | 660 |
| ttantanggc ctantatgaa gaacttttgg antggaatta aatcaatngc ttggccggaa | 720 |

| | |
|---|---|
| gtcattanga nggctnaaaa ggccctgtta ngggtctggg ctnggtttta cccnacccat | 780 |
| ggaatncncc ccccggacna ntgnatccct attcttaa | 818 |

<210> SEQ ID NO 7
<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7

| | |
|---|---|
| tttttttttt tttttttttt tggctctaga gggggtagag ggggtgctat agggtaaata | 60 |
| cgggccctat ttcaaagatt tttagggaa ttaattctag gacgatgggt atgaaactgt | 120 |
| ggtttgctcc acagatttca gagcattgac cgtagtatac cccggtcgt gtagcggtga | 180 |
| aagtggtttg gtttagacgt ccgggaattg catctgtttt taagcctaat gtggggacag | 240 |
| ctcatgagtg caagacgtct tgtgatgtaa ttattatacn aatgggggct tcaatcggga | 300 |
| gtactactcg attgtcaacg tcaaggagtc gcaggtcgcc tggttctagg aataatgggg | 360 |
| gaagtatgta ggaattgaag attaatccgc cgtagtcggt gttctcctag gttcaatacc | 420 |
| attggtggcc aattgatttg atggtaaggg gagggatcgt tgaactcgtc tgttatgtaa | 480 |
| aggatncctt ngggatggga aggcnataa ggactangga tnaatggcgg gcangatatt | 540 |
| tcaaacngtc tctanttcct gaaacgtctg aaatgttaat aanaattaan tttngttatt | 600 |
| gaatnttnng gaaaagggct tacaggacta gaaaccaaat angaaaanta atnntaanggg | 660 |
| cnttatcntn aaaggtnata accnctccta tnatcccacc caatngnatt ccccacncnn | 720 |
| acnattggat nccccanttc canaaanggc cnccccccgg tgnanncnc cttttgttcc | 780 |
| cttnantgan ggttattcnc ccctngcntt atcancc | 817 |

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8

| | |
|---|---|
| catttccggg tttactttct aaggaaagcc gagcggaagc tgctaacgtg ggaatcggtg | 60 |
| cataaggaga actttctgct ggcacgcgct agggacaagc gggagagcga ctccgagcgt | 120 |
| ctgaagcgca cgtcccagaa ggtggacttg cactgaaaac agctgggaca catccgcgag | 180 |
| tacgaacagc gcctgaaagt gctggagcgg gaggtccagc agtgtagccg cgtcctgggg | 240 |
| tgggtggccg angcctganc cgctctgcct tgctgccccc angtgggccg ccaccccctg | 300 |
| acctgcctgg gtccaaacac tgagccctgc tggcggactt caaggaaaac ccccacanggg | 360 |
| ggattttgct cctanantaa ggctcatctg ggcctcggcc ccccaccctg gttggccttg | 420 |
| tctttgangt gagccccatg tccatctggg ccactgtcng gaccacctttt ngggagtgtt | 480 |
| ctccttacaa ccacannatg cccggctcct cccggaaacc antccancc tgngaaggat | 540 |
| caagncctgn atccactnnt nctanaaccg gccnccnccg cngtgaacc cnccttntgt | 600 |
| tcctttttcnt tnagggttaa tnncgccttg gccttnccan ngtcctncnc ntttttccnnt | 660 |

```
gttnaaattg ttangcnccc nccnntcccn cnncnncnan cccgacccnn anntnnann      720 ncctgggggt nccnncngat tgacccnncc ncccntntant tgcnttnggg nncnntgccc    780
ctttccctct ngggaanncg                                                799

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9
acgccttgat cctcccaggc tgggactggt tctgggagga gccgggcatg ctgtggtttg     60
taangatgac actcccaaag gtggtcctga cagtggccca gatggacatg gggctcacct   120
caaggacaag gccaccaggt gcgggggccg aagcccacat gatccttact ctatgagcaa   180
aatcccctgt gggggcttct ccttgaagtc cgccancagg gctcagtctt tggacccang   240
caggtcatgg ggttgtngnc caactggggg ccncaacgca aaanggcnca gggcctcngn   300
cacccatccc angacgcggc tacactnctg gacctcccnc tccaccactt tcatgcgctg   360
ttcntacccg cgnatntgtc ccanctgttt cngtgccnac tccancttct nggacgtgcg   420
ctacatacgc ccggantcnc nctcccgctt tgtccctatc cacgtnccan caacaaattt   480
cnccntantg caccnattcc cacntttnnc agntttccnc nncgngcttc cttntaaaag   540 ggttgancccc cggaaaatnc cccaagggg ggggccngg tacccaactn cccctnata    600 gctgaantcc ccatnaccnn gnctcnatgg anccntcct tttaannacn ttctnaactt   660
gggaanancc ctcgnccntn ccccnttaa tcccnccttg cnangnncnt ccccnntcc    720 ncccnnntng gcntntnann caaaaaggc ccnnnancaa tctcctnncn cctcanttcg   780
ccanccctcg aaatcggccn c                                             801

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10
cagtctatnt ggccagtgtg gcagctttcc ctgtggctgc cggtgccaca tgcctgtccc     60
acagtgtggc cgtggtgaca gcttcagccg ccctcaccgg gttcaccttc tcagccctgc   120
agatcctgcc ctacacactg gcctccctct accaccggga gaagcaggtg ttcctgccca   180
aataccgagg ggacactgga ggtgctagca gtgaggacag cctgatgacc agcttcctgc   240
caggccctaa gcctggagct cccttcccta atggacacgt gggtgctgga ggcagtggcc   300
tgctcccacc tccaccgcg ctctgcgggg cctctgcctg tgatgtctcc gtacgtgtgg   360
tggtgggtga gccaccgan gccagggtgg ttccggccg gggcatctgc ctggacctcg   420
ccatcctgga tagtgcttcc tgctgtccca ngtggcccca tccctgttta tgggctccat   480
tgtccagctc agccagtctg tcactgccta tatggtgtct gccgcaggcc tgggtctggt   540
cccatttact ttgctacaca ggtantattt gacaagaacg anttggccaa atactcagcg   600
ttaaaaaatt ccagcaacat tgggggtgga aggcctgcct cactgggtcc aactccccgc   660
```

```
tcctgttaac cccatggggc tgccggcttg ccgccaatt tctgttgctg ccaaantnat      720
gtggctctct gctgccacct gttgctggct gaagtgcnta cngcncanct nggggggtng      780 ggngttccc                                                              789
```

<210> SEQ ID NO 11
<211> LENGTH: 772
<212> TYPE: DNA
<213> ORGANISM: Homo sapien
<220> FEATURE:
<221> NAME/KEY: misc_feature
<222> LOCATION: (1)...(772)
<223> OTHER INFORMATION: n = A,T,C or G

<400> SEQUENCE: 11

```
cccaccctac ccaaatatta gacaccaaca cagaaaagct agcaatggat tcccttctac       60
tttgttaaat aataagtta aatatttaaa tgcctgtgtc tctgtgatgg caacagaagg      120
accaacaggc cacatcctga taaaggtaa gagggggtg gatcagcaaa agacagtgc       180 tgtgggctga ggggacctgg ttcttgtgtg ttgcccctca ggactcttcc cctacaaata      240
actttcatat gttcaaatcc catggaggag tgtttcatcc tagaaactcc catgcaagag      300
ctacattaaa cgaagctgca ggttaagggg cttanagatg gaaaccagg tgactgagtt      360 tattcagctc ccaaaaaccc ttctctaggt gtgtctcaac taggaggcta gctgttaacc      420
ctgagcctgg gtaatccacc tgcagagtcc ccgcattcca gtgcatggaa cccttctggc      480
ctccctgtat aagtccagac tgaaaccccc ttggaaggnc tccagtcagg cagccctana      540
aactggggaa aaaagaaaag gacgccccan ccccagctg tgcanctacg cacctcaaca      600
gcacagggtg gcagcaaaaa aaccacttta ctttggcaca acaaaaact nggggggca       660 accccggcac cccnanggg gttaacagga ancngggnaa cntggaaccc aattnaggca      720
ggcccnccac cccnaatntt gctgggaaat ttttcctccc ctaaattntt tc             772
```

<210> SEQ ID NO 12
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 12

```
gccccaattc cagctgccac accacccacg gtgactgcat tagttcggat gtcatacaaa       60
agctgattga agcaaccctc tacttttgg tcgtgagcct tttgcttggt gcaggtttca      120
ttggctgtgt tggtgacgtt gtcattgcaa cagaatgggg gaaaggcact gttctctttg      180
aagtanggtg agtcctcaaa atccgtatag ttggtgaagc cacagcactt gagccctttc      240
atggtggtgt tccacacttg agtgaagtct tcctgggaac cataatcttt cttgatggca      300
ggcactacca gcaacgtcag ggaagtgctc agccattgtg gtgtacacca aggcgaccac      360
agcagctgcn acctcagcaa tgaagatgan gaggangatg aagaagaacg tcncgagggc      420
acacttgctc tcagtcttan caccatanca gcccntgaaa accaananca aagaccacna      480
cnccggctgc gatgaagaaa tnaccccncg ttgacaaact tgcatggcac tgggnaccac      540
agtgccccna aaaatcttca aaaggatgc cccatcnatt gacccccaa atgcccactg       600 ccaacagggg ctgccccacn cncnnaacga tganccnatt gnacaagatc tncntggtct      660
```

-continued

```
tnatnaacnt gaaccctgcn tngtggctcc tgttcaggnc cnnggcctga cttctnaann    720
aangaactcn gaagncccca cngganannc g                                   751

<210> SEQ ID NO 13
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13
gagccaggcg tccctctgcc tgcccactca gtggcaacac ccgggagctg ttttgtcctt     60
tgtggancct cagcagtncc ctctttcaga actcantgcc aagancctg aacaggagcc     120 accatgcagt gcttcagctt cattaagacc atgatgatcc tcttcaattt gctcatcttt    180
ctgtgtggtg cagccctgtt ggcagtgggc atctgggtgt caatcgatgg ggcatccttt    240
ctgaagatct tcgggccact gtcgtccagt gccatgcagt ttgtcaacgt gggctacttc    300
ctcatcgcag ccggcgttgt ggtcttagct ctaggtttcc tgggctgcta tggtgctaag    360
actgagagca gtgtgccct cgtgacgttc ttcttcatcc tcctcctcat cttcattgct     420
gaggttgcaa tgctgtggtc gccttggtgt acaccacaat ggctgagcac ttcctgacgt    480
tgctggtaat gcctgccatc aanaaaagat tatgggttcc caggaanact tcactcaagt    540
gttggaacac caccatgaaa gggctcaagt gctgtggctt cnnccaacta tacggatttt    600
gaagantcac ctacttcaaa gaaaanagtg cctttccccc atttctgttg caattgacaa    660
acgtccccaa cacagccaat tgaaaacctg cacccaaccc aaagggtcc ccaaccanaa     720 attnaaggg                                                            729

<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14
tgctcttcct caaagttgtt cttgttgcca taacaaccac cataggtaaa gcgggcgcag     60
tgttcgctga aggggttgta gtaccagcgc gggatgctct ccttgcagag tcctgtgtct    120
ggcaggtcca cgcagtgccc tttgtcactg gggaaatgga tgcgctggag ctcgtcaaag    180
ccactcgtgt atttttcaca ggcagcctcg tccgacgcgt cggggcagtt gggggtgtct    240
tcacactcca ggaaactgtc natgcagcag ccattgctgc agcggaactg ggtgggctga    300
cangtgccag agcacactgg atggcgcctt tccatgnnan gggccctgng ggaaagtccc    360
tganccccan anctgcctct caaangcccc accttgcaca cccgacagg ctagaatgga     420 atcttcttcc cgaaaggtag ttnttcttgt tgcccaancc anccccntaa acaaactctt    480
gcanatctgc tccgnggggg tcntantacc ancgtgggaa aagaacccca ggcngcgaac    540
caancttgtt tggatncgaa gcnataatct nctnttctgc ttggtggaca gcaccantna    600
ctgtnnanct ttagnccntg gtcctcntgg gttgnncttg aacctaatcn ccnntcaact    660
gggacaaggt aantngccnt cctttnaatt cccnancntn cccctggtt tggggttttn     720 cncnctccta ccccagaaan nccgtgttcc cccccaacta ggggccnaaa ccnttnttc     780
```

```
cacaaccctn ccccacccac gggttcngnt ggttng                              816
```

<210> SEQ ID NO 15
<211> LENGTH: 783
<212> TYPE: DNA
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15

```
ccaaggcctg ggcaggcata nacttgaagg tacaacccca ggaaccctg gtgctgaagg     60
atgtggaaaa cacagattgg cgcctactgc ggggtgacac ggatgtcagg gtagagagga   120
aagacccaaa ccaggtggaa ctgtggggac tcaaggaang cacctacctg ttccagctga   180
cagtgactag ctcagaccac ccagaggaca cggccaacgt cacagtcact gtgctgtcca   240
ccaagcagac agaagactac tgcctcgcat ccaacaangt gggtcgctgc cggggctctt   300
tcccacgctg gtactatgac cccacggagc agatctgcaa gagtttcgtt tatggaggct   360
gcttgggcaa caagaacaac taccttcggg aagaagagtg cattctancc tgtcngggtg   420
tgcaaggtgg gcctttgana ngcanctctg gggctcangc gactttcccc cagggcccct   480
ccatggaaag gcgccatcca ntgttctctg gcacctgtca gcccacccag ttccgctgca   540
ncaatggctg ctgcatcnac antttcctng aattgtgaca acaccccca ntgccccaa    600
ccctcccaac aaagcttccc tgttnaaaaa tacnccantt ggcttttnac aaacnccgg   660
cnccctccntt ttccccnntn aacaaagggc nctngcnttt gaactgcccn aaccnggaa   720
tctnccnngg aaaaantncc ccccctggtt cctnnaancc cctccncnaa anctnccccc  780
ccc                                                                 783
```

<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16

```
gccccaattc cagctgccac accacccacg gtgactgcat tagttcggat gtcatacaaa    60
agctgattga agcaaccctc tacttttttgg tcgtgagcct tttgcttggt gcaggtttca   120
ttggctgtgt tggtgacgtt gtcattgcaa cagaatgggg gaaaggcact gttctctttg   180
aagtagggtg agtcctcaaa atccgtatag ttggtgaagc cacagcactt gagccctttc   240
atggtggtgt tccacacttg agtgaagtct tcctgggaac cataatcttt cttgatggca   300
ggcactacca gcaacgtcag gaagtgctca gccattgtgg tgtacaccaa ggcgaccaca   360
gcagctgcaa cctcagcaat gaagatgagg aggaggatga agaagaacgt cncgagggca   420
cacttgctct ccgtcttagc accatagcag cccangaaac caagagcaaa gaccacaacg   480
ccngctgcga atgaaagaaa ntacccacgt tgacaaactg catggccact ggacgacagt   540
tggcccgaan atcttcagaa aagggatgcc ccatcgattg aacacccana tgcccactgc   600
cnacagggct gcnccncncn gaaagaatga gccattgaag aaggatcntc ntggtcttaa   660
tgaactgaaa ccntgcatgg tggcccctgt tcagggctct tggcagtgaa ttctganaaa   720
```

| | |
|---|---|
| aaggaacngc ntnagccccc ccaaangana aaacaccccc gggtgttgcc ctgaattggc | 780 |
| ggccaaggan ccctgccccn g | 801 |

<210> SEQ ID NO 17
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17

| | |
|---|---|
| gtgagagcca ggcgtccctc tgcctgccca ctcagtggca cacccggga gctgttttgt | 60 |
| cctttgtgga gcctcagcag ttccctcttt cagaactcac tgccaagagc cctgaacagg | 120 |
| agccaccatg cagtgcttca gcttcattaa gaccatgatg atcctcttca atttgctcat | 180 |
| cttttctgtgt ggtgcagccc tgttggcagt gggcatctgg gtgtcaatcg atgggcatc | 240 |
| ctttctgaag atcttcgggc cactgtcgtc cagtgccatg cagtttgtca cgtgggcta | 300 |
| cttcctcatc gcagccggcg ttgtggtctt tgctcttggt ttcctgggct gctatggtgc | 360 |
| taagacggag agcaagtgtg ccctcgtgac gttcttcttc atcctcctcc tcatcttcat | 420 |
| tgctgaagtt gcagctgctg tggtcgcctt ggtgtacacc acaatggctg aaccattcct | 480 |
| gacgttgctg gtantgcctg ccatcaanaa agattatggg ttcccaggaa aaattcactc | 540 |
| aantntggaa caccnccatg aaaagggctc caatttctgn tggcttcccc aactataccg | 600 |
| gaattttgaa agantcnccc tacttccaaa aaaaaanant tgcctttncc cccnttctgt | 660 |
| tgcaatgaaa acntcccaan acngccaatn aaaacctgcc cnnncaaaaa ggntcncaaa | 720 |
| caaaaaaant nnaagggttn | 740 |

<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18

| | |
|---|---|
| ccgctggttg cgctggtcca gngnagccac gaagcacgtc agcatacaca gcctcaatca | 60 |
| caaggtcttc cagctgccgc acattacgca gggcaagagc ctccagcaac actgcatatg | 120 |
| ggatacactt tactttagca gccagggtga caactgagag gtgtcgaagc ttattcttct | 180 |
| gagcctctgt tagtggagga agattccggg cttcagctaa gtagtcagcg tatgtcccat | 240 |
| aagcaaacac tgtgagcagc cggaaggtag aggcaaagtc actctcagcc agctctctaa | 300 |
| cattgggcat gtccagcagt tctccaaaca cgtagacacc agnggcctcc agcacctgat | 360 |
| ggatgagtgt ggccagcgct gccccttgg ccgacttggc taggagcaga aattgctcct | 420 |
| ggttctgccc tgtcaccttc acttccgcac tcatcactgc actgagtgtg ggggacttgg | 480 |
| gctcaggatg tccagagacg tggttccgcc ccctcnctta atgacaccgn ccanncaacc | 540 |
| gtcggctccc gccgantgng ttcgtcgtnc ctgggtcagg gtctgctggc cnctacttgc | 600 |
| aancttcgtc nggcccatgg aattcaccnc accggaactn gtangatcca ctnnttctat | 660 |
| aaccggncgc caccgcnnnt ggaactccac tcttnttncc tttacttgag ggttaaggtc | 720 |
| acccttnncg ttaccttggt ccaaaccntn ccntgtgtcg anatngtnaa tcnggnccna | 780 |

| | |
|---|---:|
| tnccanccnc atangaagcc ng | 802 |

<210> SEQ ID NO 19
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19

| | | | | | |
|---|---|---|---|---|---:|
| cnaagcttcc | aggtnacggg | ccgcnaancc | tgacccnagg | tancanaang | cagncngcgg | 60 |
| gagcccaccg | tcacgnggng | gngtctttat | nggaggggc | ggagccacat | cnctggacnt | 120 |
| cntgacccca | actccccncc | ncncantgca | gtgatgagtg | cagaactgaa | ggtnacgtgg | 180 |
| caggaaccaa | gancaaannc | tgctccnntc | caagtcggcn | naggggggcgg | ggctggccac | 240 |
| gcncatcct | cnagtgctgn | aaagccccnn | cctgtctact | tgtttggaga | acngcnnnga | 300 |
| catgcccagn | gttanataac | nggcngagag | tnantttgcc | tctcccttcc | ggctgcgcan | 360 |
| cgngtntgct | tagnggacat | aacctgacta | cttaactgaa | cccnngaatc | tnccnccct | 420 |
| ccactaagct | cagaacaaaa | aacttcgaca | ccactcantt | gtcacctgnc | tgctcaagta | 480 |
| aagtgtaccc | catnccaat | gtntgctnga | ngctctgncc | tgcnttangt | tcggtcctgg | 540 |
| gaagacctat | caattnaagc | tatgtttctg | actgcctctt | gctccctgna | acaancnacc | 600 |
| cnncnntcca | aggggggnc | ggcccccaat | ccccccaacc | ntnaattnan | tttanccccn | 660 |
| ccccccggcc | cggcctttta | cnancntcnn | nnacnggna | aaaccnnngc | tttncccaac | 720 |
| nnaatccncc t | | | | | | 731 |

<210> SEQ ID NO 20
<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20

| | | | | | |
|---|---|---|---|---|---:|
| ttttttttt | tttttttttt | taaaaacccc | ctccattnaa | tgnaaacttc | cgaaattgtc | 60 |
| caaccccctc | ntccaaatnn | ccntttccgg | gnggggttc | caaacccaan | ttannttgg | 120 |
| annttaaatt | aaatnttnnt | tggnggnnna | anccnaatgt | nangaaagtt | naaccanta | 180 |
| tnancttnaa | tncctggaaa | ccgtngntt | ccaaaaatnt | ttaaccctta | antccctccg | 240 |
| aaatngttna | nggaaaaccc | aanttctcnt | aaggttgttt | gaaggntnaa | tnaaaanccc | 300 |
| nnccaattgt | ttttngccac | gcctgaatta | attggnttcc | gntgttttcc | nttaaaanaa | 360 |
| ggnnancccc | ggttantnaa | tccccccnnc | cccaattata | ccganttttt | ttngaattgg | 420 |
| ganccncgg | gaattaacgg | ggnnnntccc | tnttgggggg | cnggnncccc | ccccntcggg | 480 |
| ggttngggnc | aggncnnaat | tgtttaaggg | tccgaaaaat | ccctccnaga | aaaaaanctc | 540 |
| ccaggntgag | nnttngggttt | ncccccccc | canggcccct | ctcgnanagt | tggggtttgg | 600 |
| ggggcctggg | atttnttc | ccctnttncc | tccccccccc | ccnggganag | aggttngngt | 660 |
| tttgntcnnc | ggcccncon | aaganctttt | ccganttnan | ttaaatccnt | gcctnggcga | 720 |
| agtccnttgn | agggntaaan | ggcccccctnn | cggg | | | 754 |

-continued

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21

| | | | | | |
|---|---|---|---|---|---|
| atcancccat | gacccnaac | nngggaccnc | tcanccggnc | nnncnaccnc | cggccnatca | 60 |
| nngtnagnnc | actncnnttn | natcacnccc | cnccnactac | gcccncnanc | cnacgcncta | 120 |
| nncanatncc | actganngcg | cgangtngan | ngagaaanct | nataccanag | ncaccanacn | 180 |
| ccagctgtcc | nanaangcct | nnnatacngg | nnnatccaat | ntgnaccctc | cnaagtattn | 240 |
| nncnncanat | gattttcctn | anccgattac | ccntnccccc | tancccctcc | cccccaacna | 300 |
| cgaaggcnct | ggnccnaagg | nngcgncncc | ccgctagntc | cccnncaagt | cncncnccta | 360 |
| aactcanccn | nattacncgc | ttcntgagta | tcactcccg | aatctcaccc | tactcaactc | 420 |
| aaaaanatcn | gatacaaaat | aatncaagcc | tgnttatnac | actntgactg | ggtctctatt | 480 |
| ttagnggtcc | ntnaancntc | ctaatacttc | cagtctncct | tcnccaattt | ccnaanggct | 540 |
| ctttcngaca | gcatntttg | gttcccnntt | gggttcttan | ngaattgccc | ttcntngaac | 600 |
| gggctcntct | tttccttcgg | ttancctggn | ttcnnccggc | cagttattat | ttcccntttt | 660 |
| aaattcntnc | cntttantttt | tggcnttcna | accccccggc | cttgaaaacg | gcccctggt | 720 |
| aaaaggttgt | tttganaaaa | tttttgtttt | gttcc | | | 755 |

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22

| | | | | | |
|---|---|---|---|---|---|
| tttttttttt | tttttangtg | tngtcgtgca | ggtagaggct | tactacaant | gtgaanacgt | 60 |
| acgctnggan | taangcgacc | cganttctag | gannncccct | aaaatcanac | tgtgaagatn | 120 |
| atcctgnnna | cggaanggtc | accggnngat | nntgctaggg | tgnccnctcc | cannncnttn | 180 |
| cataactcng | nggccctgcc | caccaccttc | ggcggcccng | ngnccgggcc | cgggtcattn | 240 |
| gnnttaaccn | cactnngcna | ncggtttccn | nccccnncg | accnggcga | tccgggtnc | 300 |
| tctgtcttcc | cctgnagncn | anaaantggg | ccncggnccc | ctttacccct | nnacaagcca | 360 |
| cngccntcta | nccncngccc | ccctccant | nnggggact | gccnanngct | ccgttnctng | 420 |
| nnaccccnnn | gggtncctcg | gttgtcgant | cnaccgnang | ccanggattc | cnaaggaagg | 480 |
| tgcgttnttg | gccctaccc | ttcgctncgg | nncacccttc | ccgacnanga | nccgctcccg | 540 |
| cncnncgnng | cctcncctcg | caacacccgc | nctcntcngt | ncggnnnccc | ccccacccgc | 600 |
| ncccctcncnc | ngncgnancn | ctccnccncc | gtctcannca | ccaccccgcc | ccgccaggcc | 660 |
| ntcanccacn | ggnngacnng | nagcncnntc | gcnccgcgcn | gcgncnccct | cgccncngaa | 720 |
| ctncntcngg | ccantnncgc | tcaanccnna | cnaaacgccg | ctgcgcggcc | cgnagcgncc | 780 |
| ncctccncga | gtcctcccgn | cttccnaccc | angnnttccn | cgaggacacn | nnaccccgcc | 840 |
| nncangcgg | | | | | | 849 |

<210> SEQ ID NO 23
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 23

| | | | | | |
|---|---|---|---|---|---|
| gcgcaaacta | tacttcgctc | gnactcgtgc | gcctcgctnc | tcttttcctc | cgcaaccatg | 60 |
| tctgacnanc | ccgattnggc | ngatatcnan | aagntcganc | agtccaaact | gantaacaca | 120 |
| cacacncnan | aganaaatcc | nctgccttcc | anagtanacn | attgaacnng | agaaccangc | 180 |
| nggcgaatcg | taatnaggcg | tgcgccgcca | atntgtcncc | gtttattntn | ccagcntcnc | 240 |
| ctnccnaccc | tacntcttcn | nagctgtcnn | accccctngtn | cgnaccccc | naggtcggga | 300 |
| tcgggttnn | nntgaccgng | cnncccctcc | cccntccat | nacgancnc | ccgcaccacc | 360 |
| nanngcncgc | ncccgnnct | cttcgccncc | ctgtcctntn | ccctgtngc | ctggcncngn | 420 |
| accgcattga | ccctcgccnn | ctncnngaaa | ncgnanacgt | ccgggttgnn | annancgctg | 480 |
| tgggnnngcg | tctgcnccgc | gttccttccn | ncnncttcca | ccatcttcnt | tacngggtct | 540 |
| ccncgccntc | tcnnncacnc | cctgggacgc | tntcctntgc | cccccttnac | tccccccctt | 600 |
| cgncgtgncc | cgnccccacc | ntcatttnca | nacgntcttc | acaannncct | ggntnnctcc | 660 |
| cnancngncn | gtcanccnag | ggaagggngg | ggnncnntg | nttgacgttg | nggngangtc | 720 |
| cgaanantcc | tcnccntcan | cnctaccct | cgggcgnnct | ctcngttncc | aacttancaa | 780 |
| ntctcccccg | ngngcncntc | tcagcctcnc | ccnccccnct | ctctgcantg | tnctctgctc | 840 |
| tnaccnntac | gantnttcgn | cnccctcttt | cc | | | 872 |

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24

| | | | | | |
|---|---|---|---|---|---|
| gcatgcaagc | ttgagtattc | tatagngtca | cctaaatanc | ttggcntaat | catggtcnta | 60 |
| nctgncttcc | tgtgtcaaat | gtatacnaan | tanatatgaa | tctnatntga | caagannta | 120 |
| tcntncatta | gtaacaantg | tnntgtccat | cctgtcngan | canattccca | tnnattncgn | 180 |
| cgcattcncn | gcncantatn | taatngggaa | ntcnnntnnn | ncaccnncat | ctatcntncc | 240 |
| gcnccctgac | tggnagagat | ggatnanttc | tnntntgacc | nacatgttca | tcttggattn | 300 |
| aananccccc | cgcngnccac | cggttngnng | cnagccnntc | ccaagacctc | ctgtggaggt | 360 |
| aacctgcgtc | aganncatca | aacntgggaa | acccgcnncc | angtnnaagt | ngnnncanan | 420 |
| gatcccgtcc | aggnttnacc | atcccttcnc | agcgcccct | ttngtgcctt | anagngnagc | 480 |
| gtgtccnanc | cnctcaacat | ganacgcgcc | agnccanccg | caattnggca | caatgtcgnc | 540 |
| gaaccccta | ggggantna | tncaaanccc | caggattgtc | cncncangaa | atcccncanc | 600 |
| ccncccctac | ccnnctttgg | gacngtgacc | aantcccgga | gtccagtcc | ggccngnctc | 660 |
| ccccaccggt | nnccntgggg | gggtgaanct | cngnntcanc | cngncgaggn | ntcgnaagga | 720 |

| | |
|---|---|
| accggncctn ggncgaanng ancnntcnga agngccncnt cgtataaccc cccctcncca | 780 |
| nccnacngnt agntcccccc cngggtncgg aangg | 815 |

<210> SEQ ID NO 25
<211> LENGTH: 775
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25

| | |
|---|---|
| ccgagatgtc tcgctccgtg gccttagctg tgctcgcgct actctctctt tctggcctgg | 60 |
| aggctatcca gcgtactcca aagattcagg tttactcacg tcatccagca gagaatggaa | 120 |
| agtcaaattt cctgaattgc tatgtgtctg ggtttcatcc atccgacatt gaanttgact | 180 |
| tactgaagaa tgganagaga attgaaaaag tggagcattc agacttgtct ttcagcaagg | 240 |
| actggtcttt ctatctcntg tactacactg aattcacccc cactgaaaaa gatgagtatg | 300 |
| cctgccgtgt gaaccatgtg actttgtcac agcccaagat agttaagtgg gatcgagaca | 360 |
| tgtaagcagn cnncatggaa gtttgaagat gccgcatttg gattggatga attccaaatt | 420 |
| ctgcttgctt gcnttttaat antgatatgc ntatacaccc tacccttat gnccccaaat | 480 |
| tgtaggggtt acatnantgt tcncntngga catgatcttc ctttataant ccnccnttcg | 540 |
| aattgcccgt cnccngttn ngaatgtttc cnnaaccacg gttggctccc ccaggtcncc | 600 |
| tcttacggaa gggcctgggc cnctttncaa ggttggggga accnaaaatt tcncttntgc | 660 |
| ccnccncca cnntcttgng nncncantt ggaacccttc cnattcccct tggcctcnna | 720 |
| nccttnncta anaaaacttn aaancgtngc naaannttn acttcccccc ttacc | 775 |

<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26

| | |
|---|---|
| anattantac agtgtaatct tttcccagag gtgtgtanag ggaacggggc ctagaggcat | 60 |
| cccanagata ncttatanca acagtgcttt gaccaagagc tgctgggcac atttcctgca | 120 |
| gaaaggtgg cggtccccat cactcctcct ctcccatagc catcccagag gggtgagtag | 180 |
| ccatcangcc ttcggtggga gggagtcang gaaacaacan accacagagc anacagacca | 240 |
| ntgatgacca tgggcgggag cgagcctctt ccctgnaccg gggtggcana nganagccta | 300 |
| nctgagggt cacactataa acgttaacga ccnagatnan cacctgcttc aagtgcaccc | 360 |
| ttcctacctg acnaccagng accnnnaact gcngcctggg dacagnctg ggancagcta | 420 |
| acnnagcact cacctgcccc cccatggccg tncgcntccc tggtcctgnc aagggaagct | 480 |
| ccctgttgga attncgggga naccaaggga nccccctcct ccanctgtga aggaaaaann | 540 |
| gatggaattt tncccttccg gccnntcccc tcttcctta cacgccccct nntactcntc | 600 |
| tccctctntt ntcctgncnc acttttnacc ccnnnattc ccttnattga tcggannctn | 660 |
| ganattccac tnncgcctnc cntcnatcng naanacnaaa nactntctna cccngggat | 720 |
| gggnncctcg ntcatcctct cttttcnct accnccnntt ctttgcctct ccttngatca | 780 | ccaaccntc gntggccntn ccccccnnn tcctttnccc        820

<210> SEQ ID NO 27
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27
tctgggtgat ggcctcttcc tcctcaggga cctctgactg ctctgggcca agaatctct        60
tgtttcttct ccgagcccca ggcagcggtg attcagccct gcccaacctg attctgatga        120
ctgcggatgc tgtgacggac ccaaggggca aatagggtcc caggtccag ggaggggcgc        180
ctgctgagca cttccgcccc tcaccctgcc cagcccctgc catgagctct gggctgggtc        240
tccgcctcca gggttctgct cttccangca ngccancaag tggcgctggg ccacactggc        300
ttcttcctgc cccntccctg gctctgantc tctgtcttcc tgtcctgtgc angcnccttg        360
gatctcagtt tccctcnctc anngaactct gtttctgann tcttcantta actntganttt       420
tatnaccnan tggnctgtnc tgtcnnactt taatgggccn gaccggctaa tccctccctc        480
nctcccttcc anttcnnnna accngcttnc cntcntctcc ccntancccg ccngggaanc        540
ctcctttgcc ctnaccangg gccnnnaccg cccntnnctn gggggggcnng gtnnctcncc        600
ctgntnnccc cnctcncnnt tncctcgtcc cnncnncgcn nngcannttc ncgtcccnn        660
tnnctcttcn ngtntcgnaa ngtcncntn tnnnnngncn ngtnnntncn tccctctcnc        720
cnnntgnang tnnttnnnnc ncngnnccc nnnncnnnnn nggnnntnnn tctncncngc        780
cccnnccccc ngnattaagg cctccnntct ccggccnc            818

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28
aggaagggcg gagggatatt gtangggatt gagggatagg agnataangg gggaggtgtg        60
tcccaacatg anggtgnngt tctcttttga angagggttg ngtttttann ccnggtgggt        120
gattnaaccc cattgtatgg agnnaaaggn tttnagggat ttttcggctc ttatcagtat        180
ntanattcct gtnaatcgga aaatnatntt tcnncnggaa aatnttgctc ccatccgnaa       240
attnctcccg ggtagtgcat nttnggggn cngccangtt tcccaggctg ctanaatcgt        300
actaaagntt naagtgggan tncaaatgaa aacctnncac agagnatccn tacccgactg        360
tnnnttncct tcgccctntg actctgcnng agcccaatac ccnngngnat gtcnccngn        420
nnngcgncnc tgaaannnnc tcgnggctnn gancatcang gggtttcgca tcaaaagcnn        480
cgtttcncat naaggcactt tngcctcatc caacncctng ccctcnncca tttngccgtc        540
nggttcncct acgctnnntg cncctnnntn ganattttnc ccgcctnggg naancctcct        600
gnaatgggta gggncttntc ttttnaccnn gnggtnact aatcnnctnc acgcntnctt        660
tctcnacccc ccccctttt caatcccanc ggcnaatggg gtctccccnn cgangggggg        720

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

```
actagtccag tgtggtggaa ttccattgtg ttggggncnc ttctatgant antnttagat    60
cgctcanacc tcacanccte ccnacnangc ctataangaa nannaataga nctgtncnnt   120
atntntacnc tcatanncct cnnnacccac tccctcttaa cccntactgt gcctatngcn   180
tnnctantct ntgccgcctn cnanccaccn gtgggccnac cncnngnatt ctcnatctcc   240
tcnccatntn gcctananta ngtncatacc ctatacctac nccaatgcta nnnctaancn   300
tccatnantt annntaacta ccactgacnt ngactttcnc atnanctcct aatttgaatc   360
tactctgact cccacngcct annnattagc ancntccccc nacnatntct caaccaaatc   420
ntcaacaacc tatctanctg ttcnccaacc nttncctccg atcccnnac aaccccctc    480
ccaaataccc nccacctgac ncctaacccn caccatcccg gcaagccnan ggncatttan   540
ccactggaat cacnatngga naaaaaaaac ccnaactctc tancncnnat ctccctaana   600
aatnctcctn naatttactn ncantnccat caancccacn tgaaacnnaa ccccctgtttt  660
tanatccctt ctttcgaaaa ccnacccttt annncccaac ctttngggcc ccccncctnc   720
ccnaatgaag gncncccaat cnagaaacg nccntgaaaa ancaggcna anannntccg    780
canatcctat cccttanttn ggggnccctt ncccngggcc cc                    822
```

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

```
cggccgcctg ctctggcaca tgcctcctga atggcatcaa aagtgatgga ctgcccattg    60
ctagagaaga ccttctctcc tactgtcatt atggagccct gcagactgag ggctccccctt   120
gtctgcagga tttgatgtct gaagtcgtgg agtgtggctt ggagctcctc atctacatna   180
gctggaagcc ctggagggcc tctctcgcca gcctcccct tctctccacg ctctccangg     240
acaccagggg ctccaggcag cccattattc ccagnangac atggtgtttc tccacgcgga    300
cccatggggc ctgnaaggcc agggtctcct ttgacaccat ctctcccgtc ctgcctggca    360
ggccgtggga tccactantt ctanaacggn cgccaccncg gtgggagctc cagcttttgt    420
tcccnttaat gaaggttaat tgcncgcttg gcgtaatcat nggtcanaac tntttcctgt    480
gtgaaattgt ttntccctc ncnattccnc ncnacatacn aacccggaan cataaagtgt     540
taaagcctgg gggtngcctn nngaatnaac tnaactcaat taattgcgtt ggctcatggc    600
ccgctttccn ttcnggaaaa ctgtcntccc ctgcnttnnt gaatcggcca cccccnggg    660
aaaagcggtt tgcnttttng ggggntcctt ccncttcccc cctcnctaan ccctncgcct    720
cggtcgttnc nggtngcggg gaagggnat nnnctcccnc naagggggng agnnngntat    780
``` cccaaa                                                                787

<210> SEQ ID NO 31
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31
tttttttttt tttttttggc gatgctactg tttaattgca ggaggtgggg gtgtgtgtac     60
catgtaccag ggctattaga agcaagaagg aaggagggag ggcagagcgc cctgctgagc    120
aacaaaggac tcctgcagcc ttctctgtct gtctcttggc gcaggcacat ggggaggcct    180
cccgcagggt gggggccacc agtccagggg tgggagcact acangggtg ggagtgggtg     240
gtggctggtn cnaatggcct gncacanatc cctacgattc ttgacacctg gatttcacca    300
ggggaccttc tgttctccca nggnaacttc ntnnatctcn aaagaacaca actgtttctt    360
cngcanttct ggctgttcat ggaaagcaca ggtgtccnat ttnggctggg acttggtaca    420
tatggttccg gcccacctct cccntcnaan aagtaattca cccccccccn ccntctnttg    480
cctgggccct taantaccca caccggaact canttantta ttcatcttng gntgggcttg    540
ntnatcnccn cctgaangcg ccaagttgaa aggccacgcc gtnccnctc cccatagnan     600
nttttnncnt canctaatgc ccccccnggc aacnatccaa tccccccccn tggggcccc     660
agcccanggc ccccgnctcg ggnnccngn cncgnantcc ccaggntctc ccantcngnc     720
ccnnngcncc cccgcacgca gaacanaagg ntngagccnc cgcannnnnn ggtnncnac     780
ctcgccccc ccnncgnng                                                   799

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32
tttttttttt tttttttttt tttttttttt tttttttttt tttttttttt tttttttttt     60
ttttnccnag ggcaggttta ttgacaacct cncgggacac aancaggctg ggacaggac     120
ggcaacaggc tccggcggcg gcggcggcgg ccctacctgc ggtaccaaat ntgcagcctc    180
cgctcccgct tgatnttcct ctgcagctgc aggatgccnt aaaacagggc ctcggccntn    240
ggtgggcacc ctgggatttn aatttccacg ggcacaatgc ggtcgcancc cctcaccacc    300
nattaggaat agtggtntta cccnccnccg ttggcncact cccntggaa accacttntc     360
gcggctccgg catctggtct taaaccttgc aaacnctggg gccctctttt tggttantnt    420
nccngccaca atcatnactc agactggcnc gggctggccc caaaaaancn ccccaaaacc    480
ggnccatgtc ttnncgggt tgctgcnatn tncatcacct cccgggcnca naggncaac     540
ccaaagttc ttgnggcccn caaaaaanct ccggggggnc ccagtttcaa caaagtcatc    600
ccccttggcc cccaaatcct cccccgntt nctgggtttg ggaacccacg cctctnnctt    660
tggnnggcaa gntggntccc ccttcgggcc cccggtgggc ccnnctctaa ngaaaacncc    720

| | |
|---|---:|
| ntcctnnnca ccatcccccc nngnnacgnc tancaangna tcccttttt tanaaacggg | 780 |
| ccccccncg | 789 |

<210> SEQ ID NO 33
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33

| | |
|---|---:|
| gacagaacat gttggatggt ggagcacctt tctatacgac ttacaggaca gcagatgggg | 60 |
| aattcatggc tgttggagca atanaacccc agttctacga gctgctgatc aaaggacttg | 120 |
| gactaaagtc tgatgaactt cccaatcaga tgagcatgga tgattggcca gaaatgaana | 180 |
| agaagtttgc agatgtattt gcaaagaaga cgaaggcaga gtggtgtcaa atctttgacg | 240 |
| gcacagatgc ctgtgtgact ccggttctga cttttgagga ggttgttcat catgatcaca | 300 |
| acaangaacg gggctcgttt atcaccantg aggagcagga cgtgagcccc cgccctgcac | 360 |
| ctctgctgtt aaacacccca gccatcccct cttcaaaag ggatccacta cttctagagc | 420 |
| ggncgccacc gcggtggagc tccagctttt gttccctta gtgagggtta attgcgcgct | 480 |
| tggcgtaatc atggtcatan ctgtttcctg tgtgaaattg ttatccgctc acaattccac | 540 |
| acaacatacg anccggaagc atnaaattt aaagcctggn ggtngcctaa tgantgaact | 600 |
| nactcacatt aattggcttt gcgctcactg cccgctttcc agtccggaaa acctgtcctt | 660 |
| gccagctgcc nttaatgaat cnggccaccc ccgggggaaa aggcngtttg cttnttgggg | 720 |
| cgcncttccc gctttctcgc ttcctgaant ccttccccccc ggtctttcgg cttgcggcna | 780 |
| acggtatcna cct | 793 |

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34

| | |
|---|---:|
| gccgcgaccg gcatgtacga gcaactcaag ggcgagtgga accgtaaaag ccccaatctt | 60 |
| ancaagtgcg gggaanagct gggtcgactc aagctagttc ttctggagct caacttcttg | 120 |
| ccaaccacag ggaccaagct gaccaaacag cagctaattc tggcccgtga catactggag | 180 |
| atcggggccc aatggagcat cctacgcaan gacatcccct ccttcgagcg ctacatggcc | 240 |
| cagctcaaat gctactactt tgattacaan gagcagctcc ccgagtcagc ctatatgcac | 300 |
| cagctcttgg gcctcaacct cctcttcctg ctgtcccaga accgggtggc tgantnccac | 360 |
| acgganttgg ancggctgcc tgcccaanga catacanacc aatgtctaca tcnaccacca | 420 |
| gtgtcctgga gcaatactga tggaggcag ctaccncaaa gtnttcctgg ccnagggtaa | 480 |
| catccccgc cgagagctac accttcttca ttgacatcct gctcgacact atcagggatg | 540 |
| aaaatcgcng ggttgctcca gaaaggctnc aanaanatcc ttttcnctga aggccccgg | 600 |
| atncnctagt nctagaatcg gccgccatc gcggtgganc ctccaacctt tcgttncct | 660 |
| ttactgaggg ttnattgccg cccttggcgt tatcatggtc acnccngttn cctgtgttga | 720 |

```
aattnttaac cccccacaat tccacgccna cattng                          756
```

<210> SEQ ID NO 35
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35

```
ggggatctct anatcnacct gnatgcatgg ttgtcggtgt ggtcgctgtc gatgaanatg   60
aacaggatct tgcccttgaa gctctcggct gctgtnttta agttgctcag tctgccgtca  120
tagtcagaca cnctcttggg caaaaaacan caggatntga gtcttgattt cacctccaat  180
aatcttcngg gctgtctgct cggtgaactc gatgacnang ggcagctggt tgtgntgat   240
aaantccanc angttctcct tggtgacctc cccttcaaag ttgttccggc cttcatcaaa  300
cttctnnaan angannancc canctttgtc gagctggnat ttgganaaca cgtcactgtt  360
ggaaactgat cccaaatggt atgtcatcca tcgcctctgc tgcctgcaaa aaacttgctt  420
ggcncaaatc cgactcccn tccttgaaag aagccnatca caccccctc cctgactcc    480
nncaangact ctnccgctnc cccntccnng cagggttggt ggcannccgg gcccntgcgc  540
ttcttcagcc agttcacnat nttcatcagc ccctctgcca gctgttntat tccttggggg  600
ggaanccgtc tctcccttcc tgaannaact ttgaccgtng aatagccgc gcntcnccnt   660
acntnctggg ccgggttcaa antccctccn ttgncnntcn cctcgggcca ttctggattt  720
nccnaacttt ttccttcccc cnccccncgg ngtttggntt tttcatnggg ccccaactct  780
gctnttggcc antccctgg gggcntntan cnccccctnt ggtcccntng ggcc         834
```

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36

```
cggncgcttt ccngccgcgc cccgtttcca tgacnaaggc tcccttcang ttaaatacnn   60
cctagnaaac attaatgggt tgctctacta atacatcata cnaaccagta agcctgccca  120
naacgccaac tcaggccatt cctaccaaag aagaaaaggc tggtctctcc accccctgta  180
ggaaaggcct gccttgtaag acaccacaat ncggctgaat ctnaagtctt gtgttttact  240
aatggaaaaa aaaataaac aanaggtttt gttctcatgg ctgcccaccg cagcctggca  300
ctaaaacanc ccagcgctca cttctgcttg ganaaatatt ctttgctctt ttggacatca  360
ggcttgatgg tatcactgcc acntttccac ccagctgggc nccctcccc catntttgtc   420
antganctgg aaggcctgaa ncttagtctc caaaagtctc ngcccacaag accggccacc  480
agggggangtc ntttncagtg gatctgccaa anantacccn tatcatcnnt gaataaaaag  540
gcccctgaac ganatgcttc cancanccctt taagacccat aatcctngaa ccatggtgcc  600
cttccggtct gatccaaaag gaatgttcct gggtcccant ccctcctttg ttncttacgt  660
tgtntttggac ccntgctngn atnacccaan tganatcccc ngaagcaccc tnccctggc  720
```

```
atttganttt cntaaattct ctgccctacn nctgaaagca cnattccctn ggcnccnaan     780
ggngaactca agaaggtctn ngaaaaacca cncn                                814
```

<210> SEQ ID NO 37
<211> LENGTH: 760
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37

```
gcatgctgct cttcctcaaa gttgttcttg ttgccataac aaccaccata ggtaaagcgg      60
gcgcagtgtt cgctgaaggg gttgtagtac cagcgcggga tgctctcctt gcagagtcct     120
gtgtctggca ggtccacgca atgcccttg tcactgggga aatggatgcg ctggagctcg      180
tcnaanccac tcgtgtattt ttcacangca gcctcctccg aagcntccgg gcagttgggg     240
gtgtcgtcac actccactaa actgtcgatn cancagccca ttgctgcagc ggaactgggt    300
gggctgacag gtgccagaac acactggatn ggcctttcca tggaagggcc tgggggaaat    360
cncctnancc caaactgcct ctcaaaggcc accttgcaca ccccgacagg ctagaaatgc    420
actcttcttc ccaaaggtag ttgttcttgt tgcccaagca ncctccanca aaccaaaanc    480
ttgcaaaatc tgctccgtgg gggtcatnnn taccanggtt gggaaanaa acccggcngn    540 ganccncctt gtttgaatgc naaggnaata atcctcctgt cttgcttggg tggaanagca    600
caattgaact gttaacnttg ggccgngttc cnctngggtg gtctgaaact aatcaccgtc    660
actggaaaaa ggtangtgcc ttccttgaat tcccaaantt cccctngntt tgggtnnttt    720
ctcctctncc ctaaaaatcg tnttcccccc ccntanggcg                          760
```

<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38

```
tttttttttt tttttttttt tttttttttt tttttaaaaa cccctccat tgaatgaaaa      60 cttccnaaat tgtccaaccc cctcnnccaa atnnccattt ccgggggggg gttccaaacc    120
caaattaatt ttgganttta aattaaatnt tnattngggg aanaanccaa atgtnaagaa    180
aatttaaccc attatnaact taaatncctn gaaaccntg gnttccaaaa attttaacc     240 cttaaatccc tccgaaattg ntaanggaaa accaaattcn cctaaggctn tttgaaggtt    300
ngatttaaac ccccttnant tnttttnacc cnngnctnaa ntatttngnt tccggtgttt    360
tcctnttaan cntnggtaac tcccgntaat gaannnccct aanccaatta aaccgaattt    420
tttttgaatt ggaaattccn ngggaattna ccggggtttt tccntttgg gggccatncc    480 cccnctttcg gggtttgggn ntaggttgaa tttttnnang nccaaaaaaa nccccccaana  540 aaaaaactcc caagnnttaa ttngaatntc ccccttccca ggccttttgg gaaaggnggg    600
tttntggggg ccngggantt cnttcccccn ttnccncccc ccccccnggt aaanggttat    660
ngnntttggt ttttgggccc cttnanggac cttccggatn gaaattaaat ccccgggncg    720
gccg                                                                724
```

<210> SEQ ID NO 39
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 39

| | | | | | |
|---|---|---|---|---|---|
| tttttttttt | ttttctttg | ctcacattta | attttattt | tgatttttt | taatgctgca | 60 |
| caacacaata | tttatttcat | ttgtttcttt | tatttcattt | tatttgtttg | ctgctgctgt | 120 |
| tttatttatt | tttactgaaa | gtgagaggga | acttttgtgg | cctttttcc | tttttctgta | 180 |
| ggccgcctta | agctttctaa | atttggaaca | tctaagcaag | ctgaanggaa | aaggggttt | 240 |
| cgcaaaatca | ctcgggggaa | nggaaaggtt | gctttgttaa | tcatgccta | tggtgggtga | 300 |
| ttaactgctt | gtacaattac | ntttcactttt | taattaattg | tgctnaangc | tttaattana | 360 |
| cttgggggtt | ccctccccan | accaaccccn | ctgacaaaaa | gtgccngccc | tcaaatnatg | 420 |
| tcccggcnnt | cnttgaaaca | cacngcngaa | ngttctcatt | ntccccncnc | caggtnaaaa | 480 |
| tgaagggtta | ccatnttaa | cnccacctcc | acntggcnnn | gctgaatcc | tcnaaaancn | 540 |
| ccctcaancn | aattnctnng | ccccggtcnc | gcntnngtcc | cncccgggct | ccgggaantn | 600 |
| caccccnga | anncnntnnc | naacnaaatt | ccgaaaatat | tcccnntcnc | tcaattcccc | 660 |
| cnnagactnt | cctcnncnan | cncaattttc | ttttnntcac | gaacncgnnc | cnnaaaatgn | 720 |
| nnnncncctc | cnctngtccn | naatcnccan | c | | | 751 |

<210> SEQ ID NO 40
<211> LENGTH: 753
<212> TYPE: DNA
<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

| | | | | | |
|---|---|---|---|---|---|
| gtggtatttt | ctgtaagatc | aggtgttcct | ccctcgtagg | tttagaggaa | acaccctcat | 60 |
| agatgaaaac | cccccgaga | cagcagcact | gcaactgcca | agcagccggg | gtaggagggg | 120 |
| cgccctatgc | acagctgggc | ccttgagaca | gcagggcttc | gatgtcaggc | tcgatgtcaa | 180 |
| tggtctggaa | gcggcggctg | tacctgcgta | ggggcacacc | gtcagggccc | accaggaact | 240 |
| tctcaaagtt | ccaggcaacn | tcgttgcgac | acaccggaga | ccaggtgatn | agcttggggt | 300 |
| cggtcataan | cgcggtggcg | tcgtcgctgg | gagctggcag | ggcctcccgc | aggaaggcna | 360 |
| ataaaaggtg | cgcccccgca | ccgttcanct | cgcacttctc | naanaccatg | angttgggct | 420 |
| cnaacccacc | accanncgg | acttccttga | nggaattccc | aaatctcttc | gntcttgggc | 480 |
| ttctnctgat | gccctanctg | gttgcccngn | atgccaanca | nccccaancc | ccgggtcct | 540 |
| aaancacccn | cctcctcntt | tcatctgggt | tnttntcccc | ggaccntggt | tcctctcaag | 600 |
| ggancccata | tctcnaccan | tactcaccnt | nccccccnt | gnnacccanc | cttctannga | 660 |
| ttcccncccg | ncctctggcc | cntcaaanan | gcttcacna | cctgggtctg | ccttcccccc | 720 |
| tncctatct | gnacccncn | tttgtctcan | tnt | | | 753 |

<210> SEQ ID NO 41

<211> LENGTH: 341
<212> TYPE: DNA
<213> ORGANISM: Homo sapien

<400> SEQUENCE: 41

```
actatatcca tcacaacaga catgcttcat cccatagact tcttgacata gcttcaaatg      60
agtgaaccca tccttgattt atatacatat atgttctcag tattttggga gcctttccac     120
ttctttaaac cttgttcatt atgaacactg aaaataggaa tttgtgaaga gttaaaaagt     180
tatagcttgt ttacgtagta agttttttgaa gtctacattc aatccagaca cttagttgag     240
tgttaaactg tgattttttaa aaaatatcat ttgagaatat tctttcagag gtatttcat      300
ttttactttt tgattaattg tgttttatat attagggtag t                         341
```

<210> SEQ ID NO 42
<211> LENGTH: 101
<212> TYPE: DNA
<213> ORGANISM: Homo sapien

<400> SEQUENCE: 42

```
acttactgaa tttagttctg tgctcttcct tatttagtgt tgtatcataa atactttgat      60
gtttcaaaca ttctaaataa ataattttca gtggcttcat a                         101
```

<210> SEQ ID NO 43
<211> LENGTH: 305
<212> TYPE: DNA
<213> ORGANISM: Homo sapien

<400> SEQUENCE: 43

```
acatctttgt tacagtctaa gatgtgttct taaatcacca ttccttcctg gtcctcaccc      60
tccagggtgg tctcacactg taattagagc tattgaggag tctttacagc aaattaagat     120
tcagatgcct tgctaagtct agagttctag agttatgttt cagaaagtct aagaaaccca     180
cctcttgaga ggtcagtaaa gaggacttaa tatttcatat ctacaaaatg accacaggat     240
tggatacaga acgagagtta tcctggataa ctcagagctg agtacctgcc cggggggccgc     300
tcgaa                                                                 305
```

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44

```
acataaatat cagagaaaag tagtctttga aatatttacg tccaggagtt ctttgtttct      60
gattatttgg tgtgtgtttt ggtttgtgtc caaagtattg gcagcttcag ttttcatttt     120
ctctccatcc tcgggcattc ttcccaaatt tatataccag tcttcgtcca tccacacgct     180
ccagaatttc tcttttgtag taatatctca tagctcggct gagcttttca taggtcatgc     240
tgctgttgtt cttcttttta ccccatagct gagccactgc ctctgatttc aagaacctga     300
agacgccctc agatcggtct tcccatttta ttaatcctgg gttcttgtct gggttcaaga     360
ggatgtcgcg gatgaattcc cataagtgag tccctctcgg gttgtgcttt ttggtgtggc     420
acttggcagg ggggtcttgc tccttttca tatcaggtga ctctgcaaca ggaaggtgac     480
tggtggttgt catggagatc tgagcccggc agaaagtttt gctgtccaac aaatctactg     540
```

```
tgctaccata gttggtgtca tataaatagt tctngtctتt ccaggtgttc atgatggaag      600
gctcagtttg ttcagtcttg acaatgacat tgtgtgtgga ctggaacagg tcactactgc      660
actggccgtt ccacttcaga tgctgcaagt tgctgtagag gagntgcccc gccgtccctg      720
ccgcccgggt gaactcctgc aaactcatgc tgcaaggtg ctcgccgttg atgtcgaact       780
cntggaaagg gatacaattg gcatccagct ggttggtgtc caggaggtga tggagccact      840
cccacacctg gt                                                          852
```

```
<210> SEQ ID NO 45
<211> LENGTH: 234
<212> TYPE: DNA
<213> ORGANISM: Homo sapien

<400> SEQUENCE: 45
acaacagacc cttgctcgct aacgacctca tgctcatcaa gttggacgaa tccgtgtccg       60
agtctgacac catccggagc atcagcattg cttcgcagtg ccctaccgcg gggaactctt      120
gcctcgtttc tggctggggt ctgctggcga acggcagaat gcctaccgtg ctgcagtgcg      180
tgaacgtgtc ggtggtgtct gaggaggtct gcagtaagct ctatgacccg ctgt           234
```

```
<210> SEQ ID NO 46
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46
actttttatt taaatgttta taaggcagat ctatgagaat gatagaaaac atggtgtgta       60
atttgatagc aatattttgg agattacaga gttttagtaa ttaccaatta cacagttaaa      120
aagaagataa tatattccaa gcanatacaa aatatctaat gaaagatcaa ggcaggaaaa      180
tgantataac taattgacaa tggaaaatca attttaatgt gaattgcaca ttatccttta      240
aaagctttca aaanaaanaa ttattgcagt ctanttaatt caaacagtgt taaatggtat      300
caggataaan aactgaaggg canaaagaat taattttcac ttcatgtaac ncacccanat      360
ttacaatggc ttaaatgcan ggaaaaagca gtggaagtag ggaagtantc aaggtctttc      420
tggtctctaa tctgccttac tctttgggtg tggctttgat cctctggaga cagctgccag      480
ggctcctgtt atatccacaa tcccagcagc aagatgaagg gatgaaaaag gacacatgct      540
gccttccttt gaggagactt catctcactg gccaacactc agtcacatgt                590
```

```
<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47 acaaggggc ataatgaagg agtggggana gattttaaag aaggaaaaaa aacgaggccc        60
tgaacagaat tttcctgnac aacgggctt caaaataatt ttcttgggga ggttcaagac      120
gcttcactgc ttgaaactta aatggatgtg ggacanaatt ttctgtaatg accctgaggg      180
```

| | |
|---|---|
| cattacagac gggactctgg gaggaaggat aaacagaaag gggacaaagg ctaatcccaa | 240 |
| aacatcaaag aaaggaaggt ggcgtcatac ctcccagcct acacagttct ccagggctct | 300 |
| cctcatccct ggaggacgac agtggaggaa caactgacca tgtccccagg ctcctgtgtg | 360 |
| ctggctcctg gtcttcagcc cccagctctg gaagcccacc ctctgctgat cctgcgtggc | 420 |
| ccacactcct tgaacacaca tccccaggtt atattcctgg acatggctga acctcctatt | 480 |
| cctacttccg agatgccttg ctccctgcag cctgtcaaaa tcccactcac cctccaaacc | 540 |
| acggcatggg aagcctttct gacttgcctg attactccag catcttggaa caatccctga | 600 |
| ttccccactc cttagaggca agataggggtg gttaagagta gggctggacc acttggagcc | 660 |
| aggctgctgg cttcaaattn tggctcattt acgagctatg ggaccttggg caagtnatct | 720 |
| tcacttctat gggcntcatt ttgttctacc tgcaaaatgg gggataataa tagt | 774 |

<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48

| | |
|---|---|
| canaaattga aattttataa aaaggcattt ttctcttata tccataaaat gatataattt | 60 |
| ttgcaantat anaaatgtgt cataaattat aatgttcctt aattacagct caacgcaact | 120 |
| tggt | 124 |

<210> SEQ ID NO 49
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 49

| | |
|---|---|
| gccgatgcta ctattttatt gcaggaggtg ggggtgtttt tattattctc tcaacagctt | 60 |
| tgtggctaca ggtggtgtct gactgcatna aaaantttt tacgggtgat tgcaaaaatt | 120 |
| ttagggcacc catatcccaa gcantgt | 147 |

<210> SEQ ID NO 50
<211> LENGTH: 107
<212> TYPE: DNA
<213> ORGANISM: Homo sapien

<400> SEQUENCE: 50

| | |
|---|---|
| acattaaatt aataaaagga ctgttggggt tctgctaaaa cacatggctt gatatattgc | 60 |
| atggtttgag gttaggagga gttaggcata tgttttggga gagggt | 107 |

<210> SEQ ID NO 51
<211> LENGTH: 204
<212> TYPE: DNA
<213> ORGANISM: Homo sapien

<400> SEQUENCE: 51

| | |
|---|---|
| gtcctaggaa gtctagggga cacacgactc tggggtcacg gggccgacac acttgcacgg | 60 |
| cgggaaggaa aggcagagaa gtgacaccgt caggggggaaa tgacagaaag gaaaatcaag | 120 |

```
gccttgcaag gtcagaaagg ggactcaggg cttccaccac agccctgccc cacttggcca      180
cctccctttt gggaccagca atgt                                             204
```

```
<210> SEQ ID NO 52
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52
acaaagataa catttatctt ataacaaaaa tttgatagtt ttaaaggtta gtattgtgta       60
gggtattttc caaaagacta aagagataac tcaggtaaaa agttagaaat gtataaaaca      120
ccatcagaca ggttttttaaa aaacaacata ttacaaaatt agacaatcat ccttaaaaaa     180
aaaacttctt gtatcaattt cttttgttca aaatgactga cttaantatt tttaaatatt     240
tcanaaacac ttcctcaaaa attttcaana tggtagcttt canatgtncc ctcagtccca     300
atgttgctca gataaataaa tctcgtgaga acttaccacc caccacaagc tttctggggc     360
atgcaacagt gtcttttctt tncttttttct tttttttttt ttacaggcac agaaactcat    420
caattttatt tggataacaa agggtctcca aattatattg aaaaataaat ccaagttaat     480
atcactcttg t                                                           491
```

```
<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 53
acataattta gcagggctaa ttaccataag atgctattta ttaanaggtn tatgatctga      60
gtattaacag ttgctgaagt ttggtatttt tatgcagcat tttcttttg ctttgataac      120 actacagaac ccttaaggac actgaaaatt agtaagtaaa gttcagaaac attagctgct    180
caatcaaatc tctacataac actatagtaa ttaaaacgtt aaaaaaaagt gttgaaatct     240
gcactagtat anaccgctcc tgtcaggata anactgcttt ggaacagaaa gggaaaaanc    300
agctttgant ttcttttgtgc tgatangagg aaaggctgaa ttaccttgtt gcctctccct     360
aatgattggc aggtcngggta aatnccaaaa catattccaa ctcaacactt cttttccncg    420
tancttgant ctgtgtattc caggancagg cggatggaat gggccagccc ncggatgttc     480 cant                                                                   484
```

```
<210> SEQ ID NO 54
<211> LENGTH: 151
<212> TYPE: DNA
<213> ORGANISM: Homo sapien

<400> SEQUENCE: 54
actaaacctc gtgcttgtga actccataca gaaaacggtg ccatccctga acacggctgg      60
ccactgggta tactgctgac aaccgcaaca acaaaaacac aaatccttgg cactggctag    120
tctatgtcct ctcaagtgcc ttttttgtttg t                                    151
```

<210> SEQ ID NO 55
<211> LENGTH: 91
<212> TYPE: DNA
<213> ORGANISM: Homo sapien

<400> SEQUENCE: 55
acctggcttg tctccgggtg gttcccggcg ccccccacgg tccccagaac ggcactttc    60 gccctccagt ggatactcga gccaaagtgg t                                  91

<210> SEQ ID NO 56
<211> LENGTH: 133
<212> TYPE: DNA
<213> ORGANISM: Homo sapien

<400> SEQUENCE: 56
ggcggatgtg cgttggttat atacaaatat gtcattttat gtaagggact tgagtatact    60
tggatttttg gtatctgtgg gttgggggga cggtccagga accaataccc catggatacc   120
aagggacaac tgt                                                      133

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57
actctggaga acctgagccg ctgctccgcc tctgggatga ggtgatgcan gcngtggcgc    60
gactgggagc tgagcccttc cctttgcgcc tgcctcagag gattgttgcc gacntgcana   120
tctcantggg ctggatncat gcagggt                                       147

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58
acagggatat aggtttnaag ttattgtnat tgtaaaatac attgaatttt ctgtatactc    60
tgattacata catttatcct ttaaaaaaga tgtaaatctt aatttttatg ccatctatta   120
atttaccaat gagttacctt gtaaatgaga agtcatgata gcactgaatt taactagtt    180 ttgacttcta agtttggt                                                 198

<210> SEQ ID NO 59
<211> LENGTH: 330
<212> TYPE: DNA
<213> ORGANISM: Homo sapien

<400> SEQUENCE: 59
acaacaaatg ggttgtgagg aagtcttatc agcaaaactg gtgatggcta ctgaaaagat    60
ccattgaaaa ttatcattaa tgattttaaa tgacaagtta tcaaaaactc actcaatttt   120
cacctgtgct agcttgctaa aatggagtt aactctagag caaatatagt atcttctgaa   180
tacagtcaat aaatgacaaa gccagggcct acaggtggtt tccagacttt ccagacccag   240

```
cagaaggaat ctattttatc acatggatct ccgtctgtgc tcaaaatacc taatgatatt    300
tttcgtcttt attggacttc tttgaagagt                                     330

<210> SEQ ID NO 60
<211> LENGTH: 175
<212> TYPE: DNA
<213> ORGANISM: Homo sapien

<400> SEQUENCE: 60
accgtgggtg ccttctacat tcctgacggc tccttcacca acatctggtt ctacttcggc    60
gtcgtgggct ccttcctctt catcctcatc cagctggtgc tgctcatcga ctttgcgcac    120
tcctggaacc agcggtggct gggcaaggcc gaggagtgcg attcccgtgc ctggt         175

<210> SEQ ID NO 61
<211> LENGTH: 154
<212> TYPE: DNA
<213> ORGANISM: Homo sapien

<400> SEQUENCE: 61
accccacttt tcctcctgtg agcagtctgg acttctcact gctacatgat gagggtgagt    60
ggttgttgct cttcaacagt atcctcccct ttccggatct gctgagccgg acagcagtgc    120
tggactgcac agccccgggg ctccacattg ctgt                                154

<210> SEQ ID NO 62
<211> LENGTH: 30
<212> TYPE: DNA
<213> ORGANISM: Homo sapien

<400> SEQUENCE: 62
cgctcgagcc ctatagtgag tcgtattaga                                     30

<210> SEQ ID NO 63
<211> LENGTH: 89
<212> TYPE: DNA
<213> ORGANISM: Homo sapien

<400> SEQUENCE: 63
acaagtcatt tcagcaccct ttgctcttca aaactgacca tcttttatat ttaatgcttc    60
ctgtatgaat aaaaatggtt atgtcaagt                                      89

<210> SEQ ID NO 64
<211> LENGTH: 97
<212> TYPE: DNA
<213> ORGANISM: Homo sapien

<400> SEQUENCE: 64
accggagtaa ctgagtcggg acgctgaatc tgaatccacc aataaataaa ggttctgcag    60
aatcagtgca tccaggattg gtccttggat ctggggt                             97

<210> SEQ ID NO 65
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 65
```

-continued

| | | |
|---|---|---|
| acaacaanaa ntcccttctt taggccactg atggaaacct ggaaccccct tttgatggca | 60 | |
| gcatggcgtc ctaggccttg acacagcggc tggggtttgg gctntcccaa accgcacacc | 120 | |
| ccaaccctgg tctacccaca nttctggcta tgggctgtct ctgccactga acatcagggt | 180 | |
| tcggtcataa natgaaatcc caangggac agaggtcagt agaggaagct caatgagaaa | 240 | |
| ggtgctgttt gctcagccag aaaacagctg cctggcattc gccgctgaac tatgaacccg | 300 | |
| tgggggtgaa ctaccccan gaggaatcat gcctgggcga tgcaanggtg ccaacaggag | 360 | |
| gggcgggagg agcatgt | 377 | |

<210> SEQ ID NO 66
<211> LENGTH: 305
<212> TYPE: DNA
<213> ORGANISM: Homo sapien

<400> SEQUENCE: 66

| | |
|---|---|
| acgcctttcc ctcagaattc agggaagaga ctgtcgcctg ccttcctccg ttgttgcgtg | 60 |
| agaacccgtg tgccccttcc caccatatcc accctcgctc catctttgaa ctcaaacacg | 120 |
| aggaactaac tgcaccctgg tcctctcccc agtccccagt tcaccctcca tccctcacct | 180 |
| tcctccactc taagggatat caacactgcc cagcacaggg gccctgaatt tatgtggttt | 240 |
| ttatatattt tttaataaga tgcactttat gtcattttt aataaagtct gaagaattac | 300 |
| tgttt | 305 |

<210> SEQ ID NO 67
<211> LENGTH: 385
<212> TYPE: DNA
<213> ORGANISM: Homo sapien

<400> SEQUENCE: 67

| | |
|---|---|
| actacacaca ctccacttgc ccttgtgaga cactttgtcc cagcacttta ggaatgctga | 60 |
| ggtcggacca gccacatctc atgtgcaaga ttgcccagca gacatcaggt ctgagagttc | 120 |
| ccctttaaa aaggggact tgcttaaaaa agaagtctag ccacgattgt gtagagcagc | 180 |
| tgtgctgtgc tggagattca cttttgagag agttctcctc tgagacctga tctttagagg | 240 |
| ctgggcagtc ttgcacatga gatggggctg gtctgatctc agcactcctt agtctgcttg | 300 |
| cctctcccag ggcccagcc tggccacacc tgcttacagg gcactctcag atgcccatac | 360 |
| catagtttct gtgctagtgg accgt | 385 |

<210> SEQ ID NO 68
<211> LENGTH: 73
<212> TYPE: DNA
<213> ORGANISM: Homo sapien

<400> SEQUENCE: 68

| | |
|---|---|
| acttaaccag atatattttt accccagatg gggatattct ttgtaaaaaa tgaaaataaa | 60 |
| gttttttaa tgg | 73 |

<210> SEQ ID NO 69
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 69

```
actagtccag tgtggtggaa ttccattgtg ttgggggctc tcaccctcct ctcctgcagc    60
tccagctttg tgctctgcct ctgaggagac catggcccag catctgagta ccctgctgct   120
cctgctggcc accctagctg tggccctggc ctggagcccc aaggaggagg ataggataat   180
cccgggtggc atctataacg cagacctcaa tgatgagtgg gtacagcgtg cccttcactt   240
cgccatcagc gagtataaca aggccaccaa agatgactac tacagacgtc cgctgcgggt   300
actaagagcc aggcaacaga ccgttggggg ggtgaattac ttcttcgacg tagaggtggg   360
ccgaaccata tgtaccaagt cccagcccaa cttggacacc tgtgccttcc atgaacagcc   420
agaactgcag aagaaacagt tgtgctcttt cgagatctac gaagttccct ggggagaaca   480
gaangtccct gggtgaaatc caggtgtcaa gaaatcctan ggatctgttg ccaggc       536
```

<210> SEQ ID NO 70
<211> LENGTH: 477
<212> TYPE: DNA
<213> ORGANISM: Homo sapien

<400> SEQUENCE: 70

```
atgacccta acaggggccc tctcagccct cctaatgacc tccggcctag ccatgtgatt    60
tcacttccac tccataacgc tcctcatact aggcctacta accaacacac taaccatata   120
ccaatgatgg cgcgatgtaa cacgagaaag cacataccaa ggccaccaca caccacctgt   180
ccaaaaaggc cttcgatacg ggataatcct atttattacc tcagaagttt ttttcttcgc   240
agggattttt ctgagccttt taccactcca gcctagcccc taccccccaa ctaggagggc   300
actggccccc aacaggcatc accccgctaa atcccctaga agtccactc ctaaacacat    360 ccgtattact cgcatcagga gtatcaatca cctgagctca ccatagtcta atagaaaaca   420
accgaaacca aattattcaa agcactgctt attacaattt tactgggtct ctattttt    477
```

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71

```
agagctatag gtacagtgtg atctcagctt tgcaaacaca ttttctacat agatagtact    60
aggtattaat agatatgtaa agaaagaaat cacaccatta ataatggtaa gattggttta   120
tgtgatttta gtggtatttt tggcaccctt atatatgttt tccaaacttt cagcagtgat   180
attatttcca taacttaaaa agtgagtttg aaaagaaaa tctccagcaa gcatctcatt    240
taaataaagg tttgtcatct ttaaaaatac agcaatatgt gacttttaa aaagctgtc    300 aaataggtgt gaccctacta ataattatta gaaatacatt taaaacatc gagtacctca    360 agtcagtttg ccttgaaaaa tatcaaatat aactcttaga gaaatgtaca taaagaatg    420 cttcgtaatt ttggagtang aggttccctc ctcaatttg tatttttaaa agtacatgg    480 taaaaaaaaa aattcacaac agtatataag gctgtaaaat gaagaattct gcc          533
```

<210> SEQ ID NO 72
<211> LENGTH: 511
<212> TYPE: DNA
<213> ORGANISM: Homo sapien
<220> FEATURE:

<221> NAME/KEY: misc_feature
<222> LOCATION: (1)...(511)
<223> OTHER INFORMATION: n = A,T,C or G

<400> SEQUENCE: 72

```
tattacggaa aaacacacca cataattcaa ctancaaaga anactgcttc agggcgtgta      60
aaatgaaagg cttccaggca gttatctgat taaagaacac taaaagaggg acaaggctaa    120
aagccgcagg atgtctacac tatancaggc gctatttggg ttggctggag agctgtgga    180
aaacatggan agattggtgc tgganatcgc cgtggctatt cctcattgtt attacanagt    240
gaggttctct gtgtgcccac tggtttgaaa accgttctnc aataatgata gaatagtaca    300
cacatgagaa ctgaaatggc ccaaacccag aaagaaagcc caactagatc ctcagaanac    360
gcttctaggg acaataaccg atgaagaaaa gatggcctcc ttgtgccccc gtctgttatg    420
atttctctcc attgcagcna naaacccgtt cttctaagca aacncaggtg atgatggcna    480
aaatacaccc cctcttgaag naccnggagg a                                    511
```

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73

```
cagtgccagc actggtgcca gtaccagtac caataacagt gccagtgcca gtgccagcac     60
cagtggtggc ttcagtgctg gtgccagcct gaccgccact ctcacatttg gctcttcgc    120
tggccttggt ggagctggtg ccagcaccag tggcagctct ggtgcctgtg gtttctccta    180
caagtgagat tttagatatt gttaatcctg ccagtctttc tcttcaagcc agggtgcatc    240
ctcagaaacc tactcaacac agcactctag gcagccacta tcaatcaatt gaagttgaca    300
ctctgcatta aatctatttg ccatttctga aaaaaaaaa aaaaaaggg cggccgctcg    360
antctagagg gcccgtttaa acccgctgat cagcctcgac tgtgccttct anttgccagc    420
catctgttgt tgcccctcc cccgntgcct tccttgaccc tggaaagtgc cactcccact    480
gtcctttcct aantaaaat                                                   499
```

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74

```
tttcatagga gaacacactg aggagatact tgaagaattt ggattcagcc gcgaagagat     60
ttatcagctt aactcagata aaatcattga agtaataag gtaaaagcta gtctctaact    120
tccaggccca cggctcaagt gaatttgaat actgcattta cagtgtagag taacacataa    180
cattgtatgc atggaaacat ggaggaacag tattacagtg tcctaccact ctaatcaaga    240
aaagaattac agactctgat ctacagtga tgattgaatt ctaaaatgg taatcattag    300
ggcttttgat ttataanact ttgggtactt atactaaatt atggtagtta tactgccttc    360
cagtttgctt gatatatttg ttgatattaa gattcttgac ttatattttg aatgggttct    420
```

```
actgaaaaan gaatgatata ttcttgaaga catcgatata catttattta cactcttgat    480
tctacaatgt agaaaatgaa ggaaatgccc caaattgtat ggtgataaaa gtcccgt       537
```

<210> SEQ ID NO 75
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75

```
caaanacaat tgttcaaaag atgcaaatga tacactactg ctgcagctca caaacacctc     60
tgcatattac acgtacctcc tcctgctcct caagtagtgt ggtctatttt gccatcatca    120
cctgctgtct gcttagaaga acggctttct gctgcaangg agagaaatca taacagacgg    180
tggcacaagg aggccatctt ttcctcatcg gttattgtcc ctagaagcgt cttctgagga    240
tctagttggg ctttctttct gggtttgggc catttcantt ctcatgtgtg tactattcta    300
tcattattgt ataacggttt tcaaaccngt gggcacncag agaacctcac tctgtaataa    360
caatgaggaa tagccacggt gatctccagc accaaatctc tccatgttnt tccagagctc    420
ctccagccaa cccaaatagc cgctgctatn gtgtagaaca tccctgn                 467
```

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76

```
aagctgacag cattcgggcc gagatgtctc gctccgtggc cttagctgtg ctcgcgctac     60
tctctctttc tggcctggag gctatccagc gtactccaaa gattcaggtt tactcacgtc    120
atccagcaga gaatggaaag tcaaatttcc tgaattgcta tgtgtctggg tttcatccat    180
ccgacattga agttgactta ctgaagaatg gagagagaat tgaaaagtg gagcattcag    240 acttgtcttt cagcaaggac tggtctttct atctcttgta ctacactgaa ttcacccccca   300 ctgaaaaaga tgagtatgcc tgccgtgtga accatgtgac tttgtcacag cccaagatng   360
ttnagtggga tcganacatg taagcagcan catgggaggt                          400
```

<210> SEQ ID NO 77
<211> LENGTH: 248
<212> TYPE: DNA
<213> ORGANISM: Homo sapien

<400> SEQUENCE: 77

```
ctggagtgcc ttggtgtttc aagcccctgc aggaagcaga atgcaccttc tgaggcacct     60
ccagctgccc cggcggggga tgcgaggctc ggagcaccct tgcccggctg tgattgctgc    120
caggcactgt tcatctcagc ttttctgtcc ctttgctccc ggcaagcgct tctgctgaaa    180
gttcatatct ggagcctgat gtcttaacga ataaaggtcc catgctccac ccgaaaaaaa    240
aaaaaaaa                                                             248
```

<210> SEQ ID NO 78

<211> LENGTH: 201
<212> TYPE: DNA
<213> ORGANISM: Homo sapien

<400> SEQUENCE: 78

```
actagtccag tgtggtggaa ttccattgtg ttgggcccaa cacaatggct acctttaaca      60
tcacccagac cccgccctgc ccgtgcccca cgctgctgct aacgacagta tgatgcttac     120
tctgctactc ggaaactatt tttatgtaat taatgtatgc tttcttgttt ataaatgcct     180
gatttaaaaa aaaaaaaaaa a                                               201
```

<210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79

```
tccttttgtt aggtttttga dacaacccta gacctaaact gtgtcacaga cttctgaatg      60
tttaggcagt gctagtaatt tcctcgtaat gattctgtta ttactttcct attctttatt    120
cctctttctt ctgaagatta atgaagttga aaattgaggt ggataaatac aaaaaggtag    180
tgtgatagta taagtatcta agtgcagatg aaagtgtgtt atatatatcc attcaaaatt    240
atgcaagtta gtaattactc agggttaact aaattacttt aatatgctgt tgaacctact    300
ctgttccttg gctagaaaaa attataaaca ggactttgtt agtttgggaa gccaaattga    360
taatattcta tgttctaaaa gttgggctat acataaanta tnaagaaata tggaattta     420
ttcccaggaa tatggggttc atttatgaat antacccggg anagaagttt tgantnaaac    480
cngttttggt taatacgtta atatgtcctn aatnaacaag gcntgactta tttccaaaaa    540
aaaaaaaaaa aa                                                        552
```

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80

```
acagggattt gagatgctaa ggccccagag atcgtttgat ccaaccctct tattttcaga      60
ggggaaaatg gggcctagaa gttacagagc atctagctgg tgcgctggca cccctggcct    120
cacacagact cccgagtagc tgggactaca ggcacacagt cactgaagca ggccctgttt    180
gcaattcacg ttgccacctc aacttaaac attcttcata tgtgatgtcc ttagtcacta    240
aggtaaaact ttcccaccca gaaaaggcaa cttagataaa atcttagagt actttcatac    300
tcttctaagt cctcttccag cctcactttg agtcctcctt gggggttgat aggaantntc    360
tcttggcttt tcaataaaa tctctatcca tctcatgttt aatttggtac gcntaaaaat    420
gctgaaaaaa ttaaatgttt ctggtttcnc tttaaaaaaa aaaaaaaaaa aaaaaa        476
```

<210> SEQ ID NO 81
<211> LENGTH: 232
<212> TYPE: DNA
<213> ORGANISM: Homo sapien

```
<220> FEATURE:
<221> NAME/KEY: misc_feature
<222> LOCATION: (1)...(232)
<223> OTHER INFORMATION: n = A,T,C or G

<400> SEQUENCE: 81 ttttttttg tatgccntcn ctgtggngtt attgttgctg ccaccctgga ggagcccagt      60
ttcttctgta tctttctttt ctggggatc ttcctggctc tgcccctcca ttcccagcct     120
ctcatcccca tcttgcactt ttgctagggt tggaggcgct ttcctggtag cccctcagag    180
actcagtcag cgggaataag tcctaggggt gggggtgtg gcaagccggc ct             232

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82
aggcgggagc agaagctaaa gccaaagccc aagaagagtg gcagtgccag cactggtgcc     60
agtaccagta ccaataacat gccagtgcca gtgccagcac cagtggtggc ttcagtgctg   120
gtgccagcct gaccgccact ctcacatttg ggctcttcgc tggccttggt ggagctggtg   180
ccagcaccag tggcagctct ggtgcctgtg gtttctccta caagtgagat tttagatatt   240
gttaatcctg ccagtctttc tcttcaagcc agggtgcatc ctcagaaacc tactcaacac   300
agcactctng gcagccacta tcaatcaatt gaagttgaca ctctgcatta aatctatttg   360
ccatttcaaa aaaaaaaaaa aaa                                            383

<210> SEQ ID NO 83
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83
accgaattgg gaccgctggc ttataagcga tcatgtcctc cagtattacc tcaacgagca     60
gggagatcga gtctatacgc tgaagaaatt tgacccgatg gacaacaga cctgctcagc    120 ccatcctgct cggttctccc cagatgacaa atactctcga caccgaatca ccatcaagaa   180
acgcttcaag gtgctcatga cccagcaacc gcgccctgtc ctctgagggt ccttaaactg   240
atgtcttttc tgccacctgt taccctcgg agactccgta accaaactct tcggactgtg    300
agccctgatg ccttttgcc agccatactc tttggcntcc agtctctcgt ggcgattgat    360
tatgcttgtg tgaggcaatc atggtggcat cacccatnaa gggaacacat ttganttttt   420
tttcncatat tttaaattac naccagaata nttcagaata aatgaattga aaaactctta   480
aaaaaaaaaa aaaa                                                      494

<210> SEQ ID NO 84
<211> LENGTH: 380
<212> TYPE: DNA
<213> ORGANISM: Homo sapien
<220> FEATURE:
<221> NAME/KEY: misc_feature
<222> LOCATION: (1)...(380)
```

<223> OTHER INFORMATION: n = A,T,C or G

<400> SEQUENCE: 84

```
gctggtagcc tatggcgtgg ccacggangg gctcctgagg cacgggacag tgacttccca     60
agtatcctgc gccgcgtctt ctaccgtccc tacctgcaga tcttcgggca gattccccag    120
gaggacatgg acgtggccct catggagcac agcaactgct cgtcggagcc cggcttctgg    180
gcacaccctc ctggggccca ggcgggcacc tgcgtctccc agtatgccaa ctggctggtg    240
gtgctgctcc tcgtcatctt cctgctcgtg gccaacatcc tgctggtcac ttgctcattg    300
ccatgttcag ttacacattc ggcaaagtac agggcaacag cnatctctac tgggaaggcc    360
agcgttnccg cctcatccgg                                                380
```

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85

```
gagttagctc ctccacaacc ttgatgaggt cgtctgcagt ggcctctcgc ttcataccgc     60
tnccatcgtc atactgtagg tttgccacca cctcctgcat cttggggcgg ctaatatcca    120
ggaaactctc aatcaagtca ccgtcnatna acctgtggc tggttctgtc ttccgctcgg    180
tgtgaaagga tctccagaag gagtgctcga tcttccccac actttgatg actttattga    240
gtcgattctg catgtccagc aggaggttgt accagctctc tgacagtgag gtcaccagcc    300
ctatcatgcc nttgaacgtg ccgaagaaca ccgagccttg tgtgggggt gnagtctcac    360
ccagattctg cattaccaga nagccgtggc aaaaganatt gacaactcgc ccaggnngaa    420
aaagaacacc tcctggaagt gctngccgct cctcgtccnt tggtggnngc gcntnccttt    480
t                                                                    481
```

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86

```
aacatcttcc tgtataatgc tgtgtaatat cgatccgatn ttgtctgctg agaattcatt     60
acttggaaaa gcaacttnaa gcctggacac tggtattaaa attcacaata tgcaacactt    120
taaacagtgt gtcaatctgc tcccttactt tgtcatcacc agtctgggaa taagggtatg    180
ccctattcac acctgttaaa agggcgctaa gcatttttga ttcaacatct ttttttttga    240
cacaagtccg aaaaaagcaa agtaaacag ttnttaattt gttagccaat tcactttctt    300
catgggacag agccatttga tttaaaaagc aaattgcata atattgagct ttgggagctg    360
atatntgagc ggaagantag cctttctact tcaccagaca caactccttt catattggga    420
tgttnacnaa agttatgtct cttacagatg ggatgctttt gtggcaattc tg            472
```

<210> SEQ ID NO 87
<211> LENGTH: 413

```
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 87
agaaaccagt atctctnaaa acaacctctc ataccttgtg gacctaattt tgtgtgcgtg      60
tgtgtgtgcg cgcatattat atagacaggc acatctttt tacttttgta aaagcttatg     120
cctctttggt atctatatct gtgaaagttt taatgatctc ccataatgtc ttggggacct    180
ttgtcttctg tgtaaatggt actagagaaa acacctatnt tatgagtcaa tctagtttngt   240 tttattcgac atgaaggaaa tttccagatn acaacactna caaactctcc cttgactagg    300
ggggacaaag aaaagcanaa ctgaacatna gaaacaattn cctggtgaga aattncataa    360
acagaaattg ggtngtatat tgaaananng catcattnaa acgttttttt ttt           413

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88
cgcagcgggt cctctctatc tagctccagc ctctcgcctg ccccactccc cgcgtcccgc     60
gtcctagccn accatggccg ggcccctgcg cgccccgctg ctcctgctgg ccatcctggc    120
cgtggccctg gccgtgagcc ccgcggccgg ctccagtccc ggcaagccgc cgcgcctggt    180
gggaggccca tggaccccgc gtggaagaag aaggtgtgcg cgtgcactg gactttgccg     240 tcggcnanta caacaaaccc gcaacnactt ttaccnagcn cgcgctgcag ttgtgccgc     300 cccaancaaa ttgttactng gggtaantaa ttcttggaag ttgaacctgg gccaaacnng    360
tttaccagaa ccnagccaat tngaacaatt nccctccat aacagcccct tttaaaaagg    420
gaancantcc tgntcttttc caaattt                                        448

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89
gaattttgtg cactggccac tgtgatggaa ccattgggcc aggatgcttt gagtttatca     60
gtagtgattc tgccaaagtt ggtgttgtaa catgagtatg taaaatgtca aaaaattagc    120
agaggtctag gtctgcatat cagcagacag tttgtccgtg tattttgtag ccttgaagtt    180
ctcagtgaca agttnnttct gatgcgaagt tctnattcca gtgttttagt cctttgcatc    240
tttnatgttn agacttgcct ctntnaaatt gcttttgtnt tctgcaggta ctatctgtgg    300
tttaacaaaa tagaannact tctctgcttn gaanatttga atatcttaca tctnaaaatn    360
aattctctcc ccatannaaa acccangccc tgggganaat ttgaaaaang gntccttcnn    420
aattcnnana anttcagntn tcatacaaca naacngganc ccc                      463
```

<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90

```
agggattgaa ggtctnttnt actgtcggac tgttcancca ccaactctac aagttgctgt      60
cttccactca ctgtctgtaa gcntnttaac ccagactgta tcttcataaa tagaacaaat     120
tcttcaccag tcacatcttc taggaccttt ttggattcag ttagtataag ctcttccact     180
tcctttgtta agacttcatc tggtaaagtc ttaagttttg tagaaaggaa tttaattgct     240
cgttctctaa caatgtcctc tccttgaagt atttggctga acaacccacc tnaagtccct     300
ttgtgcatcc attttaaata tacttaatag ggcattggtn cactaggtta aattctgcaa     360
gagtcatctg tctgcaaaag ttgcgttagt atatctgcca                           400
```

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91

```
gagctcggat ccaataatct ttgtctgagg gcagcacaca tatncagtgc catggnaact      60
ggtctacccc acatgggagc agcatgccgt agntatataa ggtcattccc tgagtcagac     120
atgcctcttt gactaccgtg tgccagtgct ggtgattctc acacacctcc nnccgctctt     180
tgtggaaaaa ctggcacttg nctggaacta gcaagacatc acttacaaat tcacccacga     240
gacacttgaa aggtgtaaca aagcgactct tgcattgctt tttgtccctc cggcaccagt     300
tgtcaatact aacccgctgg tttgcctcca tcacatttgt gatctgtagc tctggataca     360
tctcctgaca gtactgaaga acttcttctt ttgtttcaaa agcaactctt ggtgcctgtt     420
ngatcaggtt cccatttccc agtccgaatg ttcacatggc atatnttact tcccacaaaa     480
```

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92

```
atacagccca natcccacca cgaagatgcg cttgttgact gagaacctga tgcggtcact      60
ggtcccgctg tagccccagc gactctccac ctgctggaag cggttgatgc tgcactcctt     120
cccacgcagg cagcagcggg gccggtcaat gaactccact cgtggcttgg ggttgacggt     180
taantgcagg aagaggctga ccacctcgcg gtccaccagg atgcccgact gtgcgggacc     240
tgcagcgaaa ctcctcgatg gtcatgagcg ggaagcgaat gangcccagg gccttgccca     300
gaaccttccg cctgttctct ggcgtcacct gcagctgctg ccgctnacac tcggcctcgg     360
accagcggac aaacggcgtt gaacagccgc acctcacgga tgcccantgt gtcgcgctcc     420
```
aggaacggcn ccagcgtgtc caggtcaatg tcggtgaanc ctccgcgggt aatggcg    477

<210> SEQ ID NO 93
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93
gaacggctgg accttgcctc gcattgtgct gctggcagga ataccttggc aagcagctcc    60
agtccgagca gccccagacc gctgccgccc aagctaagc ctgcctctgg ccttcccctc    120
cgcctcaatg cagaaccant agtgggagca ctgtgtttag agttaagagt gaacactgtn    180
tgattttact tgggaatttc ctctgttata tagcttttcc caatgctaat ttccaaacaa    240
caacaacaaa ataacatgtt tgcctgttna gttgtataaa agtangtgat tctgtatnta    300
aagaaaatat tactgttaca tatactgctt gcaanttctg tatttattgg tnctctggaa    360
ataaatatat tattaaa                                                   377

<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94 cccttttgagg ggttagggtc cagttcccag tggaagaaac aggccaggag aantgcgtgc    60
cgagctgang cagatttccc acagtgaccc cagagccctg gctatagtc tctgaccct    120
ccaaggaaag accaccttct ggggacatgg gctggagggc aggacctaga ggcaccaagg    180
gaaggcccca ttccggggct gttccccgag gaggaaggga aggggctctg tgtgcccccc    240
acgaggaana ggccctgant cctgggatca nacacccctt cacgtgtatc cccacacaaa    300
tgcaagctca ccaaggtccc ctctcagtcc cttccctaca ccctgaacgg ncactggccc    360
acacccaccc agancancca cccgccatgg ggaatgtnct caaggaatcg cngggcaacg    420
tggactctng tcccnnaagg gggcagaatc tccaatagan ggannggaacc cttgctnana    480
aaaaaaaana aaaaa                                                     495

<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95
ggttacttgg tttcattgcc accacttagt ggatgtcatt tagaaccatt ttgtctgctc    60
cctctggaag ccttgcgcag agcggactt gtaattgttg gagaataact gctgaatttt    120
tagctgtttt gagttgattc gcaccactgc accacaactc aatatgaaaa ctatttnact    180
tatttattat cttgtgaaaa gtatacaatg aaaattttgt tcatactgta tttatcaagt    240

```
atgatgaaaa gcaatagata tatattctttt tattatgttn aattatgatt gccattatta    300
atcggcaaaa tgtggagtgt atgttctttt cacagtaata tatgccttt gtaacttcac    360 ttggttattt tattgtaaat gaattacaaa attcttaatt taagaaaatg gtangttata    420
tttanttcan taatttcttt ccttgtttac gttaattttg aaaagaatgc at    472
```

```
<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96
ctgaagcatt tcttcaaact tntctactt tgtcattgat acctgtagta agttgacaat     60
gtggtgaaat ttcaaaatta tatgtaactt ctactagttt tactttctcc cccaagtctt    120
ttttaactca tgattttac acacacaatc cagaacttat tatatagcct ctaagtcttt    180
attcttcaca gtagatgatg aaagagtcct ccagtgtctt gngcanaatg ttctagntat    240
agctggatac atacngtggg agttctataa actcatacct cagtgggact naaccaaaat    300
tgtgttagtc tcaattccta ccacactgag ggagcctccc aaatcactat attcttatct    360
gcaggtactc ctccagaaaa acngacaggg caggcttgca tgaaaaagtn acatctgcgt    420
tacaaagtct atcttcctca nangtctgtn aaggaacaat ttaatcttct agcttt      476
```

```
<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97
actctttcta atgctgatat gatcttgagt ataagaatgc atatgtcact agaatggata     60
aaataatgct gcaaacttaa tgttcttatg caaaatggaa cgctaatgaa acacagctta    120
caatcgcaaa tcaaaactca caagtgctca tctgttgtag atttagtgta ataagactta    180
gattgtgctc cttcggatat gattgttct canatcttgg gcaatnttcc ttagtcaaat    240
caggctacta gaattctgtt attggatatn tgagagcatg aaatttttaa naatacactt    300
gtgattatna aattaatcac aaatttcact tatacctgct atcagcagct agaaaaacat    360 ntnntttta natcaaagta ttttgtgttt ggaantgtnn aaatgaaatc tgaatgtggg    420
ttcnatctta ttttttcccn gacnactant tncttttta gggnctattc tganccatc     479
```

```
<210> SEQ ID NO 98
<211> LENGTH: 461
<212> TYPE: DNA
<213> ORGANISM: Homo sapien

<400> SEQUENCE: 98
agtgacttgt cctccaacaa aaccccttga tcaagtttgt ggcactgaca atcagaccta     60
tgctagttcc tgtcatctat tcgctactaa atgcagactg gaggggacca aaaaggggca    120
tcaactccag ctgattatt ttggagcctg caaatctatt cctacttgta cggactttga    180
agtgattcag tttcctctac ggatgagaga ctggctcaag aatatcctca tgcagcttta    240
```

```
tgaagccact ctgaacacgc tggttatcta gatgagaaca gagaaataaa gtcagaaaat      300
ttacctggag aaaagaggct ttggctgggg accatcccat tgaaccttct cttaaggact      360
ttaagaaaaa ctaccacatg ttgtgtatcc tggtgccggc cgtttatgaa ctgaccaccc      420
tttggaataa tcttgacgct cctgaacttg ctcctctgcg a                         461
```

<210> SEQ ID NO 99
<211> LENGTH: 171
<212> TYPE: DNA
<213> ORGANISM: Homo sapien

<400> SEQUENCE: 99

```
gtggccgcgc gcaggtgttt cctcgtaccg cagggccccc tcccttcccc aggcgtccct       60
cggcgcctct gcgggcccga ggaggagcgg ctggcgggtg gggggagtgt gacccaccct      120
cggtgagaaa agccttctct agcgatctga gaggcgtgcc ttgggggtac c              171
```

<210> SEQ ID NO 100
<211> LENGTH: 269
<212> TYPE: DNA
<213> ORGANISM: Homo sapien

<400> SEQUENCE: 100

```
cggccgcaag tgcaactcca gctggggccg tgcggacgaa gattctgcca gcagttggtc       60
cgactgcgac gacggcggcg cgacagtcg caggtgcagc gcgggcgcct ggggtcttgc      120
aaggctgagc tgacgccgca gaggtcgtgt cacgtccac gaccttgacg ccgtcgggga      180
cagccggaac agagcccggt gaagcgggag gcctcgggga gccctcgggg aagggcggcc      240
cgagagatac gcaggtgcag gtggccgcc                                        269
```

<210> SEQ ID NO 101
<211> LENGTH: 405
<212> TYPE: DNA
<213> ORGANISM: Homo sapien

<400> SEQUENCE: 101

```
tttttttttt tttggaatc tactgcgagc acagcaggtc agcaacaagt ttatttgca        60 gctagcaagg taacagggta gggcatggtt acatgttcag gtcaacttcc tttgtcgtgg     120
ttgattggtt tgtctttatg ggggcggggt gggtagggg aaacgaagca aataacatgg      180
agtgggtgca ccctccctgt agaacctggt tacaaagctt ggggcagttc acctggtctg     240
tgaccgtcat tttcttgaca tcaatgttat tagaagtcag gatatctttt agagagtcca     300
ctgttctgga gggagattag ggtttcttgc caaatccaac aaaatccact gaaaagttg      360 gatgatcagt acgaataccg aggcatattc tcatatcggt ggcca                     405
```

<210> SEQ ID NO 102
<211> LENGTH: 470
<212> TYPE: DNA
<213> ORGANISM: Homo sapien

<400> SEQUENCE: 102

```
tttttttttt tttttttttt tttttttttt tttttttttt tttttttttt tttttttttt       60
ggcacttaat ccatttttat ttcaaaatgt ctacaaattt aatcccatta tacggtattt     120
tcaaaatcta aattattcaa attagccaaa tccttaccaa ataatacccca aaatcaaaa     180 atatacttct ttcagcaaac ttgttacata aattaaaaaa atatatacgg ctggtgtttt     240
```

```
caaagtacaa ttatcttaac actgcaaaca ttttaaggaa ctaaaataaa aaaaaacact      300
ccgcaaaggt taaagggaac aacaaattct tttacaacac cattataaaa atcatatctc      360
aaatcttagg ggaatatata cttcacacgg gatcttaact tttactcact ttgttttattt    420 ttttaaacca ttgtttgggc ccaacacaat ggaatccccc ctggactagt                 470
```

<210> SEQ ID NO 103
<211> LENGTH: 581
<212> TYPE: DNA
<213> ORGANISM: Homo sapien

<400> SEQUENCE: 103

```
tttttttttt tttttttga ccccctctt ataaaaaca agttaccatt ttattttact         60
tacacatatt tatttataa ttggtattag atattcaaaa ggcagctttt aaaatcaaac       120
taaatggaaa ctgccttaga tacataattc ttaggaatta gcttaaaatc tgcctaaagt     180
gaaaatcttc tctagctctt ttgactgtaa attttttgact cttgtaaaac atccaaattc    240
atttttcttg tctttaaaat tatctaatct ttccattttt tccctattcc aagtcaattt    300
gcttctctag cctcatttcc tagctcttat ctactattag taagtggctt ttttcctaaa   360
agggaaaaca ggaagagaaa tggcacacaa aacaaacatt ttatattcat atttctacct   420
acgttaataa aatagcattt tgtgaagcca gctcaaaaga aggcttagat cctttttatgt   480 ccatttttagt cactaaacga tatcaaagtg ccagaatgca aaaggtttgt gaacatttat   540
tcaaaagcta atataagata tttcacatac tcatcttttct g                       581
```

<210> SEQ ID NO 104
<211> LENGTH: 578
<212> TYPE: DNA
<213> ORGANISM: Homo sapien

<400> SEQUENCE: 104

```
tttttttttt tttttttttt tttttctctt cttttttttt gaaatgagga tcgagttttt     60
cactctctag atagggcatg aagaaaactc atctttccag ctttaaaata acaatcaaat    120
ctcttatgct atatcatatt ttaagttaaa ctaatgagtc actggcttat cttctcctga    180
aggaaatctg ttcattcttc tcattcatat agttatatca agtactacct tgcatattga    240 gaggttttttc ttctctattt acacatatat ttccatgtga atttgtatca aacctttatt   300
ttcatgcaaa ctagaaaata atgtttcttt tgcataagag aagagaacaa tatagcatta   360
caaaactgct caaattgttt gttaagttat ccattataat tagttggcag gagctaatac   420
aaatcacatt tacgacagca ataataaaac tgaagtacca gttaaatatc caaataatt    480 aaaggaacat ttttagcctg ggtataatta gctaattcac tttacaagca tttattagaa   540
tgaattcaca tgttattatt cctagcccaa cacaatgg                            578
```

<210> SEQ ID NO 105
<211> LENGTH: 538
<212> TYPE: DNA
<213> ORGANISM: Homo sapien

<400> SEQUENCE: 105

```
tttttttttt ttttttcagta ataatcagaa caatatttat ttttatattt aaaattcata   60
gaaaagtgcc ttacatttaa taaaagtttg tttctcaaag tgatcagagg aattagatat    120
gtcttgaaca ccaatattaa tttgaggaaa atacaccaaa atacattaag taaattattt    180
aagatcatag agcttgtaag tgaaaagata aaatttgacc tcagaaactc tgagcattaa    240
```

```
aaatccacta ttagcaaata aattactatg gacttcttgc tttaattttg tgatgaatat      300
ggggtgtcac tggtaaacca acacattctg aaggatacat tacttagtga tagattctta      360
tgtactttgc taatacgtgg atatgagttg acaagtttct ctttcttcaa tcttttaagg      420
ggcgagaaat gaggaagaaa agaaaaggat tacgcatact gttctttcta tggaaggatt      480
agatatgttt cctttgccaa tattaaaaaa ataataatgt ttactactag tgaaaccc       538

<210> SEQ ID NO 106
<211> LENGTH: 473
<212> TYPE: DNA
<213> ORGANISM: Homo sapien

<400> SEQUENCE: 106
tttttttttt ttttttagtc aagtttctat ttttattata attaaagtct tggtcatttc       60
atttattagc tctgcaactt acatatttaa attaaagaaa cgttttagac aactgtacaa      120
tttataaatg taaggtgcca ttattgagta atatattcct ccaagagtgg atgtgtccct      180
tctcccacca actaatgaac agcaacatta gtttaatttt attagtagat atacactgct      240
gcaaacgcta attctcttct ccatccccat gtgatattgt gtatatgtgt gagttggtag      300
aatgcatcac aatctacaat caacagcaag atgaagctag gctgggcttt cggtgaaaat      360
agactgtgtc tgtctgaatc aaatgatctg acctatcctc ggtggcaaga actcttcgaa      420
ccgcttcctc aaaggcgctg ccacatttgt ggctctttgc acttgtttca aaa             473

<210> SEQ ID NO 107
<211> LENGTH: 1621
<212> TYPE: DNA
<213> ORGANISM: Homo sapien

<400> SEQUENCE: 107
cgccatggca ctgcagggca tctcggtcat ggagctgtcc ggcctggccc cgggcccgtt       60
ctgtgctatg gtcctggctg acttcggggc gcgtgtggta cgcgtggacc ggcccggctc      120
ccgctacgac gtgagccgct tgggccgggg caagcgctcg ctagtgctgg acctgaagca      180
gccgcgggga gccgccgtgc tgcggcgtct gtgcaagcgg tcggatgtgc tgctggagcc      240
cttccgccgc ggtgtcatgg agaaactcca gctgggccca gagattctgc agcgggaaaa      300
tccaaggctt atttatgcca ggctgagtgg atttggccag tcaggaagct tctgccggtt      360
agctggccac gatatcaact atttggcttt gtcaggtgtt ctctcaaaaa ttggcagaag      420
tggtgagaat ccgtatgccc cgctgaatct cctggctgac tttgctggtg gtggccttat      480
gtgtgcactg gcattataa tggctctttt tgaccgcaca cgcactgaca agggtcaggt      540
cattgatgca aatatggtgg aaggaacagc atatttaagt tcttttctgt ggaaaactca      600
gaaatcgagt ctgtgggaag cacctcgagg acagaacatg ttggatggtg gagcaccttt      660
ctatacgact tacaggacag cagatgggga attcatggct gttggagcaa tagaacccca      720
gttctacgag ctgctgatca aaggacttgg actaaagtct gatgaacttc ccaatcagat      780
gagcatggat gattggccag aaatgaagaa gaagtttgca gatgtatttg caagaagac       840 gaaggcgagt ggtgtcaaa tctttgacgg cacagatgcc tgtgtgactc cggttctgac      900
ttttgaggag gttgttcatc atgatcacaa caaggaacgg gctcgtttta tcaccagtga      960
ggagcaggac gtgagccccc gccctgcacc tctgctgtta aacacccag ccatcccttc      1020 tttcaaaagg gatcctttca taggagaaca cactgaggag atacttgaag aatttggatt      1080
```

-continued

```
cagccgcgaa gagatttatc agcttaactc agataaaatc attgaaagta ataaggtaaa    1140
agctagtctc taacttccag gcccacggct caagtgaatt tgaatactgc atttacagtg    1200
tagagtaaca cataacattg tatgcatgga aacatggagg aacagtatta cagtgtccta    1260
ccactctaat caagaaaaga attacagact ctgattctac agtgatgatt gaattctaaa    1320
aatggttatc attagggctt ttgatttata aactttggg tacttatact aaattatggt     1380
agttattctg ccttccagtt tgcttgatat atttgttgat attaagattc ttgacttata    1440
ttttgaatgg gttctagtga aaaggaatg atatattctt gaagacatcg atatacattt     1500
atttacactc ttgattctac aatgtagaaa atgaggaaat gccacaaatt gtatggtgat    1560
aaaagtcacg tgaaacaaaa aaaaaaaaaa aaaaaaaaaa aaaaaaaaaa aaaaaaaaaa    1620
a                                                                   1621
```

<210> SEQ ID NO 108
<211> LENGTH: 382
<212> TYPE: PRT
<213> ORGANISM: Homo sapien

<400> SEQUENCE: 108

```
Met Ala Leu Gln Gly Ile Ser Val Met Glu Leu Ser Gly Leu Ala Pro
 1               5                  10                  15

Gly Pro Phe Cys Ala Met Val Leu Ala Asp Phe Gly Ala Arg Val Val
                20                  25                  30

Arg Val Asp Arg Pro Gly Ser Arg Tyr Asp Val Ser Arg Leu Gly Arg
            35                  40                  45

Gly Lys Arg Ser Leu Val Leu Asp Leu Lys Gln Pro Arg Gly Ala Ala
        50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
                85                  90                  95

Arg Glu Asn Pro Arg Leu Ile Tyr Ala Arg Leu Ser Gly Phe Gly Gln
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Asp Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Ser Ser Leu Trp Glu Ala Pro Arg
        195                 200                 205

Gly Gln Asn Met Leu Asp Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
            260                 265                 270
```

```
Asp Val Phe Ala Lys Lys Thr Lys Ala Glu Trp Cys Gln Ile Phe Asp
        275                 280                 285

Gly Thr Asp Ala Cys Val Thr Pro Val Leu Thr Phe Glu Glu Val Val
        290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Leu Asn Thr Pro Ala
            325                 330                 335

Ile Pro Ser Phe Lys Arg Asp Pro Phe Ile Gly Glu His Thr Glu Glu
                340                 345                 350

Ile Leu Glu Glu Phe Gly Phe Ser Arg Glu Glu Ile Tyr Gln Leu Asn
        355                 360                 365

Ser Asp Lys Ile Ile Glu Ser Asn Lys Val Lys Ala Ser Leu
        370                 375                 380
```

<210> SEQ ID NO 109
<211> LENGTH: 1524
<212> TYPE: DNA
<213> ORGANISM: Homo sapien

<400> SEQUENCE: 109

```
ggcacgaggc tgcgccaggg cctgagcgga ggcgggggca gcctcgccag cgggggcccc      60
gggcctggcc atgcctcact gagccagcgc ctgcgcctct acctcgccga cagctggaac     120
cagtgcgacc tagtggctct cacctgcttc ctcctgggcg tgggctgccg gctgaccccg     180
ggtttgtacc acctgggccg cactgtcctc tgcatcgact tcatggtttt cacggtgcgg     240
ctgcttcaca tcttcacggt caacaaacag ctggggccca gatcgtcat cgtgagcaag     300
atgatgaagg acgtgttctt cttcctcttc ttcctcggcg tgtggctggt agcctatggc     360
gtggccacgg aggggctcct gaggccacgg gacagtgact tcccaagtat cctgcgccgc     420
gtcttctacc gtccctacct gcagatcttc gggcagattc cccaggagga catggacgtg     480
gccctcatgg agcacagcaa ctgctcgtcg gagcccggct tctgggcaca ccctcctggg     540
gcccaggcgg gcacctgcgt ctcccagtat gccaactggc tggtggtgct gctcctcgtc     600
atcttcctgc tcgtggccaa catcctgctg gtcaacttgc tcattgccat gttcagttac     660
acattcggca agtacagggg caacagcgat ctctactgga aggcgcagcg ttaccgcctc     720
atccgggaat tccactctcg gcccgcgctg gccccgccct ttatcgtcat ctcccacttg     780
cgcctcctgc tcaggcaatt gtgcaggcga ccccggagcc cccagccgtc ctccccggcc     840
ctcgagcatt tccgggttta cctttctaag gaagccgagc ggaagctgct aacgtgggaa     900
tcggtgcata aggagaactt tctgctggca cgcgctaggg acaagcggga gagcgactcc     960
gagcgtctga gcgcacgtc ccagaaggtg gacttggcac tgaaacagct gggacacatc    1020
cgcgagtacg aacagcgcct gaaagtgctg gagcggagg tccagcagtg tagccgcgtc    1080
ctggggtggg tggccgaggc cctgagccgc tctgccttgc tgccccagg tgggccgcca    1140
ccccctgacc tgcctgggtc caagactga gccctgctgg cggacttcaa ggagaagccc    1200
ccacagggga ttttgctcct agagtaaggc tcatctgggc tcggccccc gcacctggtg    1260
gccttgtcct tgaggtgagc ccatgtcca tctgggccac tgtcaggacc acctttggga    1320
gtgtcatcct tacaaaccac agcatgcccg gctcctccca gaaccagtcc cagcctggga    1380
ggatcaaggc ctggatcccg ggccgttatc catctggagg ctgcagggtc cttgggtaa    1440
cagggaccac agacccctca ccactcacag attcctcaca ctggggaaat aaagccattt    1500
```
cagaggaaaa aaaaaaaaaa aaaa                                              1524

<210> SEQ ID NO 110
<211> LENGTH: 3410
<212> TYPE: DNA
<213> ORGANISM: Homo sapien

<400> SEQUENCE: 110
gggaaccagc ctgcacgcgc tggctccggg tgacagccgc gcgcctcggc caggatctga        60
gtgatgagac gtgtccccac tgaggtgccc cacagcagca ggtgttgagc atgggctgag       120
aagctggacc ggcaccaaag ggctggcaga atgggcgcc tggctgattc ctaggcagtt       180
ggcggcagca aggaggagag gccgcagctt ctggagcaga gccgagacga agcagttctg       240
gagtgcctga acggccccct gagccctacc cgcctggccc actatggtcc agaggctgtg       300
ggtgagccgc ctgctgcggc accggaaagc ccagctcttg ctggtcaacc tgctaacctt       360
tggcctggag gtgtgtttgg ccgcaggcat cacctatgtg ccgcctctgc tgctggaagt       420
gggggtagag gagaagttca tgaccatggt gctgggcatt ggtccagtgc tgggcctggt       480
ctgtgtcccg ctcctaggct cagccagtga ccactggcgt ggacgctatg ccgccgccg        540 gcccttcatc tgggcactgt ccttgggcat cctgctgagc ctctttctca tcccaagggc       600
cggctggcta gcagggctgc tgtgcccgga tcccaggccc ctggagctgg cactgctcat       660
cctgggcgtg gggctgctgg acttctgtgg ccaggtgtgc ttcactccac tggaggccct       720
gctctctgac ctcttccggg accgggacca ctgtcgccag gcctactctg tctatgcctt       780
catgatcagt cttggggct gcctgggcta cctcctgcct gccattgact gggacaccag        840
tgccctggcc ccctacctgg gcacccagga ggagtgcctc tttggcctgc tcaccctcat       900
cttcctcacc tgcgtagcag ccacactgct ggtggctgag gaggcagcgc tgggccccac       960
cgagccagca gaagggctgt cggccccctc cttgtcgccc cactgctgtc catgccgggc      1020
ccgcttggct ttccggaacc tgggcgccct gcttccccgg ctgcaccagc tgtgctgccg      1080
catgccccgc accctgcgcc ggctcttcgt ggctgagctg tgcagctgga tggcactcat      1140
gaccttcacg ctgttttaca cggatttcgt gggcgagggg ctgtaccagg gcgtgcccag      1200
agctgagccg ggcaccgagg cccggagaca ctatgatgaa ggcgttcgga tgggcagcct      1260
ggggctgttc ctgcagtgcg ccatctccct ggtcttctct ctggtcatgg accggctggt      1320
gcagcgattc ggcactcgag cagtctattt ggccagtgtg cagcttttcc ctgtggctgc      1380
cggtgccaca tgcctgtccc acagtgtggc cgtggtgaca gcttcagccg ccctcaccgg      1440
gttcaccttc tcagccctgc agatcctgcc ctacacactg gcctccctct accaccggga      1500
gaagcaggtg ttcctgccca ataccgaggg gacactggat ggtgctagca gtgaggacag      1560
cctgatgacc agcttcctgc caggcccctaa gcctggagct cccttcccta atggacacgt      1620
gggtgctgga ggcagtggcc tgctcccacc tccacccgcg ctctgcgggg cctctgcctg      1680
tgatgtctcc gtacgtgtgg tggtgggtga gccaccgag gccagggtgg ttccgggccg       1740
gggcatctgc ctggacctcg ccatcctgga tagtgccttc ctgctgtccc aggtggcccc      1800
atccctgttt atgggctcca ttgtccagct cagccagtct gtcactgcct atatggtgtc      1860
tgccgcaggc ctgggtctgg tcgccattta ctttgctaca caggtagtat ttgacaagag      1920
cgacttggcc aaatactcag cgtagaaaac ttccagcaca ttggggtgga gggcctgcct      1980
cactgggtcc cagctccccg ctcctgttag ccccatgggg ctgccgggct ggccgccagt      2040
ttctgttgct gccaaagtaa tgtggctctc tgctgccacc ctgtgctgct gaggtgcgta      2100

```
gctgcacagc tgggggctgg ggcgtccctc tcctctctcc ccagtctcta gggctgcctg    2160
actggaggcc ttccaagggg gtttcagtct ggacttatac agggaggcca gaagggctcc    2220
atgcactgga atgcgggac tctgcaggtg gattacccag gctcagggtt aacagctagc     2280
ctcctagttg agacacacct agagaagggt ttttgggagc tgaataaact cagtcacctg    2340
gtttcccatc tctaagcccc ttaacctgca gcttcgttta atgtagctct tgcatgggag    2400
tttctaggat gaaacactcc tccatgggat ttgaacatat gacttatttg taggggaaga    2460
gtcctgaggg gcaacacaca agaaccaggt cccctcagcc cacagcactg tcttttttgct    2520 gatccacccc cctcttacct tttatcagga tgtggcctgt tggtccttct gttgccatca    2580
cagagacaca ggcatttaaa tatttaactt atttatttaa caaagtagaa gggaatccat    2640
tgctagcttt tctgtgttgg tgtctaatat ttgggtaggg tgggggatcc ccaacaatca    2700
ggtcccctga gatagctggt cattgggctg atcattgcca gaatcttctt ctcctggggt    2760
ctggcccccc aaaatgccta acccaggacc ttggaaattc tactcatccc aaatgataat    2820
tccaaatgct gttacccaag gttagggtgt tgaaggaagg tagagggtgg ggcttcaggt    2880
ctcaacggct tccctaacca cccctcttct cttggcccag cctggttccc cccacttcca    2940
ctccctctca ctctctctag gactgggctg atgaaggcac tgcccaaaat ttcccctacc    3000
cccaactttc ccctaccccc aactttcccc accagctcca caaccctgtt tggagctact    3060
gcaggaccag aagcacaaag tgcggtttcc caagcctttg tccatctcag cccccagagt    3120
atatctgtgc ttggggaatc tcacacagaa actcaggagc acccctgcc tgagctaagg     3180 gaggtcttat ctctcagggg gggtttaagt gccgtttgca ataatgtcgt cttatttatt    3240
tagcggggtg aatattttat actgtaagtg agcaatcaga gtataatgtt tatggtgaca    3300
aaattaaagg ctttcttata tgtttaaaaa aaaaaaaaa aaaaaaaaa aaaaaaaaa       3360 aaaaaaaara aaaaaaaaa aaaaaaaaa aaaaaataa aaaaaaaaa                   3410

<210> SEQ ID NO 111
<211> LENGTH: 1289
<212> TYPE: DNA
<213> ORGANISM: Homo sapien

<400> SEQUENCE: 111
agccaggcgt ccctctgcct gcccactcag tggcaacacc cgggagctgt tttgtccttt      60
gtggagcctc agcagttccc tctttcagaa ctcactgcca agagccctga acaggagcca     120
ccatgcagtg cttcagcttc attaagacca tgatgatcct cttcaatttg ctcatctttc     180
tgtgtggtgc agccctgttg gcagtgggca tctggtgtc aatcgatggg gcatcctttc      240
tgaagatctt cgggccactg tcgtccagtc ccatgcagtt tgtcaacgtg ggctacttcc     300
tcatcgcagc cggcgttgtg gtctttgctc ttggtttcct gggctgctat ggtgctaaga     360
ctgagagcaa gtgtgccctc gtgacgttct tcttcatcct cctcctcatc ttcattgctg     420
aggttgcagc tgctgtggtc gccttggtgt acaccacaat ggctgagcac ttcctgacgt     480
tgctggtagt gcctgccatc aagaaagatt atggttccca ggaagacttc actcaagtgt     540
ggaacaccac catgaaaggg ctcaagtgct gtggcttcac caactatacg gattttgagg     600
actcacccta cttcaaagag aacagtgcct ttccccatt ctgttgcaat gacaacgtca      660
ccaacacagc caatgaaacc tgcaccaagc aaaaggctca cgaccaaaaa gtagagggtt     720
gcttcaatca gcttttgtat gacatccgaa ctaatgcagt caccgtgggt ggtgtggcag    780
```

```
ctggaattgg gggcctcgag ctggctgcca tgattgtgtc catgtatctg tactgcaatc      840
tacaataagt ccacttctgc ctctgccact actgctgcca catgggaact gtgaagaggc      900
accctggcaa gcagcagtga ttgggggagg ggacaggatc taacaatgtc acttgggcca      960
gaatggacct gcccttctg  ctccagactt ggggctagat agggaccact ccttttagcg     1020
atgcctgact tccttccat  tggtgggtgg atgggtgggg ggcattccag agcctctaag     1080
gtagccagtt ctgttgccca ttcccccagt ctattaaacc cttgatatgc ccctaggcc      1140 tagtggtgat cccagtgctc tactggggga tgagagaaag gcattttata gcctgggcat     1200
aagtgaaatc agcagagcct ctgggtggat gtgtagaagg cacttcaaaa tgcataaacc     1260
tgttacaatg ttaaaaaaaa aaaaaaaaa                                       1289
```

<210> SEQ ID NO 112
<211> LENGTH: 315
<212> TYPE: PRT
<213> ORGANISM: Homo sapien

<400> SEQUENCE: 112

```
Met Val Phe Thr Val Arg Leu Leu His Ile Phe Thr Val Asn Lys Gln
 1               5                  10                  15

Leu Gly Pro Lys Ile Val Ile Val Ser Lys Met Met Lys Asp Val Phe
             20                  25                  30

Phe Phe Leu Phe Phe Leu Gly Val Trp Leu Val Ala Tyr Gly Val Ala
         35                  40                  45

Thr Glu Gly Leu Leu Arg Pro Arg Asp Ser Asp Phe Pro Ser Ile Leu
     50                  55                  60

Arg Arg Val Phe Tyr Arg Pro Tyr Leu Gln Ile Phe Gly Gln Ile Pro
 65                  70                  75                  80

Gln Glu Asp Met Asp Val Ala Leu Met Glu His Ser Asn Cys Ser Ser
                 85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Val Ile Phe
        115                 120                 125

Leu Leu Val Ala Asn Ile Leu Leu Val Asn Leu Leu Ile Ala Met Phe
    130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Ser Pro Ala Leu Glu
        195                 200                 205

His Phe Arg Val Tyr Leu Ser Lys Glu Ala Glu Arg Lys Leu Leu Thr
    210                 215                 220

Trp Glu Ser Val His Lys Glu Asn Phe Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
        275                 280                 285
```

-continued

Trp Val Ala Glu Ala Leu Ser Arg Ser Ala Leu Leu Pro Pro Gly Gly
    290                 295                 300

Pro Pro Pro Pro Asp Leu Pro Gly Ser Lys Asp
305             310                 315

<210> SEQ ID NO 113
<211> LENGTH: 553
<212> TYPE: PRT
<213> ORGANISM: Homo sapien

<400> SEQUENCE: 113

Met Val Gln Arg Leu Trp Val Ser Arg Leu Leu Arg His Arg Lys Ala
 1               5                  10                  15

Gln Leu Leu Leu Val Asn Leu Leu Thr Phe Gly Leu Glu Val Cys Leu
                20                  25                  30

Ala Ala Gly Ile Thr Tyr Val Pro Pro Leu Leu Leu Glu Val Gly Val
            35                  40                  45

Glu Glu Lys Phe Met Thr Met Val Leu Gly Ile Gly Pro Val Leu Gly
    50                  55                  60

Leu Val Cys Val Pro Leu Leu Gly Ser Ala Ser Asp His Trp Arg Gly
65                  70                  75                  80

Arg Tyr Gly Arg Arg Pro Phe Ile Trp Ala Leu Ser Leu Gly Ile
                85                  90                  95

Leu Leu Ser Leu Phe Leu Ile Pro Arg Ala Gly Trp Leu Ala Gly Leu
                100                 105                 110

Leu Cys Pro Asp Pro Arg Pro Leu Glu Leu Ala Leu Leu Ile Leu Gly
                115                 120                 125

Val Gly Leu Leu Asp Phe Cys Gly Gln Val Cys Phe Thr Pro Leu Glu
    130                 135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
                180                 185                 190

Gly Thr Gln Glu Glu Cys Leu Phe Gly Leu Leu Thr Leu Ile Phe Leu
                195                 200                 205

Thr Cys Val Ala Ala Thr Leu Leu Val Ala Glu Glu Ala Ala Leu Gly
    210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
                245                 250                 255

Leu Pro Arg Leu His Gln Leu Cys Cys Arg Met Pro Arg Thr Leu Arg
                260                 265                 270

Arg Leu Phe Val Ala Glu Leu Cys Ser Trp Met Ala Leu Met Thr Phe
    275                 280                 285

Thr Leu Phe Tyr Thr Asp Phe Val Gly Glu Gly Leu Tyr Gln Gly Val
    290                 295                 300

Pro Arg Ala Glu Pro Gly Thr Glu Ala Arg His Tyr Asp Glu Gly
305                 310                 315                 320

Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg

```
                    340                 345                 350
    Ala Val Tyr Leu Ala Ser Val Ala Ala Phe Pro Val Ala Gly Ala
                    355                 360                 365
    Thr Cys Leu Ser His Ser Val Ala Val Thr Ala Ser Ala Ala Leu
                    370                 375                 380
    Thr Gly Phe Thr Phe Ser Ala Leu Gln Ile Leu Pro Tyr Thr Leu Ala
385                 390                 395                 400
    Ser Leu Tyr His Arg Glu Lys Gln Val Phe Leu Pro Lys Tyr Arg Gly
                    405                 410                 415
    Asp Thr Gly Gly Ala Ser Ser Glu Asp Ser Leu Met Thr Ser Phe Leu
                    420                 425                 430
    Pro Gly Pro Lys Pro Gly Ala Pro Phe Pro Asn Gly His Val Gly Ala
                    435                 440                 445
    Gly Gly Ser Gly Leu Leu Pro Pro Pro Ala Leu Cys Gly Ala Ser
                    450                 455                 460
    Ala Cys Asp Val Ser Val Arg Val Val Gly Glu Pro Thr Glu Ala
465                 470                 475                 480
    Arg Val Val Pro Gly Arg Gly Ile Cys Leu Asp Leu Ala Ile Leu Asp
                    485                 490                 495
    Ser Ala Phe Leu Leu Ser Gln Val Ala Pro Ser Leu Phe Met Gly Ser
                    500                 505                 510
    Ile Val Gln Leu Ser Gln Ser Val Thr Ala Tyr Met Val Ser Ala Ala
                    515                 520                 525
    Gly Leu Gly Leu Val Ala Ile Tyr Phe Ala Thr Gln Val Val Phe Asp
                    530                 535                 540
    Lys Ser Asp Leu Ala Lys Tyr Ser Ala
545                 550

<210> SEQ ID NO 114
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
    1                   5                   10                  15
    Leu Ile Phe Leu Cys Gly Ala Ala Leu Leu Ala Val Gly Ile Trp Val
                        20                  25                  30
    Ser Ile Asp Gly Ala Ser Phe Leu Lys Ile Phe Gly Pro Leu Ser Ser
                    35                  40                  45
    Ser Ala Met Gln Phe Val Asn Val Gly Tyr Phe Leu Ile Ala Ala Gly
                50                  55                  60
    Val Val Val Phe Ala Leu Gly Phe Leu Gly Cys Tyr Gly Ala Lys Thr
65                  70                  75                  80
    Glu Ser Lys Cys Ala Leu Val Thr Phe Phe Ile Leu Leu Leu Ile
                        85                  90                  95
    Phe Ile Ala Glu Val Ala Ala Val Val Ala Leu Val Tyr Thr Thr
                        100                 105                 110
    Met Ala Glu His Phe Leu Thr Leu Leu Val Val Pro Ala Ile Lys Lys
                        115                 120                 125
    Asp Tyr Gly Ser Gln Glu Asp Phe Thr Gln Val Trp Asn Thr Thr Met
                        130                 135                 140
    Lys Gly Leu Lys Cys Cys Gly Phe Thr Asn Tyr Thr Asp Phe Glu Asp
145                     150                 155                 160
```

```
Ser Pro Tyr Phe Lys Glu Asn Ser Ala Phe Pro Pro Phe Cys Cys Asn
            165                 170                 175

Asp Asn Val Thr Asn Thr Ala Asn Glu Thr Cys Thr Lys Gln Lys Ala
            180                 185                 190

His Asp Gln Lys Val Glu Gly Cys Phe Asn Gln Leu Leu Tyr Asp Ile
            195                 200                 205

Arg Thr Asn Ala Val Thr Val Gly Gly Val Ala Ala Gly Ile Gly Gly
        210                 215                 220

Leu Glu Leu Ala Ala Met Ile Val Ser Met Tyr Leu Tyr Cys Asn Leu
225                 230                 235                 240

Gln

<210> SEQ ID NO 115
<211> LENGTH: 366
<212> TYPE: DNA
<213> ORGANISM: Homo sapien

<400> SEQUENCE: 115
gctctttctc tccctcctc tgaatttaat tctttcaact tgcaatttgc aaggattaca        60
catttcactg tgatgtatat tgtgttgcaa aaaaaaaaa gtgtctttgt ttaaaattac       120
ttggtttgtg aatccatctt gctttttccc cattggaact agtcattaac ccatctctga      180
actggtagaa aaacatctga agagctagtc tatcagcatc tgacaggtga attggatggt      240
tctcagaacc atttcaccca gacagcctgt ttctatcctg tttaataaat tagtttgggt     300
tctctacatg cataacaaac cctgctccaa tctgtcacat aaaagtctgt gacttgaagt     360
ttagtc                                                                366

<210> SEQ ID NO 116
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116
acaaagatga accatttcct atattatagc aaaattaaaa tctacccgta ttctaatatt       60
gagaaatgag atnaaacaca atnttataaa gtctacttag agaagatcaa gtgacctcaa      120
agactttact attttcatat tttaagacac atgatttatc ctattttagt aacctggttc      180
atacgttaaa caaaggataa tgtgaacagc agagaggatt tgttggcaga aaatctatgt      240
tcaatctnga actatctana tcacagacat ttctattcct tt                         282

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117
acacatgtcg cttcactgcc ttcttagatg cttctggtca acatanagga acagggacca       60
tatttatcct ccctcctgaa acaattgcaa ataanacaa atatatgaa acaattgcaa       120 aataaggcaa atatatgaa acaacaggtc tcgagatatt ggaaatcagt caatgaagga      180
```

```
tactgatccc tgatcactgt cctaatgcag gatgtgggaa acagatgagg tcacctctgt    240
gactgcccca gcttactgcc tgtagagagt ttctangctg cagttcagac agggagaaat    300
tgggt                                                                305
```

<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118

```
accaaggtgt ntgaatctct gacgtgggga tctctgattc ccgcacaatc tgagtggaaa     60
aantcctggg t                                                          71
```

<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119

```
actccggttg gtgtcagcag cacgtggcat tgaacatngc aatgtggagc ccaaaccaca     60
gaaaatgggg tgaaattggc caactttcta tnaacttatg ttggcaantt tgccaccaac   120
agtaagctgg cccttctaat aaagaaaat tgaaaggttt ctcactaanc ggaattaant    180
aatggantca aganactccc aggcctcagc gt                                  212
```

<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120

```
actcgttgca natcaggggc cccccagagt caccgttgca ggagtccttc tggtcttgcc     60
ctccgccggc gcagaacatg ctggggtggt                                      90
```

<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121

```
tgtancgtga anacgacaga nagggttgtc aaaaatggag aanccttgaa gtcattttga     60
gaataagatt tgctaaaaga tttggggcta aaacatggtt attgggagac atttctgaag   120
atatncangt aaattangga atgaattcat ggttctttg ggaattcctt tacgatngcc    180
agcatanact tcatgtgggg atancagcta cccttgta                            218
```

<210> SEQ ID NO 122
<211> LENGTH: 171
<212> TYPE: DNA
<213> ORGANISM: Homo sapien

<400> SEQUENCE: 122

```
tagggtgta tgcaactgta aggacaaaaa ttgagactca actggcttaa ccaataaagg      60
catttgttag ctcatggaac aggaagtcgg atggtggggc atcttcagtg ctgcatgagt    120
caccaccccg gcggggtcat ctgtgccaca ggtccctgtt gacagtgcgg t             171
```

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123

```
tgtagcgtga agacnacaga atggtgtgtg ctgtgctatc caggaacaca tttattatca     60
ttatcaanta ttgtgt                                                     76
```

<210> SEQ ID NO 124
<211> LENGTH: 131
<212> TYPE: DNA
<213> ORGANISM: Homo sapien

<400> SEQUENCE: 124

```
acctttcccc aaggccaatg tcctgtgtgc taactggccg gctgcaggac agctgcaatt     60
caatgtgctg ggtcatatgg agggaggag actctaaaat agccaattt attctcttgg     120 ttaagatttg t                                                         131
```

<210> SEQ ID NO 125
<211> LENGTH: 432
<212> TYPE: DNA
<213> ORGANISM: Homo sapien

<400> SEQUENCE: 125

```
actttatcta ctggctatga aatagatggt ggaaaattgc gttaccaact ataccactgg     60
cttgaaaaag aggtgatagc tcttcagagg acttgtgact tttgctcaga tgctgaagaa   120
ctacagtctg catttggcag aaatgaagat gaatttggat taaatgagga tgctgaagat   180
ttgcctcacc aaacaaaagt gaacaactg agagaaaatt tcaggaaaa aagacagtgg     240 ctcttgaagt atcagtcact tttgagaatg tttcttagtt actgcatact tcatggatcc   300
catggtgggg gtcttgcatc tgtaagaatg gaattgattt tgcttttgca agaatctcag   360
caggaaacat cagaaccact attttctagc cctctgtcag agcaaacctc agtgcctctc   420
ctctttgctt gt                                                       432
```

<210> SEQ ID NO 126
<211> LENGTH: 112
<212> TYPE: DNA
<213> ORGANISM: Homo sapien

<400> SEQUENCE: 126

```
acacaacttg aatagtaaaa tagaaactga gctgaaattt ctaattcact ttctaaccat     60
agtaagaatg atatttcccc ccagggatca ccaaatattt ataaaaattt gt            112
```

<210> SEQ ID NO 127
<211> LENGTH: 54
<212> TYPE: DNA
<213> ORGANISM: Homo sapien

<400> SEQUENCE: 127

```
accacgaaac cacaaacaag atggaagcat caatccactt gccaagcaca gcag         54
```

<210> SEQ ID NO 128
<211> LENGTH: 323
<212> TYPE: DNA
<213> ORGANISM: Homo sapien

<400> SEQUENCE: 128

```
acctcattag taattgtttt gttgtttcat ttttttctaa tgtctcccct ctaccagctc   60
acctgagata acagaatgaa aatggaagga cagccagatt tctcctttgc tctctgctca  120
ttctctctga agtctaggtt acccattttg gggacccatt ataggcaata aacacagttc  180
ccaaagcatt tggacagttt cttgttgtgt tttagaatgg ttttccttt tcttagcctt   240
ttcctgcaaa aggctcactc agtcccttgc ttgctcagtg gactgggctc cccagggcct  300
aggctgcctt cttttccatg tcc                                          323
```

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129

```
acatacatgt gtgtatattt ttaaatatca cttttgtatc actctgactt tttagcatac   60
tgaaaacaca ctaacataat ttntgtgaac catgatcaga tacaacccaa atcattcatc  120
tagcacattc atctgtgata naaagatagg tgagtttcat ttccttcacg ttggccaatg  180
gataaacaaa gt                                                      192
```

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130

```
cccttttta tggaatgagt agactgtatg tttgaanatt tanccacaac ctctttgaca    60
tataatgacg caacaaaaag gtgctgttta gtcctatggt tcagtttatg cccctgacaa  120
gtttccattg tgttttgccg atcttctggc taatcgtggt atcctccatg ttattagtaa  180
ttctgtattc cattttgtta acgcctggta gatgtaacct gctangaggc taactttata  240
cttatttaaa agctcttatt ttgtggtcat taaaatggca atttatgtgc agcactttat  300
tgcagcagga agcacgtgtg ggttggttgt aaagctcttt gctaatctta aaaagtaatg  360
gg                                                                 362
```

<210> SEQ ID NO 131
<211> LENGTH: 332

```
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131 cttttttgaaa gatcgtgtcc actcctgtgg acatcttgtt ttaatggagt ttcccatgca      60
gtangactgg tatggttgca gctgtccaga taaaaacatt tgaagagctc caaaatgaga     120
gttctcccag gttcgccctg ctgctccaag tctcagcagc agcctctttt aggaggcatc     180
ttctgaacta gattaaggca gcttgtaaat ctgatgtgat ttggtttatt atccaactaa     240
cttccatctg ttatcactgg agaaagccca gactccccan gacnggtacg gattgtgggc     300
atanaaggat tgggtgaagc tggcgttgtg gt                                   332

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132
acttttgcca ttttgtatat ataaacaatc ttgggacatt ctcctgaaaa ctaggtgtcc      60
agtggctaag agaactcgat ttcaagcaat tctgaaagga aaaccagcat gacacagaat     120
ctcaaattcc caaacagggg ctctgtggga aaatgagggg aggacctttg tatctcgggt     180
tttagcaagt taaaatgaan atgacaggaa aggcttattt atcaacaaag agaagagttg     240
ggatgcttct aaaaaaaact ttggtagaga aaataggaat gctnaatcct agggaagcct     300
gtaacaatct acaattggtc ca                                              322

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 133
acaagccttc acaagtttaa ctaaattggg attaatcttt ctgtanttat ctgcataatt      60
cttgtttttc tttccatctg gctcctgggt tgacaatttg tggaaacaac tctattgcta     120
ctatttaaaa aaaatcacaa atctttccct ttaagctatg ttnaattcaa actattcctg     180
ctattcctgt tttgtcaaag aaattatatt tttcaaaata tgtntatttg tttgatgggt     240
cccacgaaac actaataaaa accacagaga ccagcctg                             278

<210> SEQ ID NO 134
<211> LENGTH: 121
<212> TYPE: DNA
<213> ORGANISM: Homo sapien
<220> FEATURE:
<221> NAME/KEY: misc_feature
<222> LOCATION: (1)...(121)
<223> OTHER INFORMATION: n = A,T,C or G

<400> SEQUENCE: 134
```

```
gtttanaaaa cttgtttagc tccatagagg aaagaatgtt aaactttgta ttttaaaaca      60
tgattctctg aggttaaact tggttttcaa atgttatttt tacttgtatt ttgcttttgg     120
t                                                                    121

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 135
acttanaacc atgcctagca catcagaatc cctcaaagaa catcagtata atcctatacc      60
atancaagtg gtgactggtt aagcgtgcga caaaggtcag ctggcacatt acttgtgtgc     120
aaacttgata cttttgttct aagtaggaac tagtatacag tncctaggan tggtactcca    180
gggtgccccc caactcctgc agccgctcct ctgtgccagn ccctgnaagg aactttcgct    240
ccacctcaat caagccctgg gccatgctac ctgcaattgg ctgaacaaac gtttgctgag    300
ttcccaagga tgcaaagcct ggtgctcaac tcctggggcg tcaactcagt                350

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 136
tgtaccgtga agacgacaga agttgcatgg cagggacagg gcagggccga ggccagggtt      60
gctgtgattg tatccgaata ntcctcgtga gaaaagataa tgagatgacg tgagcagcct    120
gcagacttgt gtctgccttc aanaagccag acaggaaggc cctgcctgcc ttggctctga    180
cctggcggcc agccagccag ccacaggtgg gcttcttcct tttgtggtga caacnccaag    240
aaaactgcag aggcccaggg tcaggtgtna gtgggtangt gaccataaaa caccaggtgc    300
tcccaggaac ccgggcaaag gccatcccca cctacagcca gcatgcccac tggcgtgatg    360
ggtgcagang gatgaagcag ccagntgttc tgctgtggt                           399

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137
actggtgtgg tngggggtga tgctggtggt anaagttgan gtgacttcan gatggtgtgt      60
ggaggaagtg tgtgaacgta gggatgtaga ngttttggcc gtgctaaatg agcttcggga    120
ttggctggtc ccactggtgg tcactgtcat tggtggggtt cctgt                    165

<210> SEQ ID NO 138
<211> LENGTH: 338
<212> TYPE: DNA
<213> ORGANISM: Homo sapien
```

```
<220> FEATURE:
<221> NAME/KEY: misc_feature
<222> LOCATION: (1)...(338)
<223> OTHER INFORMATION: n = A,T,C or G

<400> SEQUENCE: 138
actcactgga atgccacatt cacaacagaa tcagaggtct gtgaaaacat taatggctcc      60
ttaacttctc cagtaagaat cagggacttg aaatggaaac gttaacagcc acatgcccaa     120
tgctgggcag tctcccatgc cttccacagt gaaagggctt gagaaaaatc acatccaatg    180
tcatgtgttt ccagccacac caaaaggtgc ttggggtgga gggctggggg catananggt    240
cangcctcag gaagcctcaa gttccattca gctttgccac tgtacattcc ccatntttaa    300
aaaaactgat gccttttttt tttttttttg taaaattc                             338

<210> SEQ ID NO 139
<211> LENGTH: 382
<212> TYPE: DNA
<213> ORGANISM: Homo sapien

<400> SEQUENCE: 139
gggaatcttg gttttttggca tctggttttgc ctatagccga ggccactttg acagaacaaa   60
gaaagggact tcgagtaaga aggtgattta cagccagcct agtgcccgaa gtgaaggaga   120
attcaaacag acctcgtcat tcctggtgtg agcctggtcg gctcaccgcc tatcatctgc    180
atttgcctta ctcaggtgct accggactct ggccctgat gtctgtagtt tcacaggatg    240
ccttatttgt cttctacacc ccacagggcc ccctacttct tcggatgtgt ttttaataat    300
gtcagctatg tgccccatcc tccttcatgc cctccctccc tttcctacca ctgctgagtg    360
gcctggaact tgtttaaagt gt                                              382

<210> SEQ ID NO 140
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140
accaaanctt ctttctgttg tgttngattt tactataggg gtttngcttn ttctaaanat      60
acttttcatt taacancttt tgttaagtgt caggctgcac tttgctccat anaattattg    120
ttttcacatt tcaacttgta tgtgtttgtc tcttanagca ttggtgaaat cacatatttt    180
atattcagca taaggagaa                                                  200

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G

<400> SEQUENCE: 141
actttatttt caaaacactc atatgttgca aaaacacat agaaaaataa agtttggtgg       60
gggtgctgac taaacttcaa gtcacagact tttatgtgac agattggagc agggtttgtt    120
atgcatgtag agaacccaaa ctaatttatt aaacaggata gaaacaggct gtctgggtga    180
```

```
aatggttctg agaaccatcc aattcacctg tcagatgctg atanactagc tcttcagatg      240
tttttctacc agttcagaga tnggttaatg actanttcca atggggaaaa agcaagatgg      300
attcacaaac caagtaattt taaacaaaga cactt                                 335
```

<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142

```
accaggttaa tattgccaca tatatccttt ccaattgcgg gctaaacaga cgtgtattta      60
gggttgttta aagacaaccc agcttaatat caagagaaat tgtgaccttt catggagtat     120
ctgatggaga aaacactgag ttttgacaaa tcttatttta ttcagatagc agtctgatca     180
cacatggtcc aacaacactc aaataataaa tcaaatatna tcagatgtta aagattggtc     240
ttcaaacatc atagccaatg atgccccgct tgcctataat ctctccgaca taaaaccaca    300
tcaacacctc agtggccacc aaaccattca gcacagcttc cttaactgtg agctgtttga    360
agctaccagt ctgagcacta ttgactatnt ttttcangct ctgaatagct ctaggggatct   420 cagcangggt gggaggaacc agctcaacct tggcgtant                             459
```

<210> SEQ ID NO 143
<211> LENGTH: 140
<212> TYPE: DNA
<213> ORGANISM: Homo sapien

<400> SEQUENCE: 143

```
acatttcctt ccaccaagtc aggactcctg gcttctgtgg gagttcttat cacctgaggg      60
aaatccaaac agtctctcct agaaaggaat agtgtcacca accccaccca tctccctgag    120
accatccgac ttccctgtgt                                                  140
```

<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144

```
acttcagtaa caacatacaa taacaacatt aagtgtatat tgccatcttt gtcattttct      60
atctatacca ctctcccttc tgaaaacaan aatcactanc caatcactta tacaaatttg    120
aggcaattaa tccatatttg ttttcaataa ggaaaaaaag atgt                       164
```

<210> SEQ ID NO 145
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 145

```
acgtagacca tccaactttg tatttgtaat ggcaaacatc cagnagcaat tcctaaacaa      60
```

```
actggagggt atttataccc aattatccca ttcattaaca tgccctcctc ctcaggctat      120
gcaggacagc tatcataagt cggcccaggc atccagatac taccatttgt ataaacttca      180 gtagggagt  ccatccaagt gacaggtcta atcaaaggag gaaatggaac ataagcccag      240
tagtaaaatn ttgcttagct gaaacagcca caaaagactt accgccgtgg tgattaccat      300
caa                                                                    303
```

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146

```
actgcagctc aattagaagt ggtctctgac tttcatcanc ttctccctgg gctccatgac       60
actggcctgg agtgactcat tgctctggtt ggttgagaga gctcctttgc caacaggcct      120
ccaagtcagg gctgggattt gtttcctttc cacattctag caacaatatg ctggccactt      180
cctgaacagg gagggtggga ggagccagca tggaacaagc tgccactttc taaagtagcc      240
agacttgccc ctgggcctgt cacacctact gatgaccttc tgtgcctgca ggatggaatg      300 tagggtgag  ctgtgtgact ctatggt                                          327
```

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)
<223> OTHER INFORMATION: n = A,T,C or G

<400> SEQUENCE: 147

```
acattgtttt tttgagataa agcattgana gagctctcct taacgtgaca caatggaagg       60
actggaacac atacccacat ctttgttctg agggataatt ttctgataaa gtcttgctgt      120
atattcaagc acatatgtta tatattattc agttccatgt ttatagccta gtt             173
```

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148

```
acaaccactt tatctcatcg aattttaac  ccaaactcac tcactgtgcc tttctatcct       60
atgggatata ttatttgatg ctccatttca tcacacatat atgaataata cactcatact      120
gccctactac ctgctgcaat aatcacattc ccttcctgtc ctgaccctga agccattggg      180
gtggtcctag tggccatcag tccangcctg caccttgagc cctgagctc  cattgctcac      240 nccancccac ctcaccgacc ccatcctctt acacagctac ctccttgctc tctaaccccca     300 tagattatnt ccaaattcag tcaattaagt tactattaac actctaccg  acatgtccag      360 caccactggt aagccttctc cagccaacac acacacacac acncacac   acacacatat      420
```

-continued ccaggcacag gctacctcat cttcacaatc acccctttaa ttaccatgct atggtgg        477

<210> SEQ ID NO 149
<211> LENGTH: 207
<212> TYPE: DNA
<213> ORGANISM: Homo sapien

<400> SEQUENCE: 149
acagttgtat tataatatca agaaataaac ttgcaatgag agcatttaag agggaagaac        60
taacgtattt tagagagcca aggaaggttt ctgtggggag tgggatgtaa ggtgggcct       120 gatgataaat aagagtcagc caggtaagtg ggtggtgtgg tatgggcaca gtgaagaaca      180
tttcaggcag agggaacagc agtgaaa                                          207

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150
accttgattt cattgctgct ctgatggaaa cccaactatc taatttagct aaaacatggg        60
cacttaaatg tggtcagtgt ttggacttgt taactantgg catctttggg t               111

<210> SEQ ID NO 151
<211> LENGTH: 196
<212> TYPE: DNA
<213> ORGANISM: Homo sapien

<400> SEQUENCE: 151
agcgcggcag gtcatattga acattccaga tacctatcat tactcgatgc tgttgataac        60
agcaagatgg ctttgaactc agggtcacca ccagctattg gaccttacta tgaaaaccat      120
ggataccaac cggaaaaccc ctatcccgca cagcccactg tggtccccac tgtctacgag      180
gtgcatccgg ctcagt                                                      196

<210> SEQ ID NO 152
<211> LENGTH: 132
<212> TYPE: DNA
<213> ORGANISM: Homo sapien

<400> SEQUENCE: 152
acagcacttt cacatgtaag aagggagaaa ttcctaaatg taggagaaag ataacagaac        60 cttcccctttt tcatctagtg gtggaaacct gatgctttat gttgacagga atagaaccag     120
gagggagttt gt                                                          132

<210> SEQ ID NO 153
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 153
acaanaccca nganaggcca ctggccgtgg tgtcatggcc tccaaacatg aaagtgtcag        60
cttctgctct tatgtcctca tctgacaact ctttaccatt tttatcctcg ctcagcagga     120

```
gcacatcaat aaagtccaaa gtcttggact tggccttggc ttggaggaag tcatcaacac      180
cctggctagt gagggtgcgg cgccgctcct ggatgacggc atctgtgaag tcgtgcacca      240
gtctgcaggc cctgtggaag cgccgtccac acggagtnag gaatt                     285

<210> SEQ ID NO 154
<211> LENGTH: 333
<212> TYPE: DNA
<213> ORGANISM: Homo sapien

<400> SEQUENCE: 154
accacagtcc tgttgggcca gggcttcatg acccttctg tgaaaagcca tattatcacc       60
accccaaatt tttccttaaa tatctttaac tgaaggggtc agcctcttga ctgcaaagac     120
cctaagccgg ttacacagct aactcccact ggccctgatt tgtgaaattg ctgctgcctg     180
attggcacag gagtcgaagg tgttcagctc ccctcctccg tggaacgaga ctctgatttg     240
agtttcacaa attctcgggc cacctcgtca ttgctcctct gaaataaaat ccggagaatg     300
gtcaggcctg tctcatccat atggatcttc cgg                                  333

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155
actggaaata ataaaaccca catcacagtg ttgtgtcaaa gatcatcagg gcatggatgg       60
gaaagtgctt tgggaactgt aaagtgccta acacatgatc gatgattttt gttataatat     120
ttgaatcacg gtgcatacaa actctcctgc ctgctcctcc tgggcccag ccccagcccc      180 atcacagctc actgctctgt tcatccaggc ccagcatgta gtggctgatt cttcttggct     240
gcttttagcc tccanaagtt tctctgaagc caaccaaacc tctangtgta aggcatgctg     300
gccctggt                                                              308

<210> SEQ ID NO 156
<211> LENGTH: 295
<212> TYPE: DNA
<213> ORGANISM: Homo sapien

<400> SEQUENCE: 156
accttgctcg gtgcttggaa catattagga actcaaaata tgagatgata acagtgccta       60
ttattgatta ctgagagaac tgttagacat ttagttgaag attttctaca caggaactga     120
gaataggaga ttatgtttgg ccctcatatt ctctcctatc ctccttgcct cattctatgt     180
ctaatatatt ctcaatcaaa taaggttagc ataatcagga aatcgaccaa ataccaatat     240
aaaaccagat gtctatcctt aagattttca aatagaaaac aaattaacag actat          295

<210> SEQ ID NO 157
<211> LENGTH: 126
<212> TYPE: DNA
<213> ORGANISM: Homo sapien

<400> SEQUENCE: 157
acaagtttaa atagtgctgt cactgtgcat gtgctgaaat gtgaaatcca ccacatttct       60
```

```
gaagagcaaa acaaattctg tcatgtaatc tctatcttgg gtcgtgggta tatctgtccc    120
cttagt                                                               126
```

<210> SEQ ID NO 158
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158

```
acccactggt cttggaaaca cccatcctta atacgatgat ttttctgtcg tgtgaaaatg    60
aanccagcag gctgcccta gtcagtcctt ccttccagag aaaaagagat ttgagaaagt    120
gcctgggtaa ttcaccatta atttcctccc ccaaactctc tgagtcttcc cttaatattt    180
ctggtggttc tgaccaaagc aggtcatggt ttgttgagca tttgggatcc cagtgaagta    240
natgtttgta gccttgcata cttagcccct cccacgcaca aacggagtgg cagagtggtg    300
ccaaccctgt tttcccagtc cacgtagaca gattcacagt gcggaattct ggaagctgga    360
nacagacggg ctctttgcag agccgggact ctgagangga catgagggcc tctgcctctg    420
tgttcattct ctgatgtcct gt                                             442
```

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159

```
acttccaggt aacgttgttg tttccgttga gcctgaactg atgggtgacg ttgtaggttc    60
tccaacaaga actgaggttg cagagcgggt agggaagagt gctgttccag ttgcacctgg   120
gctgctgtgg actgttgttg attcctcact acggcccaag gttgtggaac tggcanaaag   180
gtgtgttgtt gganttgagc tcgggcggct gtggtaggtt gtgggctctt caacaggggc   240
tgctgtggtg ccgggangtg aangtgttgt gtcacttgag cttggccagc tctggaaagt   300
antanattct tcctgaaggc cagcgcttgt ggagctggca ngggtcantg ttgtgtgtaa   360
cgaaccagtg ctgctgtggg tgggtgtana tcctccacaa agcctgaagt tatggtgtcn   420
tcaggtaana atgtggtttc agtgtccctg ggcngctgtg aaggttgta nattgtcacc   480 aagggaataa gctgtggt                                                 498
```

<210> SEQ ID NO 160
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 160

```
acctgcatcc agcttccctg ccaaactcac aaggagacat caacctctag acagggaaac    60
agcttcagga tacttccagg agacagagcc accagcagca aaacaaatat tcccatgcct   120
ggagcatggc atagaggaag ctganaaatg tggggtctga ggaagccatt tgagtctggc   180
```

```
cactagacat ctcatcagcc acttgtgtga agagatgccc catgacccca gatgcctctc    240
ccacccttac ctccatctca cacacttgag ctttccactc tgtataattc taacatcctg    300
gagaaaaatg gcagtttgac cgaacctgtt cacaacggta gaggctgatt tctaacgaaa    360
cttgtagaat gaagcctgga                                                 380

<210> SEQ ID NO 161
<211> LENGTH: 114
<212> TYPE: DNA
<213> ORGANISM: Homo sapien

<400> SEQUENCE: 161
actccacatc ccctctgagc aggcggttgt cgttcaaggt gtatttggcc ttgcctgtca     60
cactgtccac tggcccctta tccacttggt gcttaatccc tcgaaagagc atgt          114

<210> SEQ ID NO 162
<211> LENGTH: 177
<212> TYPE: DNA
<213> ORGANISM: Homo sapien

<400> SEQUENCE: 162
actttctgaa tcgaatcaaa tgatacttag tgtagtttta atatcctcat atatatcaaa     60
gttttactac tctgataatt ttgtaaacca ggtaaccaga acatccagtc atacagcttt    120
tggtgatata taacttggca ataacccagt ctggtgatac ataaaactac tcactgt      177

<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 163
catttataca gacaggcgtg aagacattca cgacaaaaac gcgaaattct atcccgtgac     60
canagaaggc agctacggct actcctacat cctggcgtgg gtggccttcg cctgcacctt    120
catcagcggc atgatgt                                                    137

<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 164
cttatcacaa tgaatgttct cctgggcagc gttgtgatct ttgccacctt cgtgacttta     60
tgcaatgcat catgctattt catacctaat gagggagttc caggagattc aaccaggaaa    120
tgcatggatc tcaaaggaaa caaacaccca ataaactcgg agtggcagac tgacaactgt    180
gagacatgca cttgctacga aacagaaatt tcatgttgca cccttgtttc tacacctgtg    240
ggttatgaca agacaactg ccaaagaatc ttcaagaagg aggactgcaa gtatatcgtg    300
gtggagaaga aggacccaaa aaagacctgt tctgtcagtg aatggataat ctaatgtgct    360
tctagtaggc acagggctcc caggccaggc ctcattctcc tctggcctct aatagtcaat    420
```

```
gattgtgtag ccatgcctat cagtaaaaag atntttgagc aaacacttt           469
```

<210> SEQ ID NO 165
<211> LENGTH: 195
<212> TYPE: DNA
<213> ORGANISM: Homo sapien
<220> FEATURE:
<221> NAME/KEY: misc_feature
<222> LOCATION: (1)...(195)
<223> OTHER INFORMATION: n = A,T,C or G

<400> SEQUENCE: 165

```
acagttttt  atanatatcg  acattgccgg  cacttgtgtt  cagtttcata  aagctggtgg    60
atccgctgtc  atccactatt  ccttggctag  agtaaaaatt  attcttatag  cccatgtccc   120
tgcaggccgc  ccgcccgtag  ttctcgttcc  agtcgtcttg  gcacacaggg  tgccaggact  180
tcctctgaga  tgagt                                                         195
```

<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166

```
acatcttagt  agtgtggcac  atcaggggc   catcagggtc  acagtcactc  atagcctcgc    60
cgaggtcgga  gtccacacca  ccggtgtagg  tgtgctcaat  cttgggcttg  gcgcccacct  120
ttggagaagg  gatatgctgc  acacacatgt  ccacaaagcc  tgtgaactcg  ccaaagaatt  180
tttgcagacc  agcctgagca  agggcggat   gttcagcttc  agctcctcct  tcgtcaggtg  240
gatgccaacc  tcgtctangg  tccgtgggaa  gctggtgtcc  acntcaccta  caacctgggc  300
gangatctta  taaagaggct  ccnagataaa  ctccacgaaa  cttctctggg  agctgctagt  360
ngggccttt   ttggtgaact  ttc                                              383
```

<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167

```
acagagccag  accttggcca  taaatgaanc  agagattaag  actaaacccc  aagtcganat    60
tggagcagaa  actggagcaa  gaagtgggcc  tggggctgaa  gtagagacca  aggccactgc  120
tatanccata  cacagagcca  actctcaggc  caaggcnatg  gttggggcag  anccagagac  180
tcaatctgan  tccaaagtgg  tggctggaac  actggtcatg  acanaggcag  tgactctgac  240
tgangtc                                                                   247
```

<210> SEQ ID NO 168
<211> LENGTH: 273
<212> TYPE: DNA
<213> ORGANISM: Homo sapien
<220> FEATURE:
<221> NAME/KEY: misc_feature
<222> LOCATION: (1)...(273)
<223> OTHER INFORMATION: n = A,T,C or G

<400> SEQUENCE: 168

```
acttctaagt tttctagaag tggaaggatt gtantcatcc tgaaaatggg tttacttcaa      60
aatccctcan ccttgttctt cacnactgtc tatactgana gtgtcatgtt tccacaaagg    120
gctgacacct gagcctgnat tttcactcat ccctgagaag ccctttccag tagggtgggc    180
aattcccaac ttccttgcca caagcttccc aggctttctc ccctggaaaa ctccagcttg    240
agtcccagat acactcatgg gctgccctgg gca                                  273
```

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169

```
acagccttgg cttccccaaa ctccacagtc tcagtgcaga aagatcatct tccagcagtc      60
agctcagacc agggtcaaag gatgtgacat caacagtttc tggtttcaga acaggttcta    120
ctactgtcaa atgacccccc atacttcctc aaaggctgtg gtaagttttg cacaggtgag    180
ggcagcagaa agggggtant tactgatgga caccatcttc tctgtatact ccacactgac    240
cttgccatgg gcaaaggccc ctaccacaaa acaatagga tcactgctgg gcaccagctc     300
acgcacatca ctgacaaccg ggatggaaaa agaantgcca actttcatac atccaactgg    360
aaagtgatct gatactggat tcttaattac cttcaaaagc ttctggggc catcagctgc     420
tcgaacactg a                                                          431
```

<210> SEQ ID NO 170
<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170

```
acctgtgggc tgggctgtta tgcctgtgcc ggctgctgaa agggagttca gaggtggagc      60
tcaaggagct ctgcaggcat tttgccaanc ctctccanag canagggagc aacctacact    120
ccccgctaga aagacaccag attggagtcc tgggaggggg agttggggtg gcatttgat     180
gtatacttgt cacctgaatg aangagccag agaggaanga gacgaaatg anattggcct    240
tcaaagctag gggtctggca ggtgga                                          266
```

<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171

```
ggcagccaaa tcataaacgg cgaggactgc agcccgcact cgcagccctg gcaggcggca      60
ctggtcatgg aaaacgaatt gttctgctcg ggcgtcctgg tgcatccgca gtgggtgctg    120
```

-continued

```
tcagccgcac actgtttcca gaagtgagtg cagagctcct acaccatcgg gctgggcctg      180
cacagtcttg aggccgacca agagccaggg agccagatgg tggaggccag cctctccgta      240
cggcacccag agtacaacag acccttgctc gctaacgacc tcatgctcat caagttggac      300
gaatccgtgt ccgagtctga caccatccgg agcatcagca ttgcttcgca gtgccctacc      360
gcggggaact cttgcctcgt ttctggctgg ggtctgctgg cgaacggcag aatgcctacc      420
gtgctgcagt gcgtgaacgt gtcggtggtg tctgaggagg tctgcagtaa gctctatgac      480
ccgctgtacc accccagcat gttctgcgcc ggcggagggc aagaccagaa ggactcctgc      540
aacggtgact ctggggggcc cctgatctgc aacgggtact gcagggcct tgtgtctttc       600
ggaaaagccc cgtgtggcca agttggcgtg ccaggtgtct acaccaacct ctgcaaattc      660
actgagtgga tagagaaaac cgtccaggcc agttaactct ggggactggg aacccatgaa      720
attgaccccc aaatacatcc tgcggaagga attcaggaat atctgttccc agcccctcct      780
ccctcaggcc caggagtcca ggcccccagc ccctcctccc tcaaaccaag ggtacagatc      840
cccagcccct cctccctcag acccaggagt ccagaccccc cagcccctcc tccctcagac      900
ccaggagtcc agccctcct ccctcagacc caggagtcca gaccccccag cccctcctcc       960
ctcagaccca gggtccagg ccccaaccc ctcctccctc agactcagag gtccaagccc       1020
ccaaccntc attccccaga cccagaggtc caggtcccag cccctcntcc ctcagaccca      1080
gcggtccaat gccacctaga ctntccctgt acacagtgcc cccttgtggc acgttgaccc      1140
aaccttacca gttggttttt catttttngt ccctttcccc tagatccaga aataaagttt      1200
aagagaagng caaaaaaaa aaaaaaaaa aaaaaaaaa aaaaaaaa                      1248
```

<210> SEQ ID NO 172
<211> LENGTH: 159
<212> TYPE: PRT
<213> ORGANISM: Homo sapien
<220> FEATURE:
<221> NAME/KEY: VARIANT
<222> LOCATION: (1)...(159)
<223> OTHER INFORMATION: Xaa = Any Amino Acid

<400> SEQUENCE: 172

```
Met Val Glu Ala Ser Leu Ser Val Arg His Pro Glu Tyr Asn Arg Pro
 1               5                  10                  15

Leu Leu Ala Asn Asp Leu Met Leu Ile Lys Leu Asp Glu Ser Val Ser
            20                  25                  30

Glu Ser Asp Thr Ile Arg Ser Ile Ser Ile Ala Ser Gln Cys Pro Thr
        35                  40                  45

Ala Gly Asn Ser Cys Leu Val Ser Gly Trp Gly Leu Leu Ala Asn Gly
    50                  55                  60

Arg Met Pro Thr Val Leu Gln Cys Val Asn Val Ser Val Val Ser Glu
65                  70                  75                  80

Glu Val Cys Ser Lys Leu Tyr Asp Pro Leu Tyr His Pro Ser Met Phe
                85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125

Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

<210> SEQ ID NO 173
<211> LENGTH: 1265
<212> TYPE: DNA
<213> ORGANISM: Homo sapien
<220> FEATURE:
<221> NAME/KEY: misc_feature
<222> LOCATION: (1)...(1265)
<223> OTHER INFORMATION: n = A,T,C or G

<400> SEQUENCE: 173

| | | | | | |
|---|---|---|---|---|---|
| ggcagcccgc | actcgcagcc | ctggcaggcg | gcactggtca | tggaaaacga | attgttctgc | 60 |
| tcgggcgtcc | tggtgcatcc | gcagtgggtg | ctgtcagccg | cacactgttt | ccagaactcc | 120 |
| tacaccatcg | ggctgggcct | gcacagtctt | gaggccgacc | aagagccagg | gagccagatg | 180 |
| gtggaggcca | gcctctccgt | acggcaccca | gagtacaaca | gacccttgct | cgctaacgac | 240 |
| ctcatgctca | tcaagttgga | cgaatccgtg | tccgagtctg | acaccatccg | gagcatcagc | 300 |
| attgcttcgc | agtgccctac | cgcggggaac | tcttgcctcg | tttctggctg | gggtctgctg | 360 |
| gcgaacggtg | agctcacggg | tgtgtgtctg | ccctcttcaa | ggaggtcctc | tgcccagtcg | 420 |
| cgggggctga | cccagagctc | tgcgtcccag | gcagaatgcc | taccgtgctg | cagtgcgtga | 480 |
| acgtgtcggt | ggtgtctgag | gaggtctgca | gtaagctcta | tgaccgctg | taccacccca | 540 |
| gcatgttctg | cgccggcgga | gggcaagacc | agaaggactc | ctgcaacggt | gactctgggg | 600 |
| ggcccctgat | ctgcaacggg | tacttgcagg | gccttgtgtc | tttcggaaaa | gccccgtgtg | 660 |
| gccaagttgg | cgtgccaggt | gtctacacca | acctctgcaa | attcactgag | tggatagaga | 720 |
| aaaccgtcca | ggccagttaa | ctctggggac | tgggaaccca | tgaaattgac | ccccaaatac | 780 |
| atcctgcgga | aggaattcag | gaatatctgt | tcccagcccc | tcctccctca | ggcccaggag | 840 |
| tccaggcccc | cagcccctcc | tccctcaaac | caagggtaca | gatccccagc | ccctcctccc | 900 |
| tcagacccag | gagtccagac | ccccagccc | ctcctccctc | agacccagga | gtccagcccc | 960 |
| tcctccntca | gacccaggag | tccagacccc | ccagcccctc | ctccctcaga | cccaggggtt | 1020 |
| gaggccccca | acccctcctc | cttcagagtc | agaggtccaa | gcccccaacc | cctcgttccc | 1080 |
| cagacccaga | ggtnnaggtc | ccagcccctc | ttccntcaga | cccagnggtc | caatgccacc | 1140 |
| tagattttcc | ctgnacacag | tgccccttg | tggnangttg | acccaacctt | accagttggt | 1200 |
| ttttcatttt | tngtcccttt | ccctagatc | cagaaataaa | gtttaagaga | ngngcaaaaa | 1260 |
| aaaaa | | | | | | 1265 |

<210> SEQ ID NO 174
<211> LENGTH: 1459
<212> TYPE: DNA
<213> ORGANISM: Homo sapien
<220> FEATURE:
<221> NAME/KEY: misc_feature
<222> LOCATION: (1)...(1459)
<223> OTHER INFORMATION: n = A,T,C or G

<400> SEQUENCE: 174

| | | | | | |
|---|---|---|---|---|---|
| ggtcagccgc | acactgtttc | cagaagtgag | tgcagagctc | ctacaccatc | gggctgggcc | 60 |
| tgcacagtct | tgaggccgac | caagagccag | ggagccagat | ggtggaggcc | agcctctccg | 120 |
| tacggcaccc | agagtacaac | agacccttgc | tcgctaacga | cctcatgctc | atcaagttgg | 180 |
| acgaatccgt | gtccgagtct | gacaccatcc | ggagcatcag | cattgcttcg | cagtgcccta | 240 |
| ccgcggggaa | ctcttgcctc | gtttctggct | ggggtctgct | ggcgaacggt | gagctcacgg | 300 |

-continued

```
gtgtgtgtct gccctcttca aggaggtcct ctgcccagtc gcgggggctg acccagagct      360
ctgcgtccca ggcagaatgc ctaccgtgct gcagtgcgtg aacgtgtcgg tggtgtctga      420
ngaggtctgc antaagctct atgacccgct gtaccacccc ancatgttct gcgccggcgg      480
agggcaagac cagaaggact cctgcaacgt gagagagggg aaaggggagg gcaggcgact      540
cagggaaggg tggagaaggg ggagacagag acacacaggg ccgcatggcg agatgcagag      600
atggagagac acacagggag acagtgacaa ctagagagag aaactgagag aaacagagaa      660
ataaacacag gaataaagag aagcaaagga agagagaaac agaaacagac atggggaggc      720
agaaacacac acacatagaa atgcagttga ccttccaaca gcatggggcc tgagggcggt      780
gacctccacc caatagaaaa tcctcttata acttttgact ccccaaaaac ctgactagaa      840
atagcctact gttgacgggg agccttacca ataacataaa tagtcgattt atgcatacgt      900
tttatgcatt catgatatac ctttgttgga attttttgat atttctaagc tacacagttc      960
gtctgtgaat ttttttaaat tgttgcaact ctcctaaaat ttttctgatg tgtttattga     1020
aaaaatccaa gtataagtgg acttgtgcat tcaaaccagg gttgttcaag ggtcaactgt     1080
gtacccagag ggaaacagtg acacagattc atagaggtga aacacgaaga gaaacaggaa     1140
aaatcaagac tctacaaaga ggctgggcag ggtggctcat gcctgtaatc ccagcacttt     1200
gggaggcgag gcaggcagat cacttgaggt aaggagttca agaccagcct ggccaaaatg     1260
gtgaaatcct gtctgtacta aaaatacaaa agttagctgg atatggtggc aggcgcctgt     1320
aatcccagct acttgggagg ctgaggcagg agaattgctt gaatatggga ggcagaggtt     1380
gaagtgagtt gagatcacac cactatactc cagctggggc aacagagtaa gactctgtct     1440
caaaaaaaaa aaaaaaaaa                                                  1459
```

<210> SEQ ID NO 175
<211> LENGTH: 1167
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175

```
gcgcagccct ggcaggcggc actggtcatg gaaaacgaat tgttctgctc gggcgtcctg       60
gtgcatccgc agtgggtgct gtcagccgca cactgtttcc agaactccta caccatcggg      120
ctgggcctgc acagtcttga ggccgaccaa gagccaggga gccagatggt ggaggccagc      180
ctctccgtac ggcacccaga gtacaacaga ctcttgctcg ctaacgacct catgctcatc      240
aagttggacg aatccgtgtc cgagtctgac accatccgga gcatcagcat tgcttcgcag      300
tgccctaccg cggggaactc ttgcctcgtn tctggctggg gtctgctggc gaacggcaga      360
atgcctaccg tgctgcactg cgtgaacgtg tcggtggtgt ctgaggangt ctgcagtaag      420
ctctatgacc cgctgtacca ccccagcatg ttctgcgccg cgcgagggca agaccagaag      480
gactcctgca acggtgactc tggggggccc ctgatctgca acgggtactt gcagggcctt      540
gtgtctttcg gaaaagcccc gtgtggccaa cttggcgtgc caggtgtcta caccaacctc      600
tgcaaattca ctgagtggat agagaaaacc gtccagncca gttaactctg gggactggga      660
acccatgaaa ttgaccccca aatacatcct gcggaangaa ttcaggaata tctgttccca      720
gcccctcctc cctcaggccc aggagtccag gccccagccc cctcctccct caaaccaagg      780
gtacagatcc ccagcccctc ctccctcaga cccaggagtc cagaccccccc agcccctcnt      840
```

```
ccntcagacc caggagtcca gcccctcctc cntcagacgc aggagtccag accccccagc    900
ccntcntccg tcagacccag gggtgcaggc ccccaacccc tcntcctca gagtcagagg    960 tccaagcccc caaccctcg ttccccagac ccagaggtnc aggtcccagc ccctcctccc   1020
tcagacccag cggtccaatg ccacctagan tntccctgta cacagtgccc ccttgtggca   1080
ngttgaccca accttaccag ttggttttc attttttgtc cctttcccct agatccagaa   1140
ataaagtnta agagaagcgc aaaaaaa                                      1167
```

<210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
         35                  40                  45

Glu Ala Ser Leu Ser Val Arg His Pro Glu Tyr Asn Arg Leu Leu Leu
 50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
           100                 105                 110

Pro Thr Val Leu His Cys Val Asn Val Ser Val Val Ser Glu Xaa Val
       115                 120                 125

Cys Ser Lys Leu Tyr Asp Pro Leu Tyr His Pro Ser Met Phe Cys Ala
130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175

Ala Pro Cys Gly Gln Leu Gly Val Pro Gly Val Tyr Thr Asn Leu Cys
            180                 185                 190

Lys Phe Thr Glu Trp Ile Glu Lys Thr Val Gln Xaa Ser
        195                 200                 205
```

<210> SEQ ID NO 177
<211> LENGTH: 1119
<212> TYPE: DNA
<213> ORGANISM: Homo sapien

<400> SEQUENCE: 177

```
gcgcactcgc agccctggca ggcggcactg gtcatggaaa acgaattgtt ctgctcgggc     60
gtcctggtgc atccgcagtg ggtgctgtca gccgcacact gtttccagaa ctcctacacc    120
atcgggctgg gcctgcacag tcttgaggcc gaccaagagc cagggagcca gatggtggag    180
gccagcctct ccgtacggca cccagagtac aacagaccct tgctcgctaa cgacctcatg    240
```

```
ctcatcaagt tggacgaatc cgtgtccgag tctgacacca tccggagcat cagcattgct      300
tcgcagtgcc ctaccgcggg gaactcttgc ctcgtttctg gctggggtct gctggcgaac      360
gatgctgtga ttgccatcca gtcccagact gtgggaggct gggagtgtga gaagctttcc      420
caaccctggc agggttgtac catttcggca acttccagtg caaggacgtc ctgctgcatc      480
ctcactgggt gctcactact gctcactgca tcacccggaa cactgtgatc aactagccag      540
caccatagtt ctccgaagtc agactatcat gattactgtg ttgactgtgc tgtctattgt      600
actaaccatg ccgatgttta ggtgaaatta gcgtcacttg gcctcaacca tcttggtatc      660
cagttatcct cactgaattg agatttcctg cttcagtgtc agccattccc acataatttc      720
tgacctacag aggtgaggga tcatatagct cttcaaggat gctggtactc ccctcacaaa      780
ttcatttctc ctgttgtagt gaaggtgcg ccctctggag cctcccaggg tgggtgtgca       840
ggtcacaatg atgaatgtat gatcgtgttc ccattaccca aagcctttaa atccctcatg      900
ctcagtacac caggcaggt ctagcatttc ttcatttagt gtatgctgtc cattcatgca       960
accacctcag gactcctgga ttctctgcct agttgagctc ctgcatgctg cctccttggg     1020
gaggtgaggg agagggccca tggttcaatg ggatctgtgc agttgtaaca cattaggtgc     1080
ttaataaaca gaagctgtga tgttaaaaaa aaaaaaaaa                            1119

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178

Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
             20                  25                  30

Gly Leu His Ser Leu Glu Ala Asp Gln Glu Pro Gly Ser Gln Met Val
         35                  40                  45

Glu Ala Ser Leu Ser Val Arg His Pro Glu Tyr Asn Arg Pro Leu Leu
     50                  55                  60

Ala Asn Asp Leu Met Leu Ile Lys Leu Asp Glu Ser Val Ser Glu Ser
 65                  70                  75                  80

Asp Thr Ile Arg Ser Ile Ser Ile Ala Ser Gln Cys Pro Thr Ala Gly
                 85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
        115                 120                 125

Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Leu Thr Ala Ser
145                 150                 155                 160

Pro Gly Thr Leu

<210> SEQ ID NO 179
<211> LENGTH: 250
<212> TYPE: DNA
```

```
<213> ORGANISM: Homo sapien

<400> SEQUENCE: 179
ctggagtgcc ttggtgtttc aagcccctgc aggaagcaga atgcaccttc tgaggcacct      60
ccagctgccc ccggccgggg gatgcgaggc tcggagcacc cttgccggc tgtgattgct      120 gccaggcact gttcatctca gcttttctgt cccttgctc ccggcaagcg cttctgctga      180
aagttcatat ctggagcctg atgtcttaac gaataaaggt cccatgctcc acccgaaaaa      240
aaaaaaaaaa                                                              250

<210> SEQ ID NO 180
<211> LENGTH: 202
<212> TYPE: DNA
<213> ORGANISM: Homo sapien

<400> SEQUENCE: 180
actagtccag tgtggtggaa ttccattgtg ttgggcccaa cacaatggct acctttaaca      60
tcacccagac cccgcccctg cccgtgcccc acgctgctgc taacgacagt atgatgctta      120
ctctgctact cggaaactat tttatgtaa ttaatgtatg ctttcttgtt tataaatgcc      180
tgatttaaaa aaaaaaaaaa aa                                                 202

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181
tccytttgkt naggtttkkg agacamcccck agacctwaan ctgtgtcaca gacttcyngg      60
aatgtttagg cagtgctagt aatttcytcg taatgattct gttattactt tcctnattct      120
ttattcctct ttcttctgaa gattaatgaa gttgaaaatt gaggtggata aatacaaaaa      180
ggtagtgtga tagtataagt atctaagtgc agatgaaagt gtgttatata tatccattca      240
aaattatgca agttagtaat tactcagggt taactaaatt actttaatat gctgttgaac      300
ctactctgtt ccttggctag aaaaaattat aaacaggact ttgttagttt gggaagccaa      360
attgataata ttctatgttc taaaagttgg gctatacata aattattaag aaatatggaw      420
ttttattccc aggaatatgg kgttcatttt atgaatatta cscrggatag awgtwtgagt      480
aaaaycagtt ttggtwaata ygtwaatatg tcmtaaataa acaakgcttt gacttatttc      540
caaaaaaaaa aaaaaaaa                                                      558

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182
acagggwttk grggatgcta agsccccrga rwtygtttga tccaaccctg gcttwttttc      60
agaggggaaa atgggggccta gaagttacag mscatytagy tggtgcgmtg gcaccctgg      120 cstcacacag astcccgagt agctgggact acaggcacac agtcactgaa gcaggccctg      180
```

```
ttwgcaattc acgttgccac ctccaactta aacattcttc atatgtgatg tccttagtca      240
ctaaggttaa actttcccac ccagaaaagg caacttagat aaaatcttag agtactttca      300
tactmttcta agtcctcttc cagcctcact kkgagtcctm cytgggggtt gataggaant      360
ntctcttggc tttctcaata aartctctat ycatctcatg tttaatttgg tacgcatara      420
awtgstgara aaattaaaat gttctggtty mactttaaaa araaaaaaaa aaaaaaaa        479
```

<210> SEQ ID NO 183
<211> LENGTH: 384
<212> TYPE: DNA
<213> ORGANISM: Homo sapien

<400> SEQUENCE: 183

```
aggcgggagc agaagctaaa gccaaagccc aagaagagtg gcagtgccag cactggtgcc       60
agtaccagta ccaataacag tgccagtgcc agtgccagca ccagtggtgg cttcagtgct      120
ggtgccagcc tgaccgccac tctcacattt gggctcttcg ctggccttgg tggagctggt      180
gccagcacca gtggcagctc tggtgcctgt ggtttctcct acaagtgaga ttttagatat      240
tgttaatcct gccagtcttt ctcttcaagc cagggtgcat cctcagaaac ctactcaaca      300
cagcactcta ggcagccact atcaatcaat tgaagttgac actctgcatt aratctattt      360
gccatttcaa aaaaaaaaaa aaaa                                             384
```

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184

```
accgaattgg gaccgctggc ttataagcga tcatgtyynt ccrgtatkac ctcaacgagc       60
agggagatcg agtctatacg ctgaagaaat ttgacccgat gggacaacag acctgctcag      120
cccatcctgc tcggttctcc ccagatgaca aatactctsg acaccgaatc accatcaaga      180
aacgcttcaa ggtgctcatg acccagcaac cgcgccctgt cctctgaggg tcccttaaac      240
tgatgtcttt tctgccacct gttacccctc ggagactccg taaccaaact cttcggactg      300
tgagccctga tgcctttttg ccagcctac tctttggcat ccagtctctc gtggcgattg       360
attatgcttg tgtgaggcaa tcatggtggc atcacccata aagggaacac atttgacttt      420
tttttctcat attttaaatt actacmagaw tattwmagaw waaatgawtt gaaaaactst      480
taaaaaaaaa aaaaaa                                                      496
```

<210> SEQ ID NO 185
<211> LENGTH: 384
<212> TYPE: DNA
<213> ORGANISM: Homo sapien

<400> SEQUENCE: 185

```
gctggtagcc tatggcgkgg cccacggagg ggctcctgag gccacggrac agtgacttcc       60
caagtatcyt gcgcsgcgtc ttctaccgtc cctacctgca gatcttcggg cagattcccc      120
aggaggacat ggacgtggcc ctcatggagc acagcaactg ytcgtcggag cccggcttct      180
gggcacaccc tcctggggcc caggcgggca cctgcgtctc ccagtatgcc aactggctgg      240
```

| | |
|---|---|
| tggtgctgct cctcgtcatc ttcctgctcg tggccaacat cctgctggtc aacttgctca | 300 |
| ttgccatgtt cagttacaca ttcggcaaag tacagggcaa cagcgatctc tactgggaag | 360 |
| gcgcagcgtt accgcctcat ccgg | 384 |

<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

| | |
|---|---|
| gagttagctc ctccacaacc ttgatgaggt cgtctgcagt ggcctctcgc ttcataccgc | 60 |
| tnccatcgtc atactgtagg tttgccacca cytcctggca tcttggggcg gcntaatatt | 120 |
| ccaggaaact ctcaatcaag tcaccgtcga tgaaacctgt gggctggttc tgtcttccgc | 180 |
| tcggtgtgaa aggatctccc agaaggagtg ctcgatcttc cccacactttt tgatgactttt | 240 |
| attgagtcga ttctgcatgt ccagcaggag gttgtaccag ctctctgaca gtgaggtcac | 300 |
| cagccctatc atgccgttga mcgtgccgaa garcaccgag ccttgtgtgg gggkkgaagt | 360 |
| ctcacccaga ttctgcatta ccagagagcc gtggcaaaag acattgacaa actcgcccag | 420 |
| gtggaaaaag amcamctcct ggargtgctn gccgctcctc gtcmgttggt ggcagcgctw | 480 |
| tccttttgac acacaaacaa gttaaaggca ttttcagccc ccagaaattt gtcatcatcc | 540 |
| aagatntcgc acagcactna tccagttggg attaaat | 577 |

<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

| | |
|---|---|
| aacatcttcc tgtataatgc tgtgtaatat cgatccgatn ttgtctgstg agaatycatw | 60 |
| actkggaaaa gmaacattaa agcctggaca ctggtattaa aattcacaat atgcaacact | 120 |
| ttaaacagtg tgtcaatctg ctcccyynac tttgtcatca ccagtctggg aakaagggta | 180 |
| tgccctattc acacctgtta aaagggcgct aagcattttt gattcaacat cttttttttt | 240 |
| gacacaagtc cgaaaaaagc aaaagtaaac agttatyaat ttgttagcca attcactttc | 300 |
| ttcatgggac agagccatyt gatttaaaaa gcaaattgca taatattgag cttygggagc | 360 |
| tgatatttga gcggaagagt agcctttcta cttcaccaga cacaactccc tttcatattg | 420 |
| ggatgttnac naaagtwatg tctctwacag atgggatgct tttgtggcaa ttctgttctg | 480 |
| aggatctccc agtttattta ccacttgcac aagaaggcgt tttcttcctc aggc | 534 |

<210> SEQ ID NO 188
<211> LENGTH: 761
<212> TYPE: DNA
<213> ORGANISM: Homo sapien
<220> FEATURE:
<221> NAME/KEY: misc_feature
<222> LOCATION: (1)...(761)
<223> OTHER INFORMATION: n = A,T,C or G

<400> SEQUENCE: 188

```
agaaaccagt atctctnaaa acaacctctc ataccttgtg gacctaattt tgtgtgcgtg    60
tgtgtgtgcg cgcatattat atagacaggc acatcttttt tacttttgta aaagcttatg   120
cctctttggt atctatatct gtgaaagttt taatgatctg ccataatgtc ttggggacct   180
ttgtcttctg tgtaaatggt actagagaaa acacctatnt tatgagtcaa tctagtttngt   240 tttattcgac atgaaggaaa tttccagatn acaacactna caaactctcc ctkgackarg   300
ggggacaaag aaaagcaaaa ctgamcataa raaacaatwa cctggtgaga arttgcataa   360
acagaaatwr ggtagtatat tgaarnacag catcattaaa rmgttwtktt wttctcccctt   420 gcaaaaaaca tgtacngact tcccgttgag taatgccaag ttgttttttt tatnataaaa   480 cttgccttc attacatgtt tnaaagtggt gtggtgggcc aaaatattga aatgatggaa   540
ctgactgata aagctgtaca aataagcagt gtgcctaaca agcaacacag taatgttgac   600
atgcttaatt cacaaatgct aatttcatta taaatgtttg ctaaaataca ctttgaacta   660
tttttctgtn ttcccagagc tgagatntta gattttatgt agtataagt gaaaaantac    720 gaaaataata acattgaaga aaaananaaa aaanaaaaaa a                       761

<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189
tttttttttt tttgccgatn ctactatttt attgcaggan gtggggtgt atgcaccgca     60 caccggggct atnagaagca agaaggaagg agggagggca cagccccttg ctgagcaaca   120
aagccgcctg ctgccttctc tgtctgtctc ctggtgcagg cacatgggga gaccttcccc   180
aaggcagggg ccaccagtcc aggggtggga atacaggggg tgggangtgt gcataagaag   240
tgataggcac aggccacccg gtacagaccc ctcggctcct gacaggtnga tttcgaccag   300
gtcattgtgc cctgcccagg cacagcgtan atctggaaaa gacagaatgc tttccttttc   360
aaatttggct ngtcatngaa ngggcanttt tccaanttng gctnggtctt ggtacncttg   420
gttcggccca gctccncgtc caaaaantat tcacccnnct ccnaattgct tgcnggnccc   480
cc                                                                 482

<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190
tttttttttt ttttaaaaca gttttcaca acaaaattta ttagaagaat agtggttttg     60
aaaactctcg catccagtga gaactaccat acaccacatt acagctngga atgtnctcca   120
aatgtctggt caaatgatac aatggaacca ttcaatctta cacatgcacg aaagaacaag   180
cgcttttgac atacaatgca caaaaaaaaa aggggggggg gaccacatgg attaaaattt   240
taagtactca tcacatacat taagacacag ttctagtcca gtcnaaaatc agaactgcnt   300
```

| | |
|---|---|
| tgaaaaattt catgtatgca atccaaccaa agaacttnat tggtgatcat gantnctcta | 360 |
| ctacatcnac cttgatcatt gccaggaacn aaaagttnaa ancacncngt acaaaaanaa | 420 |
| tctgtaattn anttcaacct ccgtacngaa aaatnttnnt tatacactcc c | 471 |

<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191

| | |
|---|---|
| gagggattga aggtctgttc tastgtcggm ctgttcagcc accaactcta acaagttgct | 60 |
| gtcttccact cactgtctgt aagcttttta acccagacwg tatcttcata aatagaacaa | 120 |
| attcttcacc agtcacatct tctaggacct ttttggattc agttagtata agctcttcca | 180 |
| cttcctttgt taagacttca tctggtaaag tcttaagttt tgtagaaagg aattyaattg | 240 |
| ctcgttctct aacaatgtcc tctccttgaa gtatttggct gaacaaccca cctaaagtcc | 300 |
| ctttgtgcat ccattttaaa tatacttaat agggcattgk tncactaggt taaattctgc | 360 |
| aagagtcatc tgtctgcaaa agttgcgtta gtatatctgc ca | 402 |

<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192

| | |
|---|---|
| gagctcggat ccaataatct ttgtctgagg gcagcacaca tatncagtgc catggnaact | 60 |
| ggtctacccc acatgggagc agcatgccgt agntatataa ggtcattccc tgagtcagac | 120 |
| atgcytyttt gaytaccgtg tgccaagtgc tggtgattct yaacacacyt ccatcccgyt | 180 |
| cttttgtgga aaaactggca cttktctgga actagcarga catcacttac aaattcaccc | 240 |
| acgagacact tgaaggtgt aacaaagcga ytcttgcatt gctttttgtc cctccggcac | 300 |
| cagttgtcaa tactaacccg ctggtttgcc tccatcacat ttgtgatctg tagctctgga | 360 |
| tacatctcct gacagtactg aagaacttct tcttttgttt caaaagcarc tcttggtgcc | 420 |
| tgttggatca ggttcccatt tcccagtcyg aatgttcaca tggcatattt wacttcccac | 480 |
| aaaacattgc gatttgaggc tcagcaacag caaatcctgt tccggcattg gctgcaagag | 540 |
| cctcgatgta gccggccagc gccaaggcag gcgccgtgag ccccaccagc agcagaagca | 600 |
| g | 601 |

<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
<223> OTHER INFORMATION: n = A,T,C or G

<400> SEQUENCE: 193

| | |
|---|---|
| atacagccca natcccacca cgaagatgcg cttgttgact gagaacctga tgcggtcact | 60 |

```
ggtcccgctg tagccccagc gactctccac ctgctggaag cggttgatgc tgcactcytt      120
cccaacgcag gcagmagcgg gsccggtcaa tgaactccay tcgtggcttg gggtkgacgg      180
tkaagtgcag gaagaggctg accacctcgc ggtccaccag gatgcccgac tgtgcgggac      240
ctgcagcgaa actcctcgat ggtcatgagc gggaagcgaa tgaggcccag ggccttgccc      300
agaaccttcc gcctgttctc tggcgtcacc tgcagctgct gccgctgaca ctcggcctcg      360
gaccagcgga caaacggcrt tgaacagccg cacctcacgg atgcccagtg tgtcgcgctc      420
caggammgsc accagcgtgt ccaggtcaat gtcggtgaag ccctccgcgg gtratggcgt      480
ctgcagtgtt tttgtcgatg ttctccaggc acaggctggc cagctgcggt tcatcgaaga      540
gtcgcgcctg cgtgagcagc atgaaggcgt tgtcggctcg cagttcttct tcaggaactc      600
cacgcaat                                                              608

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194
gaacggctgg accttgcctc gcattgtgct tgctggcagg gaataccttg gcaagcagyt       60
ccagtccgag cagccccaga ccgctgccgc ccgaagctaa gcctgcctct ggccttcccc      120
tccgcctcaa tgcagaacca gtagtgggag cactgtgttt agagttaaga gtgaacactg      180
tttgatttta cttgggaatt tcctctgtta tatagctttt cccaatgcta atttccaaac      240
aacaacaaca aaataacatg tttgcctgtt aagttgtata aaagtaggtg attctgtatt      300
taaagaaaat attactgtta catatactgc ttgcaatttc tgtatttatt gktnctstgg      360
aaataaatat agttattaaa ggttgtcant cc                                   392

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 195
ccsttkgagg ggtkaggkyc cagttyccga gtggaagaaa caggccagga gaagtgcgtg       60
ccgagctgag gcagatgttc ccacagtgac ccccagagcc stgggstata gtytctgacc      120
cctcncaagg aaagaccacs ttctggggac atgggctgga gggcaggacc tagaggcacc      180
aagggaaggc cccattccgg ggstgttccc cgaggaggaa gggaaggggc tctgtgtgcc      240
ccccasgagg aagaggccct gagtcctggg atcagacacc ccttcacgtg tatccccaca      300
caaatgcaag ctcaccaagg tcccctctca gtcccttcc stacaccctg amcggccact      360
gscscacacc cacccagagc acgccacccg ccatggggar tgtgctcaag gartcgcngg      420
gcarcgtgga catctngtcc cagaaggggg cagaatctcc aatagangga ctgarcmstt      480
gctnanaaaa aaaaanaaaa aa                                              502

<210> SEQ ID NO 196
```

```
<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G

<400> SEQUENCE: 196
ggttacttgg tttcattgcc accacttagt ggatgtcatt tagaaccatt ttgtctgctc      60
cctctggaag ccttgcgcag agcggacttt gtaattgttg gagaataact gctgaatttt    120 wagctgttk gagttgatts gcaccactgc acccacaact tcaatatgaa aacyawttga     180
actwatttat tatcttgtga aaagtataac aatgaaaatt ttgttcatac tgtattkatc    240
aagtatgatg aaaagcaawa gatatatatt cttttattat gttaaattat gattgccatt    300
attaatcggc aaaatgtgga gtgtatgttc ttttcacagt aatatatgcc ttttgtaact    360
tcacttggtt attttattgt aaatgartta caaaattctt aatttaagar aatggtatgt    420
watatttatt tcattaattt ctttcctkgt ttacgtwaat tttgaaaaga wtgcatgatt    480
tcttgacaga aatcgatctt gatgctgtgg aagtagtttg acccacatcc ctatgagttt    540
ttcttagaat gtataaaggt tgtagcccat cnaacttcaa agaaaaaaat gaccacatac    600
tttgcaatca ggctgaaatg tggcatgctn ttctaattcc aactttataa actagcaaan    660
aagtg                                                                665

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197
ttttnttttt ttttttttgc aggaaggatt ccatttattg tggatgcatt ttcacaatat     60
atgtttattg gagcgatcca ttatcagtga aaagtatcaa gtgtttataa nattttagg    120 aaggcagatt cacagaacat gctngtcngc ttgcagtttt acctcgtana gatnacagag    180
aattatagtc naaccagtaa acnaggaatt tacttttcaa aagattaaat ccaaactgaa    240
caaaattcta ccctgaaact tactccatcc aaatattgga ataanagtca gcagtgatac    300
attctcttct gaactttaga ttttctagaa aaatatgtaa tagtgatcag gaagagctct    360
tgttcaaaag tacaacnaag caatgttccc ttaccatagg ccttaattca aactttgatc    420
catttcactc ccatcacggg agtcaatgct acctgggaca cttgtatttt gttcatnctg    480
ancntggctt aa                                                        492

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

<400> SEQUENCE: 198 tttntttgn atttcantct gtannaanta ttttcattat gtttattana aaaatatnaa      60
tgtntccacn acaaatcatn ttacntnagt aagaggccan ctacattgta caacatacac    120
```

```
tgagtatatt ttgaaaagga caagtttaaa gtanacncat attgccganc atancacatt    180
tatacatggc ttgattgata tttagcacag canaaactga gtgagttacc agaaanaaat    240
natatatgtc aatcngattt aagatacaaa acagatccta tggtacatan catcntgtag    300
gagttgtggc tttatgttta ctgaaagtca atgcagttcc tgtacaaaga gatggccgta    360
agcattctag tacctctact ccatggttaa gaatcgtaca cttatgttta catatgtnca    420
gggtaagaat tgtgttaagt naanttatgg agaggtccan gagaaaaatt tgatncaa     478
```

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199

```
agtgacttgt cctccaacaa aaccccttga tcaagtttgt ggcactgaca atcagaccta    60
tgctagttcc tgtcatctat tcgctactaa atgcagactg gaggggacca aaaaggggca   120
tcaactccag ctggattatt ttggagcctg caaatctatt cctacttgta cggactttga   180
agtgattcag tttcctctac ggatgagaga ctggctcaag aatatcctca tgcagcttta   240
tgaagccnac tctgaacacg ctggttatct nagatgagaa ncagaaaat aaagtcnaga    300 aaatttacct ggangaaaag aggctttngg ctggggacca tcccattgaa ccttctctta   360 anggactttta agaanaaact accacatgtn tgtngtatcc tggtgccngg ccgtttantg   420
aacntngacn ncacccttnt ggaatanant cttgacngcn tcctgaactt gctcctctgc   480
ga                                                                  482
```

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200

```
cggccgcaag tgcaactcca gctggggccg tgcggacgaa gattctgcca gcagttggtc    60
cgactgcgac gacggcggcg gcgacagtcg caggtgcagc gcgggcgcct gggtcttgc    120 aaggctgagc tgacgccgca gaggtcgtgt cacgtcccac gaccttgacg ccgtcgggga   180
cagccggaac agagcccggt gaangcggga ggcctcgggg agcccctcgg gaagggcggc   240
ccgagagata cgcaggtgca ggtggccgcc                                    270
```

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 201

```
tttttttttt ttttggaatc tactgcgagc acagcaggtc agcaacaagt ttattttgca    60
```

| | | | | |
|---|---|---|---|---|
| gctagcaagg | taacagggta | gggcatggtt | acatgttcag | gtcaacttcc tttgtcgtgg | 120 |
| ttgattggtt | tgtctttatg | ggggcggggt | ggggtagggg | aaancgaagc anaantaaca | 180 |
| tggagtgggg | gcaccctccc | tgtagaacct | ggttacnaaa | gcttgggggca gttcacctgg | 240 |
| tctgtgaccg | tcattttctt | gacatcaatg | ttattagaag | tcaggatatc ttttagagag | 300 |
| tccactgtnt | ctggagggag | attagggttt | cttgccaana | tccaancaaa atccacntga | 360 |
| aaaagttgga | tgatncangt | acngaatacc | ganggcatan | ttctcatant cggtggcca | 419 |

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202

| | | | | |
|---|---|---|---|---|
| tttntttttt | tttttttttt | tttttttttt | tttttttttt | tttttttttt tttttttttt | 60 |
| tggcacttaa | tccatttta | tttcaaaatg | tctacaaant | ttnaatncnc cattatacng | 120 |
| gtnattttnc | aaaatctaaa | nnttattcaa | atntnagcca | aatccttac ncaaatnnaa | 180 |
| tacncncaaa | aatcaaaaat | atacntntct | ttcagcaaac | ttngttacat aaattaaaaa | 240 |
| aatatatacg | gctggtgttt | tcaaagtaca | attatcttaa | cactgcaaac atntttnnaa | 300 |
| ggaactaaaa | taaaaaaaaa | cactnccgca | aaggttaaag | ggaacaacaa attcntttta | 360 |
| caacancnnc | nattataaaa | atcatatctc | aaatcttagg | ggaatatata cttcacacng | 420 |
| ggatcttaac | ttttactnca | ctttgtttat | tttttttanaa | ccattgtntt gggcccaaca | 480 |
| caatggnaat | nccnccncnc | tggactagt | | | 509 |

<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203

| | | | | |
|---|---|---|---|---|
| tttttttttt | ttttttttga | cccccctctt | ataaaaaaca | agttaccatt ttatttact | 60 |
| tacacatatt | tattttataa | ttggtattag | atattcaaaa | ggcagctttt aaaatcaaac | 120 |
| taaatggaaa | ctgccttaga | tacataattc | ttaggaatta | gcttaaaatc tgcctaaagt | 180 |
| gaaaatcttc | tctagctctt | ttgactgtaa | attttgact | cttgtaaaac atccaaattc | 240 |
| attttcttg | tctttaaaat | tatctaatct | ttccattttt | tccctattcc aagtcaattt | 300 |
| gcttctctag | cctcatttcc | tagctcttat | ctactattag | taagtggctt ttttcctaaa | 360 |
| agggaaaaca | ggaagagana | atggcacaca | aaacaaacat | tttatattca tatttctacc | 420 |
| tacgttaata | aaatagcatt | ttgtgaagcc | agctcaaaag | aaggcttaga tccttttatg | 480 |
| tccattttag | tcactaaacg | atatcnaaag | tgccagaatg | caaaaggttt gtgaacattt | 540 |
| attcaaaagc | taatataaga | tatttcacat | actcatcttt | ctg | 583 |

<210> SEQ ID NO 204
<211> LENGTH: 589
<212> TYPE: DNA
<213> ORGANISM: Homo sapien

```
<220> FEATURE:
<221> NAME/KEY: misc_feature
<222> LOCATION: (1)...(589)
<223> OTHER INFORMATION: n = A,T,C or G

<400> SEQUENCE: 204 tttttttnt  tttttttttt  tttttnctc   ttctttttt   ttganaatga ggatcgagtt    60
tttcactctc tagatagggc  atgaagaaaa  ctcatctttc  cagctttaaa ataacaatca   120
aatctcttat gctatatcat  attttaagtt  aaactaatga  gtcactggct tatcttctcc   180
tgaaggaaat ctgttcattc  ttctcattca  tatagttata  tcaagtacta ccttgcatat   240
tgagaggttt ttcttctcta  tttacacata  tatttccatg  tgaatttgta tcaaacctt    300 attttcatgc aaactagaaa  ataatgtntt  cttttgcata  agagaagaga acaatatnag   360
cattacaaaa ctgctcaaat  tgtttgttaa  gnttatccat  tataattagt tnggcaggag   420
ctaatacaaa tcacatttac  ngacnagcaa  taataaaact  gaagtaccag ttaaatatcc   480
aaaataatta aaggaacatt  tttagcctgg  gtataattag  ctaattcact ttacaagcat   540
ttattnagaa tgaattcaca  tgttattatt  ccntagccca  acacaatgg                589

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205 tttttnttt  tttttcagt  aataatcaga  acaatattta  ttttatatt  taaaattcat    60 agaaaagtgc cttacattta  ataaaagttt  gtttctcaaa  gtgatcagag gaattagata   120
tngtcttgaa caccaatatt  aatttgagga  aaatacacca  aaatacatta agtaaattat   180
ttaagatcat agagcttgta  agtgaaaaga  taaaatttga  cctcagaaac tctgagcatt   240
aaaaatccac tattagcaaa  taaattacta  tggacttctt  gctttaattt tgtgatgaat   300
atggggtgtc actggtaaac  caacacattc  tgaaggatac  attacttagt gatagattct   360
tatgtacttt gctanatnac  gtggatatga  gttgacaagt  ttctctttct tcaatctttt   420
aaggggcnga ngaaatgagg  aagaaaagaa  aaggattacg  catactgttc tttctatngg   480
aaggattaga tatgtttcct  ttgccaatat  taaaaaaata  ataatgttta ctactagtga   540
aaccc                                                                  545

<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206
tttttttttt  tttttagtc  aagtttctna  tttttattat  aattaaagtc ttggtcattt    60
catttattag ctctgcaact  tacatattta  aattaaagaa  acgttnttag acaactgtna   120
caatttataa atgtaaggtg  ccattattga  gtanatatat  tcctccaaga gtggatgtgt   180
cccttctccc accaactaat  gaancagcaa  cattagttta  atttttattag tagatnatac   240
```

```
actgctgcaa acgctaattc tcttctccat ccccatgtng atattgtgta tatgtgtgag    300
ttggtnagaa tgcatcanca atctnacaat caacagcaag atgaagctag gcntgggctt    360
tcggtgaaaa tagactgtgt ctgtctgaat caaatgatct gacctatcct cggtggcaag    420
aactcttcga accgcttcct caaaggcngc tgccacattt gtggcntctn ttgcacttgt    480
ttcaaaa                                                              487
```

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207

```
tgaattggct aaaagactgc atttttanaa ctagcaactc ttatttcttt cctttaaaaa    60
tacatagcat taaatcccaa atcctattta aagacctgac agcttgagaa ggtcactact    120
gcatttatag gaccttctgg tggttctgct gttacntttg aantctgaca atccttgana    180
atctttgcat gcagaggagg taaaaggtat tggattttca cagaggaana acacagcgca    240
gaaatgaagg ggccaggctt actgagcttg tccactggag ggctcatggg tgggacatgg    300
aaaagaaggc agcctaggcc ctggggagcc ca                                  332
```

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 208

```
agggcgtggt gcggagggcg ttactgtttt gtctcagtaa caataaatac aaaaagactg    60
gttgtgttcc ggccccatcc aaccacgaag ttgatttctc ttgtgtgcag agtgactgat    120
tttaaaggac atggagcttg tcacaatgtc acaatgtcac agtgtgaagg gcacactcac    180
tcccgcgtga ttcacattta gcaaccaaca atagctcatg agtccatact tgtaaatact    240
tttggcagaa tacttnttga aacttgcaga tgataactaa gatccaagat atttcccaaa    300
gtaaatagaa gtgggtcata atattaatta cctgttcaca tcagcttcca tttacaagtc    360
atgagcccag acactgacat caaactaagc ccacttagac tcctcaccac cagtctgtcc    420
tgtcatcaga caggaggctg tcaccttgac caaattctca ccagtcaatc atctatccaa    480
aaaccattac ctgatccact tccggtaatg caccaccttg gtga                    524
```

<210> SEQ ID NO 209
<211> LENGTH: 159
<212> TYPE: DNA
<213> ORGANISM: Homo sapien

<400> SEQUENCE: 209

```
gggtgaggaa atccagagtt gccatggaga aaattccagt gtcagcattc ttgctccttg    60
tggccctctc ctacactctg gccagagata ccacagtcaa acctggagcc aaaaaggaca    120
caaaggactc tcgacccaaa ctgccccaga ccctctcca                           159
```

```
<210> SEQ ID NO 210
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 210
actccctggc agacaaaggc agaggagaga gctctgttag ttctgtgttg ttgaactgcc        60
actgaatttc tttccacttg gactattaca tgccanttga gggactaatg gaaaaacgta       120
tggggagatt ttanccaatt tangtntgta aatggggaga ctggggcagg cgggagagat       180
ttgcagggtg naaatgggan ggctggtttg ttanatgaac agggacatag gaggtaggca       240
ccaggatgct aaatca                                                      256

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211
acattgtttt tttgagataa agcattgaga gagctctcct taacgtgaca caatggaagg        60
actggaacac atacccacat ctttgttctg agggataatt ttctgataaa gtcttgctgt       120
atattcaagc acatatgtta tatattattc agttccatgt ttatagccta gttaaggaga       180
ggggagatac attcngaaag aggactgaaa gaaatactca agtnggaaaa cagaaaaaga       240 aaaaaggag caaatgagaa gcct                                              264

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212
acccaaaaat ccaatgctga atatttggct tcattattcc canattcttt gattgtcaaa        60
ggatttaatg ttgtctcagc ttgggcactt cagttaggac ctaaggatgc cagccggcag       120
gtttatatat gcagcaacaa tattcaagcg cgacaacagg ttattgaact tgcccgccag       180
ttnaatttca ttcccattga cttgggatcc ttatcatcag ccagagagat tgaaaattta       240
cccctacnac tctttactct ctgganaggg ccagtggtgg tagctataag cttggccaca       300 ttttttttc ctttattcct ttgtcaga                                          328

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213
```

```
acttatgagc agagcgacat atccnagtgt agactgaata aaactgaatt ctctccagtt        60
taaagcattg ctcactgaag ggatagaagt gactgccagg agggaaagta agccaaggct       120
cattatgcca aagganatat acatttcaat tctccaaact tcttcctcat tccaagagtt       180
ttcaatattt gcatgaacct gctgataanc catgttaana aacaaatatc tctctnacct       240
tctcatcggt                                                             250

<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214
acccagaatc caatgctgaa tatttggctt cattattccc agattctttg attgtcaaag        60
gatttaatgt tgtctcagct tgggcacttc agttaggacc taaggatgcc agccggcagg       120
tttatatatg cagcaacaat attcaagcgc gacaacaggt tattgaactt gcccgccagt       180
tgaatttcat tcccattgac ttgggatcct tatcatcagc canagagatt gaaaatttac       240
ccctacgact ctttactctc tggagagggc cagtggtggt agctataagc ttggccacat       300
ttttttttcc tttattcctt tgtcagagat gcgattcatc catatgctan aaaccaacag       360
agtgactttt acaaaattcc tataganatt gtgaataaaa ccttacctat agttgccatt       420
actttgctct ccctaatata cctc                                             444

<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215
acttatgagc agagcgacat atccaagtgt anactgaata aaactgaatt ctctccagtt        60
taaagcattg ctcactgaag ggatagaagt gactgccagg agggaaagta agccaaggct       120
cattatgcca aagganatat acatttcaat tctccaaact tcttcctcat tccaagagtt       180
ttcaatattt gcatgaacct gctgataagc catgttgaga aacaaatatc tctctgacct       240
tctcatcggt aagcagaggc tgtaggcaac atggaccata gcgaanaaaa aacttagtaa       300
tccaagctgt tttctacact gtaaccaggt ttccaaccaa ggtggaaatc tcctatactt       360
ggtgcc                                                                 366

<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 216
ctgtataaac agaactccac tgcangaggg agggccgggc caggagaatc tccgcttgtc        60
caagacaggg gcctaaggag ggtctccaca ctgctnntaa gggctnttnc atttttttat       120
```

```
taataaaaag tnnaaaaggc ctcttctcaa cttttttccc ttnggctgga aaatttaaaa      180
atcaaaaatt tcctnaagtt ntcaagctat catatatact ntatcctgaa aaagcaacat      240
aattcttcct tccctccttt                                                  260

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217
acctacgtgg gtaagtttan aaatgttata atttcaggaa naggaacgca tataattgta       60
tcttgcctat aattttctat tttaataagg aaatagcaaa ttggggtggg gggaatgtag      120
ggcattctac agtttgagca aaatgcaatt aaatgtggaa ggacagcact gaaaaatttt      180
atgaataatc tgtatgatta tatgtctcta gagtagattt ataattagcc acttacccta      240
atatccttca tgcttgtaaa gt                                               262

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218
accaaggtgg tgcattaccg gaantggatc aangacacca tcgtggccaa cccctgagca       60 ccctatcaa ctccctttg tagtaaactt ggaaccttgg aaatgaccag gccaagactc       120
aggcctcccc agttctactg acctttgtcc ttangtntna ngtccagggt tgctaggaaa      180
anaaatcagc agacacaggt gtaaa                                            205

<210> SEQ ID NO 219
<211> LENGTH: 114
<212> TYPE: DNA
<213> ORGANISM: Homo sapien

<400> SEQUENCE: 219
tactgttttg tctcagtaac aataaataca aaagactgg ttgtgttccg gccccatcca       60
accacgaagt tgatttctct tgtgtgcaga gtgactgatt ttaaaggaca tgga           114

<210> SEQ ID NO 220
<211> LENGTH: 93
<212> TYPE: DNA
<213> ORGANISM: Homo sapien

<400> SEQUENCE: 220
actagccagc acaaaaggca gggtagcctg aattgctttc tgctctttac atttcttta       60 aaataagcat ttagtgctca gtccctactg agt                                    93

<210> SEQ ID NO 221
<211> LENGTH: 167
<212> TYPE: DNA
<213> ORGANISM: Homo sapien
<220> FEATURE:
```

<221> NAME/KEY: misc_feature
<222> LOCATION: (1)...(167)
<223> OTHER INFORMATION: n = A,T,C or G

<400> SEQUENCE: 221

| | |
|---|---|
| actangtgca ggtgcgcaca aatatttgtc gatattccct tcatcttgga ttccatgagg | 60 |
| tcttttgccc agcctgtggc tctactgtag taagtttctg ctgatgagga gccagnatgc | 120 |
| cccccactac cttccctgac gctccccana aatcacccaa cctctgt | 167 |

<210> SEQ ID NO 222
<211> LENGTH: 351
<212> TYPE: DNA
<213> ORGANISM: Homo sapien

<400> SEQUENCE: 222

| | |
|---|---|
| agggcgtggt gcggagggcg gtactgacct cattagtagg aggatgcatt ctggcacccc | 60 |
| gttcttcacc tgtcccccaa tccttaaaag gccatactgc ataaagtcaa caacagataa | 120 |
| atgtttgctg aattaaagga tggatgaaaa aaattaataa tgaatttttg cataatccaa | 180 |
| ttttctcttt tatatttcta gaagaagttt ctttgagcct attagatccc gggaatcttt | 240 |
| taggtgagca tgattagaga gcttgtaggt tgcttttaca tatatctggc atatttgagt | 300 |
| ctcgtatcaa aacaatagat tggtaaaggt ggtattattg tattgataag t | 351 |

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223

| | |
|---|---|
| aaaacaaaca aacaaaaaaa acaattcttc attcagaaaa attatcttag ggactgatat | 60 |
| tggtaattat ggtcaattta atwrtrttkt ggggcatttc cttacattgt cttgacaaga | 120 |
| ttaaaatgtc tgtgccaaaa ttttgtattt tatttggaga cttcttatca aaagtaatgc | 180 |
| tgccaaagga agtctaagga attagtagtg ttcccmtcac ttgtttggag tgtgctattc | 240 |
| taaaagattt tgatttcctg gaatgacaat tatatttttaa cttggtggg ggaaanagtt | 300 |
| ataggaccac agtcttcact tctgatactt gtaaattaat cttttattgc acttgttttg | 360 |
| accattaagc tatatgttta aaa | 383 |

<210> SEQ ID NO 224
<211> LENGTH: 320
<212> TYPE: DNA
<213> ORGANISM: Homo sapien

<400> SEQUENCE: 224

| | |
|---|---|
| cccctgaagg cttcttgtta gaaaatagta cagttacaac caataggaac aacaaaaaga | 60 |
| aaagtttgt gacattgtag tagggagtgt gtacccctta ctccccatca aaaaaaaaat | 120 |
| ggatacatgg ttaaaggata raagggcaat attttatcat atgttctaaa agagaaggaa | 180 |
| gagaaaatac tactttctcr aaatggaagc ccttaaaggt gctttgatac tgaaggacac | 240 |
| aaatgtggcc gtccatcctc ctttaragtt gcatgacttg gacacggtaa ctgttgcagt | 300 |
| tttaractcm gcattgtgac | 320 |

<210> SEQ ID NO 225
<211> LENGTH: 1214
<212> TYPE: DNA
<213> ORGANISM: Homo sapien

<400> SEQUENCE: 225

| | | | | | |
|---|---|---|---|---|---|
| gaggactgca | gcccgcactc | gcagccctgg | caggcggcac | tggtcatgga | aaacgaattg | 60 |
| ttctgctcgg | gcgtcctggt | gcatccgcag | tgggtgctgt | cagccgcaca | ctgtttccag | 120 |
| aactcctaca | ccatcgggct | gggcctgcac | agtcttgagg | ccgaccaaga | gccagggagc | 180 |
| cagatggtgg | aggccagcct | ctccgtacgg | cacccagagt | acaacagacc | cttgctcgct | 240 |
| aacgacctca | tgctcatcaa | gttggacgaa | tccgtgtccg | agtctgacac | catccggagc | 300 |
| atcagcattg | cttcgcagtg | ccctaccgcg | gggaactctt | gcctcgtttc | tggctggggt | 360 |
| ctgctggcga | acggcagaat | gcctaccgtg | ctgcagtgcg | tgaacgtgtc | ggtggtgtct | 420 |
| gaggaggtct | gcagtaagct | ctatgacccg | ctgtaccacc | ccagcatgtt | ctgcgccggc | 480 |
| ggagggcaag | accagaagga | ctcctgcaac | ggtgactctg | ggggcccct | gatctgcaac | 540 |
| gggtacttgc | agggccttgt | gtctttcgga | aagccccgt | gtggccaagt | tggcgtgcca | 600 |
| ggtgtctaca | ccaacctctg | caaattcact | gagtggatag | agaaaaccgt | ccaggccagt | 660 |
| taactctggg | gactgggaac | ccatgaaatt | gaccccaaa | tacatcctgc | ggaaggaatt | 720 |
| caggaatatc | tgttcccagc | ccctcctccc | tcaggcccag | gagtccaggc | cccagcccc | 780 |
| tcctccctca | aaccaagggt | acagatcccc | agcccctcct | ccctcagacc | caggagtcca | 840 |
| gaccccccag | cccctcctcc | ctcagaccca | ggagtccagc | ccctcctccc | tcagacccag | 900 |
| gagtccagac | cccccagccc | ctcctccctc | agacccaggg | gtccaggccc | caaccctc | 960 |
| ctccctcaga | ctcagaggtc | caagccccca | cccctccctt | ccccagaccc | agaggtccag | 1020 |
| gtcccagccc | ctcctccctc | agacccagcg | gtccaatgcc | acctagactc | tccctgtaca | 1080 |
| cagtgccccc | ttgtggcacg | ttgacccaac | cttaccagtt | ggttttttcat | tttttgtccc | 1140 |
| tttccctag | atccagaaat | aaagtctaag | agaagcgcaa | aaaaaaaaaa | aaaaaaaaa | 1200 |
| aaaaaaaaaa | aaaa | | | | | 1214 |

<210> SEQ ID NO 226
<211> LENGTH: 119
<212> TYPE: DNA
<213> ORGANISM: Homo sapien

<400> SEQUENCE: 226

| | | | | | |
|---|---|---|---|---|---|
| acccagtatg | tgcagggaga | cggaacccca | tgtgacagcc | cactccacca | gggttcccaa | 60 |
| agaacctggc | ccagtcataa | tcattcatcc | tgacagtggc | aataatcacg | ataaccagt | 119 |

<210> SEQ ID NO 227
<211> LENGTH: 818
<212> TYPE: DNA
<213> ORGANISM: Homo sapien

<400> SEQUENCE: 227

| | | | | | |
|---|---|---|---|---|---|
| acaattcata | gggacgacca | atgaggacag | ggaatgaacc | cggctctccc | ccagccctga | 60 |
| tttttgctac | atatggggtc | ccttttcatt | cttttgcaaaa | acactgggtt | ttctgagaac | 120 |
| acggacggtt | cttagcacaa | tttgtgaaat | ctgtgtaraa | ccgggctttg | cagggagat | 180 |
| aattttcctc | ctctggagga | aagtggtga | ttgacaggca | gggagacagt | gacaaggcta | 240 |
| gagaaagcca | cgctcggcct | tctctgaacc | aggatggaac | ggcagacccc | tgaaaacgaa | 300 |

```
gcttgtcccc ttccaatcag ccacttctga gaaccccccat ctaacttcct actgaaaaag      360
agggcctcct caggagcagt ccaagagttt tcaaagataa cgtgacaact accatctaga      420
ggaaagggtg caccctcagc agagaagccg agagcttaac tctggtcgtt tccagagaca      480
acctgctggc tgtcttggga tgcgcccagc ctttgagagg ccactacccc atgaacttct      540
gccatccact ggacatgaag ctgaggcaca tgggcttcaa cactgagttg tcatgagagg      600
gacaggctct gccctcaagc cggctgaggg cagcaaccac tctcctcccc tttctcacgc      660
aaagccattc ccacaaatcc agaccatacc atgaagcaac gagacccaaa cagtttggct      720
caagaggata tgaggactgt ctcagcctgg ctttgggctg acaccatgca cacacacaag      780
gtccacttct aggttttcag cctagatggg agtcgtgt                              818

<210> SEQ ID NO 228
<211> LENGTH: 744
<212> TYPE: DNA
<213> ORGANISM: Homo sapien

<400> SEQUENCE: 228
actggagaca ctgttgaact tgatcaagac ccagaccacc ccaggtctcc ttcgtgggat       60
gtcatgacgt tgacatacc tttggaacga gcctcctcct tggaagatgg aagaccgtgt      120
tcgtggccga cctggcctct cctggcctgt ttcttaagat gcggagtcac atttcaatgg      180
taggaaaagt ggcttcgtaa aatagaagag cagtcactgt ggaactacca aatggcgaga      240
tgctcggtgc acattgggt gctttgggat aaaagattta tgagccaact attctctggc      300
accagattct aggccagttt gttccactga agcttttccc acagcagtcc acctctgcag      360
gctggcagct gaatggcttg ccggtggctc tgtggcaaga tcacactgag atcgatgggt      420
gagaaggcta ggatgcttgt ctagtgttct tagctgtcac gttggctcct tccaggttgg      480
ccagacggtt ttggccactc ccttctaaaa cacaggcgcc ctcctggtga cagtgacccg      540
ccgtggtatg ccttggccca ttccagcagt cccagttatg catttcaagt ttggggtttg      600
ttcttttcgt taatgttcct ctgtgttgtc agctgtcttc atttcctggg ctaagcagca      660
ttgggagatg tggaccagag atccactcct taagaaccag tggcgaaaga cactttcttt      720
cttcactctg aagtagctgg tggt                                             744

<210> SEQ ID NO 229
<211> LENGTH: 300
<212> TYPE: DNA
<213> ORGANISM: Homo sapien

<400> SEQUENCE: 229
cgagtctggg ttttgtctat aaagtttgat ccctcctttt ctcatccaaa tcatgtgaac       60
cattacacat cgaaataaaa gaaaggtggc agacttgccc aacgccaggc tgacatgtgc      120
tgcagggttg ttgttttta attattattg ttagaaacgt cacccacagt ccctgttaat      180
ttgtatgtga cagccaactc tgagaaggtc ctatttttcc acctgcagag gatccagtct      240
cactaggctc ctccttgccc tcacactgga gtctccgcca gtgtgggtgc ccactgacat      300

<210> SEQ ID NO 230
<211> LENGTH: 301
<212> TYPE: DNA
<213> ORGANISM: Homo sapien

<400> SEQUENCE: 230
cagcagaaca aatacaaata tgaagagtgc aaagatctca taaaatctat gctgaggaat       60
```

```
gagcgacagt tcaaggagga gaagcttgca gagcagctca agcaagctga ggagctcagg      120
caatataaag tcctggttca cactcaggaa cgagagctga cccagttaag ggagaagttg      180
cgggaaggga gagatgcctc cctctcattg aatgagcatc tccaggccct cctcactccg      240
gatgaaccgg acaagtccca ggggcaggac ctccaagaaa cagacctcgg ccgcgaccac      300
g                                                                     301

<210> SEQ ID NO 231
<211> LENGTH: 301
<212> TYPE: DNA
<213> ORGANISM: Homo sapien

<400> SEQUENCE: 231
gcaagcacgc tggcaaatct ctgtcaggtc agctccagag aagccattag tcattttagc      60
caggaactcc aagtccacat ccttggcaac tggggacttg cgcaggttag ccttgaggat      120
ggcaacacgg gacttctcat caggaagtgg gatgtagatg agctgatcaa gacggccagg      180
tctgaggatg gcaggatcaa tgatgtcagg ccggttggta ccgccaatga tgaacacatt      240 ttttttgtg gacatgccat ccatttctgt caggatctgg ttgatgactc ggtcagcagc      300
c                                                                     301

<210> SEQ ID NO 232
<211> LENGTH: 301
<212> TYPE: DNA
<213> ORGANISM: Homo sapien

<400> SEQUENCE: 232
agtaggtatt tcgtgagaag ttcaacacca aaactggaac atagttctcc ttcaagtgtt      60
ggcgacagcg gggcttcctg attctggaat ataactttgt gtaaattaac agccacctat      120
agaagagtcc atctgctgtg aaggagagac agagaactct gggttccgtc gtcctgtcca      180
cgtgctgtac caagtgctgg tgccagcctg ttacctgttc tcactgaaaa tctggctaat      240
gctcttgtgt atcacttctg attctgacaa tcaatcaatc aatggcctag agcactgact      300
g                                                                     301

<210> SEQ ID NO 233
<211> LENGTH: 301
<212> TYPE: DNA
<213> ORGANISM: Homo sapien

<400> SEQUENCE: 233
atgactgact tcccagtaag gctctctaag gggtaagtag gaggatccac aggatttgag      60
atgctaaggc cccagagatc gtttgatcca accctcttat tttcagaggg gaaaatgggg      120
cctagaagtt acagagcatc tagctggtgc gctggcaccc ctggcctcac acagactccc      180
gagtagctgg gactacaggc acacagtcac tgaagcaggc cctgttagca attctatgcg      240
tacaaattaa catgagatga gtagagactt tattgagaaa gcaagagaaa atcctatcaa      300
c                                                                     301

<210> SEQ ID NO 234
<211> LENGTH: 301
<212> TYPE: DNA
<213> ORGANISM: Homo sapien

<400> SEQUENCE: 234
```

-continued

| | |
|---|---|
| aggtcctaca catcgagact catccatgat tgatatgaat ttaaaaatta caagcaaaga | 60 |
| catttattc atcatgatgc tttctttgt ttcttctttt cgttttcttc tttttctttt | 120 |
| tcaatttcag caacatactt ctcaatttct tcaggattta aaatcttgag ggattgatct | 180 |
| cgcctcatga cagcaagttc aatgtttttg ccacctgact gaaccacttc caggagtgcc | 240 |
| ttgatcacca gcttaatggt cagatcatct gcttcaatgg cttcgtcagt atagttcttc | 300 |
| t | 301 |

<210> SEQ ID NO 235
<211> LENGTH: 283
<212> TYPE: DNA
<213> ORGANISM: Homo sapien

<400> SEQUENCE: 235

| | |
|---|---|
| tgggctgtg catcaggcgg gtttgagaaa tattcaattc tcagcagaag ccagaatttg | 60 |
| aattccctca tcttttaggg aatcatttac caggtttgga gaggattcag acagctcagg | 120 |
| tgctttcact aatgtctctg aacttctgtc cctctttgtt catggatagt ccaataaata | 180 |
| atgttatctt tgaactgatg ctcataggag agaatataag aactctgagt gatatcaaca | 240 |
| ttagggattc aaagaaatat tagatttaag ctcacactgg tca | 283 |

<210> SEQ ID NO 236
<211> LENGTH: 301
<212> TYPE: DNA
<213> ORGANISM: Homo sapien

<400> SEQUENCE: 236

| | |
|---|---|
| aggtcctcca ccaactgcct gaagcacggt taaaattggg aagaagtata gtgcagcata | 60 |
| aatactttta aatcgatcag atttccctaa cccacatgca atcttcttca ccagaagagg | 120 |
| tcggagcagc atcattaata ccaagcagaa tgcgtaatag ataaatacaa tggtatatag | 180 |
| tgggtagacg gcttcatgag tacagtgtac tgtggtatcg taatctggac ttgggttgta | 240 |
| aagcatcgtg taccagtcag aaagcatcaa tactcgacat gaacgaatat aagaacacc | 300 |
| a | 301 |

<210> SEQ ID NO 237
<211> LENGTH: 301
<212> TYPE: DNA
<213> ORGANISM: Homo sapien

<400> SEQUENCE: 237

| | |
|---|---|
| cagtggtagt ggtggtggac gtggcgttgg tcgtggtgcc ttttttggtg cccgtcacaa | 60 |
| actcaatttt tgttcgctcc tttttggcct tttccaattt gtccatctca attttctggg | 120 |
| ccttggctaa tgcctcatag taggagtcct cagaccagcc atggggatca aacatatcct | 180 |
| ttgggtagtt ggtgccaagc tcgtcaatgg cacagaatgg atcagcttct cgtaaatcta | 240 |
| gggttccgaa attctttctt cctttggata atgtagttca tatccattcc ctcctttatc | 300 |
| t | 301 |

<210> SEQ ID NO 238
<211> LENGTH: 301
<212> TYPE: DNA
<213> ORGANISM: Homo sapien

<400> SEQUENCE: 238

| | |
|---|---|
| gggcaggttt tttttttttt tttttgatg gtgcagaccc ttgctttatt tgtctgactt | 60 |

```
gttcacagtt cagcccoctg ctcagaaaac caacgggcca gctaaggaga ggaggaggca    120
ccttgagact tccggagtcg aggctctcca gggttcccca gcccatcaat cattttctgc    180 acccoctgcc tgggaagcag ctccctgggg ggtgggaatg ggtgactaga agggatttca    240
gtgtgggacc cagggtctgt tcttcacagt aggaggtgga agggatgact aatttctta    300 t                                                                   301
```

<210> SEQ ID NO 239
<211> LENGTH: 239
<212> TYPE: DNA
<213> ORGANISM: Homo sapien

<400> SEQUENCE: 239

```
ataagcagct agggaattct ttatttagta atgtcctaac ataaaagttc acataactgc    60
ttctgtcaaa ccatgatact gagctttgtg acaacccaga ataactaag agaaggcaaa    120 cataatacct tagagatcaa gaaacattta cacagttcaa ctgtttaaaa atagctcaac    180
attcagccag tgagtagagt gtgaatgcca gcatacacag tatacaggtc cttcaggga    239
```

<210> SEQ ID NO 240
<211> LENGTH: 300
<212> TYPE: DNA
<213> ORGANISM: Homo sapien

<400> SEQUENCE: 240

```
ggtcctaatg aagcagcagc ttccacattt taacgcaggt ttacggtgat actgtccttt    60
gggatctgcc ctccagtgga accttttaag gaagaagtgg gcccaagcta agttccacat    120
gctgggtgag ccagatgact tctgttccct ggtcactttc ttcaatgggg cgaatggggg    180
ctgccaggtt tttaaaatca tgcttcatct tgaagcacac ggtcacttca ccctcctcac    240
gctgtgggtg tactttgatg aaaatacccca ctttgttggc cttctgaag ctataatgtc    300
```

<210> SEQ ID NO 241
<211> LENGTH: 301
<212> TYPE: DNA
<213> ORGANISM: Homo sapien

<400> SEQUENCE: 241

```
gaggtctggt gctgaggtct ctgggctagg aagaggagtt ctgtggagct ggaagccaga    60
cctctttgga ggaaactcca gcagctatgt tggtgtctct gagggaatgc aacaaggctg    120
ctcctccatg tattggaaaa ctgcaaactg gactcaactg gaaggaagtg ctgctgccag    180
tgtgaagaac cagcctgagg tgacagaaac ggaagcaaac aggaacagcc agtcttttct    240
tcctcctcct gtcatacggt ctctctcaag catcctttgt tgtcaggggc taaaaggga    300 g                                                                   301
```

<210> SEQ ID NO 242
<211> LENGTH: 301
<212> TYPE: DNA
<213> ORGANISM: Homo sapien

<400> SEQUENCE: 242

```
ccgaggtcct gggatgcaac caatcactct gtttcacgtg acttttatca ccatacaatt    60
tgtggcattt cctcattttc tacattgtag aatcaagagt gtaaataaat gtatatcgat    120
gtcttcaaga atatatcatt ccttttttcac tagaacccat tcaaaatata agtcaagaat    180
```

| | |
|---|---|
| cttaatatca acaaatatat caagcaaact ggaaggcaga ataactacca taatttagta | 240 |
| taagtaccca aagttttata aatcaaaagc cctaatgata accatttta gaattcaatc | 300 |
| a | 301 |

<210> SEQ ID NO 243
<211> LENGTH: 301
<212> TYPE: DNA
<213> ORGANISM: Homo sapien

<400> SEQUENCE: 243

| | |
|---|---|
| aggtaagtcc cagtttgaag ctcaaaagat ctggtatgag cataggctca tcgacgacat | 60 |
| ggtggcccaa gctatgaaat cagagggagg cttcatctgg gcctgtaaaa actatgatgg | 120 |
| tgacgtgcag tcggactctg tggcccaagg gtatggctct ctcggcatga tgaccagcgt | 180 |
| gctggtttgt ccagatggca agacagtaga agcagaggct gcccacggga ctgtaacccg | 240 |
| tcactaccgc atgttccaga aggacagga gacgtccacc aatcccattg cttccatttt | 300 |
| t | 301 |

<210> SEQ ID NO 244
<211> LENGTH: 300
<212> TYPE: DNA
<213> ORGANISM: Homo sapien

<400> SEQUENCE: 244

| | |
|---|---|
| gctggtttgc aagaatgaaa tgaatgattc tacagctagg acttaacctt gaaatggaaa | 60 |
| gtcatgcaat cccatttgca ggatctgtct gtgcacatgc ctctgtagag agcagcattc | 120 |
| ccagggacct tggaaacagt tgacactgta aggtgcttgc tccccaagac acatcctaaa | 180 |
| aggtgttgta atggtgaaaa cgtcttcctt ctttattgcc ccttcttatt tatgtgaaca | 240 |
| actgtttgtc ttttgtgtat cttttttaaa ctgtaaagtt caattgtgaa aatgaatatc | 300 |

<210> SEQ ID NO 245
<211> LENGTH: 301
<212> TYPE: DNA
<213> ORGANISM: Homo sapien

<400> SEQUENCE: 245

| | |
|---|---|
| gtctgagtat ttaaaatgtt attgaaatta tccccaacca atgttagaaa agaaagaggt | 60 |
| tatatactta gataaaaaat gaggtgaatt actatccatt gaaatcatgc tcttagaatt | 120 |
| aaggccagga gatattgtca ttaatgtara cttcaggaca ctagagtata gcagccctat | 180 |
| gttttcaaag agcagagatg caattaaata ttgtttagca tcaaaaaggc cactcaatac | 240 |
| agctaataaa atgaaagacc taatttctaa agcaattctt tataatttac aaagttttaa | 300 |
| g | 301 |

<210> SEQ ID NO 246
<211> LENGTH: 301
<212> TYPE: DNA
<213> ORGANISM: Homo sapien

<400> SEQUENCE: 246

| | |
|---|---|
| ggtctgtcct acaatgcctg cttcttgaaa gaagtcggca ctttctagaa tagctaaata | 60 |
| acctgggctt attttaaaga actatttgta gctcagattg gttttcctat ggctaaaata | 120 |
| agtgcttctt gtgaaaatta aataaaacag ttaattcaaa gccttgatat atgttaccac | 180 |
| taacaatcat actaaatata ttttgaagta caaagtttga catgctctaa agtgacaacc | 240 |

```
caaatgtgtc ttacaaaaca cgttcctaac aaggtatgct ttacactacc aatgcagaaa    300
c                                                                   301
```

<210> SEQ ID NO 247
<211> LENGTH: 301
<212> TYPE: DNA
<213> ORGANISM: Homo sapien

<400> SEQUENCE: 247

```
aggtcctttg gcagggctca tgatcagag ctcaaactgg agggaaaggc atttcgggta     60
gcctaagagg gcgactggcg gcagcacaac caaggaaggc aaggttgttt cccccacgct   120
gtgtcctgtg ttcaggtgcg acacacaatc ctcatgggaa caggatcacc catgcgctgc   180
ccttgatgat caaggttggg gcttaagtgg attaaggag gcaagttctg ggttccttgc   240
cttttcaaac catgaagtca ggctctgtat ccctcctttt cctaactgat attctaacta   300
a                                                                   301
```

<210> SEQ ID NO 248
<211> LENGTH: 301
<212> TYPE: DNA
<213> ORGANISM: Homo sapien

<400> SEQUENCE: 248

```
aggtccttgg agatgccatt tcagccgaag gactcttctw ttcggaagta caccctcact    60
attaggaaga ttcttagggg taattttct gaggaaggag aactagccaa cttaagaatt   120
acaggaagaa agtggtttgg aagacagcca agaaataaa agcagattaa attgtatcag   180
gtacattcca gcctgttggc aactccataa aaacatttca gattttaatc ccgaatttag   240
ctaatgagac tggatttttg ttttttatgt tgtgtgtcgc agagctaaaa actcagttcc   300
c                                                                   301
```

<210> SEQ ID NO 249
<211> LENGTH: 301
<212> TYPE: DNA
<213> ORGANISM: Homo sapien

<400> SEQUENCE: 249

```
gtccagagga agcacctggt gctgaactag gcttgccctg ctgtgaactt gcacttggag    60
ccctgacgct gctgttctcc ccgaaaaacc cgaccgacct ccgcgatctc cgtcccgccc   120
ccagggagac acagcagtga ctcagagctg gtcgcacact gtgcctccct cctcaccgcc   180
catcgtaatg aattattttg aaaattaatt ccaccatcct ttcagattct ggatggaaag   240
actgaatctt tgactcagaa ttgtttgctg aaaagaatga tgtgactttc ttagtcattt   300
a                                                                   301
```

<210> SEQ ID NO 250
<211> LENGTH: 301
<212> TYPE: DNA
<213> ORGANISM: Homo sapien

<400> SEQUENCE: 250

```
ggtctgtgac aaggacttgc aggctgtggg aggcaagtga cccttaacac tacacttctc    60
cttatcttta ttggcttgat aaacataatt atttctaaca ctagcttatt tccagttgcc   120
cataagcaca tcagtacttt tctctggctg gaatagtaaa ctaaagtatg gtacatctac   180
```

```
ctaaaagact actatgtgga ataatacata ctaatgaagt attacatgat ttaaagacta      240
caataaaacc aaacatgctt ataacattaa gaaaaacaat aaagatacat gattgaaacc      300
a                                                                     301
```

<210> SEQ ID NO 251
<211> LENGTH: 301
<212> TYPE: DNA
<213> ORGANISM: Homo sapien

<400> SEQUENCE: 251

```
gccgaggtcc tacatttggc ccagtttccc cctgcatcct ctccagggcc cctgcctcat       60
agacaacctc atagagcata ggagaactgg ttgccctggg ggcaggggga ctgtctggat      120 ggcagggggtc ctcaaaaatg ccactgtcac tgccaggaaa tgcttctgag cagtacacct    180
cattgggatc aatgaaaagc ttcaagaaat cttcaggctc actctcttga aggcccggaa     240
cctctggagg ggggcagtgg aatcccagct ccaggacgga tcctgtcgaa aagatatcct    300
c                                                                     301
```

<210> SEQ ID NO 252
<211> LENGTH: 301
<212> TYPE: DNA
<213> ORGANISM: Homo sapien

<400> SEQUENCE: 252

```
gcaaccaatc actctgtttc acgtgacttt tatcaccata caatttgtgg catttcctca      60
ttttctacat tgtagaatca agagtgtaaa taaatgtata tcgatgtctt caagaatata    120
tcattccttt tcactagga acccattcaa aatataagtc aagaatctta atatcaacaa     180
atatatcaag caaactggaa ggcagaataa ctaccataat ttagtataag tacccaaagt     240
tttataaatc aaaagcccta atgataacca tttttagaat tcaatcatca ctgtagaatc    300
a                                                                     301
```

<210> SEQ ID NO 253
<211> LENGTH: 301
<212> TYPE: DNA
<213> ORGANISM: Homo sapien

<400> SEQUENCE: 253

```
ttccctaaga agatgttatt ttgttgggtt ttgttccccc tccatctcga ttctcgtacc      60
caactaaaaa aaaaaaataa agaaaaaatg tgctgcgttc tgaaaaataa ctccttagct    120
tggtctgatt gttttcagac cttaaaatat aaacttgttt cacaagcttt aatccatgtg    180
gatttttttt cttagagaac cacaaaacat aaaaggagca agtcggactg aatacctgtt     240
tccatagtgc ccacagggta ttcctcacat tttctccata ggaaaatgct ttttcccaag    300
g                                                                     301
```

<210> SEQ ID NO 254
<211> LENGTH: 301
<212> TYPE: DNA
<213> ORGANISM: Homo sapien

<400> SEQUENCE: 254

```
cgctgcgcct ttcccttggg ggagggcaa ggccagaggg ggtccaagtg cagcacgagg       60
aacttgacca attcccttga agcgggtggg ttaaaccctg taaatgggaa caaaatcccc    120
ccaaatctct tcatcttacc ctggtggact cctgactgta gaattttttg gttgaaacaa    180
```

```
gaaaaaaata aagctttgga cttttcaagg ttgcttaaca ggtactgaaa gactggcctc      240
acttaaactg agccaggaaa agctgcagat ttattaatgg gtgtgttagt gtgcagtgcc      300
t                                                                       301
```

<210> SEQ ID NO 255
<211> LENGTH: 302
<212> TYPE: DNA
<213> ORGANISM: Homo sapien

<400> SEQUENCE: 255

```
agcttttttt tttttttttt tttttttttt ttcattaaaa aatagtgctc tttattataa       60
attactgaaa tgtttctttt ctgaatataa atataaatat gtgcaaagtt tgacttggat      120
tgggattttg ttgagttctt caagcatctc ctaatacct caagggcctg agtagggggg       180
aggaaaaagg actggaggtg gaatctttat aaaaaacaag agtgattgag gcagattgta      240
aacattatta aaaacaaga acaaacaaa aaatagaga aaaaaccac cccaacacac         300 aa                                                                     302
```

<210> SEQ ID NO 256
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 256

```
gttccagaaa acattgaagg tggcttccca aagtctaact agggataccc cctctagcct       60
aggaccctcc tccccacacc tcaatccacc aaaccatcca taatgcaccc agataggccc      120 accccaaaa gcctggacac cttgagcaca cagttatgac caggacagac tcatctctat       180
aggcaaatag ctgctggcaa actggcatta cctggtttgt ggggatgggg gggcaagtgt      240
gtggcctctc ggcctggtta gcaagaacat tcagggtagg cctaagttan tcgtgttagt      300
t                                                                       301
```

<210> SEQ ID NO 257
<211> LENGTH: 301
<212> TYPE: DNA
<213> ORGANISM: Homo sapien

<400> SEQUENCE: 257

```
gttgtggagg aactctggct tgctcattaa gtcctactga ttttcactat ccctgaatt       60 tccccactta tttttgtctt tcactatcgc aggccttaga agaggtctac ctgcctccag      120
tcttacctag tccagtctac cccctggagt tagaatggcc atcctgaagt gaaaagtaat      180
gtcacattac tcccttcagt gatttcttgt agaagtgcca atccctgaat gccaccaaga     240
tcttaatctt cacatctta atcttatctc tttgactcct ctttacaccg gagaaggctc      300
c                                                                       301
```

<210> SEQ ID NO 258
<211> LENGTH: 301
<212> TYPE: DNA
<213> ORGANISM: Homo sapien
<220> FEATURE:
<221> NAME/KEY: misc_feature
<222> LOCATION: (1)...(301)

<223> OTHER INFORMATION: n = A,T,C or G

<400> SEQUENCE: 258

| | | | | | |
|---|---|---|---|---|---|
| cagcagtagt | agatgccgta | tgccagcacg | cccagcactc | ccaggatcag | caccagcacc | 60
| aggggcccag | ccaccaggcg | cagaagcaag | ataaacagta | ggctcaagac | cagagccacc | 120
| cccagggcaa | caagaatcca | ataccaggac | tgggcaaaat | cttcaaagat | cttaacactg | 180
| atgtctcggg | cattgaggct | gtcaataana | cgctgatccc | ctgctgtatg | gtggtgtcat | 240
| tggtgatccc | tgggagcgcc | ggtggagtaa | cgttggtcca | tggaaagcag | cgcccacaac | 300
| t | | | | | 301

<210> SEQ ID NO 259
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 259

| | | | | | |
|---|---|---|---|---|---|
| tcatatatgc | aaacaaatgc | agactangcc | tcaggcagag | actaaaggac | atctcttggg | 60
| gtgtcctgaa | gtgatttgga | cccctgaggg | cagacaccta | agtaggaatc | ccagtgggaa | 120
| gcaaagccat | aaggaagccc | aggattcctt | gtgatcagga | agtgggccag | gaaggtctgt | 180
| tccagctcac | atctcatctg | catgcagcac | ggaccggatg | cgcccactgg | gtcttggctt | 240
| ccctcccatc | ttctcaagca | gtgtccttgt | tgagccattt | gcatccttgg | ctccaggtgg | 300
| c | | | | | 301

<210> SEQ ID NO 260
<211> LENGTH: 301
<212> TYPE: DNA
<213> ORGANISM: Homo sapien

<400> SEQUENCE: 260

| | | | | | |
|---|---|---|---|---|---|
| tttttttct | ccctaaggaa | aaagaaggaa | caagtctcat | aaaaccaaat | aagcaatggt | 60
| aaggtgtctt | aacttgaaaa | agattaggag | tcactggttt | acaagttata | attgaatgaa | 120
| agaactgtaa | cagccacagt | tggccatttc | atgccaatgg | cagcaaacaa | caggattaac | 180
| tagggcaaaa | taaataagtg | tgtggaagcc | ctgataagtg | cttaataaac | agactgattc | 240
| actgagacat | cagtacctgc | ccgggcggcc | gctcgagccg | aattctgcag | atatccatca | 300
| c | | | | | 301

<210> SEQ ID NO 261
<211> LENGTH: 301
<212> TYPE: DNA
<213> ORGANISM: Homo sapien

<400> SEQUENCE: 261

| | | | | | |
|---|---|---|---|---|---|
| aaatattcga | gcaaatcctg | taactaatgt | gtctccataa | aaggctttga | actcagtgaa | 60
| tctgcttcca | tccacgattc | tagcaatgac | ctctcggaca | tcaaagctcc | tcttaaggtt | 120
| agcaccaact | attccataca | attcatcagc | aggaaataaa | ggctcttcag | aaggttcaat | 180
| ggtgacatcc | aatttcttct | gataatttag | attcctcaca | accttcctag | ttaagtgaag | 240
| ggcatgatga | tcatccaaag | cccagtggtc | acttactcca | gactttctgc | aatgaagatc | 300
| a | | | | | 301

<210> SEQ ID NO 262
<211> LENGTH: 301
<212> TYPE: DNA
<213> ORGANISM: Homo sapien

<400> SEQUENCE: 262

| | | | | | |
|---|---|---|---|---|---|
| gaggagagcc | tgttacagca | tttgtaagca | cagaatactc | caggagtatt | tgtaattgtc | 60 |
| tgtgagcttc | ttgccgcaag | tctctcagaa | atttaaaaag | atgcaaatcc | ctgagtcacc | 120 |
| cctagacttc | ctaaaccaga | tcctctgggg | ctggaacctg | gcactctgca | tttgtaatga | 180 |
| gggctttctg | gtgcacacct | aattttgtgc | atctttgccc | taaatcctgg | attagtgccc | 240 |
| catcattacc | cccacattat | aatgggatag | attcagagca | gatactctcc | agcaaagaat | 300 |
| c | | | | | | 301 |

<210> SEQ ID NO 263
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 263

| | | | | | |
|---|---|---|---|---|---|
| tttagcttgt | ggtaaatgac | tcacaaaact | gattttaaaa | tcaagttaat | gtgaattttg | 60 |
| aaaattacta | cttaatccta | attcacaata | acaatggcat | taaggtttga | cttgagttgg | 120 |
| ttcttagtat | tatttatggt | aaataggctc | ttaccacttg | caaataactg | gcccacatcat | 180 |
| taatgactga | cttcccagta | aggctctcta | aggggtaagt | angaggatcc | acaggatttg | 240 |
| agatgctaag | gccccagaga | tcgtttgatc | caaccctctt | attttcagag | gggaaaatgg | 300 |
| g | | | | | | 301 |

<210> SEQ ID NO 264
<211> LENGTH: 301
<212> TYPE: DNA
<213> ORGANISM: Homo sapien

<400> SEQUENCE: 264

| | | | | | |
|---|---|---|---|---|---|
| aaagacgtta | aaccactcta | ctaccacttg | tggaactctc | aaagggtaaa | tgacaaascc | 60 |
| aatgaatgac | tctaaaaaca | atatttacat | ttaatggttt | gtagacaata | aaaaaacaag | 120 |
| gtggatagat | ctagaattgt | aacatttttaa | gaaaaccata | scatttgaca | gatgagaaag | 180 |
| ctcaattata | gatgcaaagt | tataactaaa | ctactatagt | agtaaagaaa | tacatttcac | 240 |
| acccttcata | taaattcact | atcttggctt | gaggcactcc | ataaaatgta | tcacgtgcat | 300 |
| a | | | | | | 301 |

<210> SEQ ID NO 265
<211> LENGTH: 301
<212> TYPE: DNA
<213> ORGANISM: Homo sapien

<400> SEQUENCE: 265

| | | | | | |
|---|---|---|---|---|---|
| tgcccaagtt | atgtgtaagt | gtatccgcac | ccagaggtaa | aactacactg | tcatctttgt | 60 |
| cttcttgtga | cgcagtattt | cttctctggg | gagaagccgg | gaagtcttct | cctggctcta | 120 |
| catattcttg | gaagtctcta | atcaactttt | gttccatttg | tttcatttct | tcaggaggga | 180 |

-continued

| | |
|---|---|
| ttttcagttt gtcaacatgt tctctaacaa cacttgccca tttctgtaaa gaatccaaag | 240 |
| cagtccaagg ctttgacatg tcaacaacca gcataactag agtatccttc agagatacgg | 300 |
| c | 301 |

<210> SEQ ID NO 266
<211> LENGTH: 301
<212> TYPE: DNA
<213> ORGANISM: Homo sapien

<400> SEQUENCE: 266

| | |
|---|---|
| taccgtctgc ccttcctccc atccaggcca tctgcgaatc tacatgggtc ctcctattcg | 60 |
| acaccagatc actcttttcct ctacccacag gcttgctatg agcaagagac acaacctcct | 120 |
| ctcttctgtg ttccagcttc ttttcctgtt cttcccaccc cttaagttct attcctgggg | 180 |
| atagagacac caatacccat aacctctctc ctaagcctcc ttataaccca gggtgcacag | 240 |
| cacagactcc tgacaactgg taaggccaat gaactgggag ctcacagctg ctgtgcctg | 300 |
| a | 301 |

<210> SEQ ID NO 267
<211> LENGTH: 301
<212> TYPE: DNA
<213> ORGANISM: Homo sapien

<400> SEQUENCE: 267

| | |
|---|---|
| aaagagcaca ggccagctca gcctgccctg gccatctaga ctcagcctgg ctccatgggg | 60 |
| gttctcagtg ctgagtccat ccaggaaaag ctcacctaga ccttctgagg ctgaatcttc | 120 |
| atcctcacag gcagcttctg agagcctgat attcctagcc ttgatggtct ggagtaaagc | 180 |
| ctcattctga ttcctctcct tcttttcttt caagttggct ttcctcacat ccctctgttc | 240 |
| aattcgcttc agcttgtctg ctttagccct catttccaga agcttcttct ctttggcatc | 300 |
| t | 301 |

<210> SEQ ID NO 268
<211> LENGTH: 301
<212> TYPE: DNA
<213> ORGANISM: Homo sapien

<400> SEQUENCE: 268

| | |
|---|---|
| aatgtctcac tcaactactt cccagcctac cgtggcctaa ttctgggagt tttcttctta | 60 |
| gatcttggga gagctggttc ttctaaggag aaggaggaag gacagatgta actttggatc | 120 |
| tcgaagagga agtctaatgg aagtaattag tcaacggtcc ttgtttagac tcttggaata | 180 |
| tgctgggtgg ctcagtgagc ccttttggag aaagcaagta ttattcttaa ggagtaacca | 240 |
| cttcccattg ttctactttc taccatcatc aattgtatat tatgtattct ttggagaact | 300 |
| a | 301 |

<210> SEQ ID NO 269
<211> LENGTH: 301
<212> TYPE: DNA
<213> ORGANISM: Homo sapien

<400> SEQUENCE: 269

| | |
|---|---|
| taacaatata cactagctat cttttttaact gtccatcatt agcaccaatg aagattcaat | 60 |
| aaaattaccct ttattcacac atctcaaaac aattctgcaa attcttagtg aagtttaact | 120 |
| atagtcacag accttaaata ttcacattgt tttctatgtc tactgaaaat aagttcacta | 180 |

```
cttttctgga tattctttac aaaatcttat taaaattcct ggtattatca cccccaatta    240
tacagtagca caaccacctt atgtagtttt tacatgatag ctctgtagaa gtttcacatc    300
t                                                                    301

<210> SEQ ID NO 270
<211> LENGTH: 301
<212> TYPE: DNA
<213> ORGANISM: Homo sapien

<400> SEQUENCE: 270
cattgaagag cttttgcgaa acatcagaac acaagtgctt ataaaattaa ttaagcctta     60
cacaagaata catattcctt ttatttctaa ggagttaaac atagatgtag ctgatgtgga    120
gagcttgctg gtgcagtgca tattggataa cactattcat ggccgaattg atcaagtcaa    180
ccaactcctt gaactggatc atcagaagaa gggtggtgca cgatatactg cactagataa    240
tggaccaacc aactaaattc tctcaccagg ctgtatcagt aaactggctt aacagaaaac    300
a                                                                    301

<210> SEQ ID NO 271
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 271
aaaaggttct cataagatta acaatttaaa taaatatttg atagaacatt ctttctcatt     60
tttatagctc atctttaggg ttgatattca gttcatgctt cccttgctgt tcttgatcca    120
gaattgcaat cacttcatca gcctgtattc gctccaattc tctataaagt gggtccaagg    180
tgaaccacag agccacagca cacctctttc ccttggtgac tgccttcacc ccatganggt    240
tctctcctcc agatganaac tgatcatgcg cccacatttt gggttttata gaagcagtca    300
c                                                                    301

<210> SEQ ID NO 272
<211> LENGTH: 301
<212> TYPE: DNA
<213> ORGANISM: Homo sapien

<400> SEQUENCE: 272
taaattgcta agccacagat aacaccaatc aaatggaaca atcactgtc ttcaaatgtc      60 ttatcagaaa accaaatgag cctggaatct tcataatacc taaacatgcc gtatttagga   120
tccaataatt ccctcatgat gagcaagaaa aattctttgc gcacccctcc tgcatccaca   180
gcatcttctc caacaaatat aaccttgagt ggcttcttgt aatctatgtt ctttgttttc   240
ctaaggactt ccattgcatc tcctacaata ttttctctac gcaccactag aattaagcag   300
g                                                                    301

<210> SEQ ID NO 273
<211> LENGTH: 301
<212> TYPE: DNA
<213> ORGANISM: Homo sapien
<220> FEATURE:
<221> NAME/KEY: misc_feature
<222> LOCATION: (1)...(301)
```

<223> OTHER INFORMATION: n = A,T,C or G

<400> SEQUENCE: 273

| acatgtgtgt atgtgtatct ttgggaaaan aanaagacat cttgtttayt attttttgg | 60 |
| agagangctg ggacatggat aatcacwtaa tttgctayta tyactttaat ctgactygaa | 120 |
| gaaccgtcta aaaataaaat ttaccatgtc dtatattcct tatagtatgc ttatttcacc | 180 |
| ttytttctgt ccagagagag tatcagtgac ananatttma gggtgaamac atgmattggt | 240 |
| gggacttnty tttacngagm accctgcccg sgcgccctcg makcngantt ccgcsananc | 300 |
| t | 301 |

<210> SEQ ID NO 274
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 274

| cttatatact ctttctcaga ggcaaaagag gagatgggta atgtagacaa ttctttgagg | 60 |
| aacagtaaat gattattaga gagaangaat ggaccaagga gacagaaatt aacttgtaaa | 120 |
| tgattctctt tggaatctga atgagatcaa gaggccagct ttagcttgtg gaaaagtcca | 180 |
| tctaggtatg gttgcattct cgtcttcttt tctgcagtag ataatgaggt aaccgaaggc | 240 |
| aattgtgctt cttttgataa gaagctttct tggtcatatc aggaaattcc aganaaagtc | 300 |
| c | 301 |

<210> SEQ ID NO 275
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 275

| tcggtgtcag cagcacgtgg cattgaacat tgcaatgtgg agcccaaacc acagaaaatg | 60 |
| gggtgaaatt ggccaacttt ctattaactt atgttggcaa ttttgccacc aacagtaagc | 120 |
| tggcccttct aataaaagaa aattgaaagg tttctcacta aacggaatta agtagtggag | 180 |
| tcaagagact cccaggcctc agcgtacctg cccgggcggc cgctcgaagc cgaattctgc | 240 |
| agatatccat cacactggcg gncgctcgan catgcatcta gaaggnccaa ttcgccctat | 300 |
| a | 301 |

<210> SEQ ID NO 276
<211> LENGTH: 301
<212> TYPE: DNA
<213> ORGANISM: Homo sapien

<400> SEQUENCE: 276

| tgtacacata ctcaataaat aaatgactgc attgtggtat tattactata ctgattatat | 60 |
| ttatcatgtg acttctaatt agaaaatgta tccaaaagca aaacagcaga tatacaaaat | 120 |
| taaagagaca gaagatagac attaacagat aaggcaactt atacattgag aatccaaatc | 180 |
| caatacattt aaacatttgg gaatgagggg ggacaaatgg aagccagatc aaatttgtgt | 240 |

```
aaaactattc agtatgtttc ccttgcttca tgtctgagaa ggctctcctt caatggggat     300
g                                                                    301
```

<210> SEQ ID NO 277
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 277

```
tttgttgatg tcagtatttt attacttgcg ttatgagtgc tcacctggga aattctaaag      60
atacagagga cttggaggaa gcagagcaac tgaatttaat ttaaaagaag gaaaacattg     120
gaatcatggc actcctgata cttccccaaa tcaacactct caatgcccca ccctcgtcct     180
caccatagtg gggagactaa agtggccacg gatttgcctt angtgtgcag tgcgttctga     240
gttcnctgtc gattacatct gaccagtctc cttttttccga agtccntccg ttcaatcttg     300
c                                                                    301
```

<210> SEQ ID NO 278
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 278

```
taccactaca ctccagcctg ggcaacagag caagacctgt ctcaaagcat aaaatggaat      60
aacatatcaa atgaaacagg gaaatgaag ctgacaattt atggaagcca gggcttgtca     120
cagtctctac tgttattatg cattacctgg gaatttatat aagcccttaa taataatgcc     180
aatgaacatc tcatgtgtgc tcacaatgtt ctggcactat tataagtgct tcacaggttt     240
tatgtgttct tcgtaacttt atggantagg tactcggccg cgaacacgct aagccgaatt     300
c                                                                    301
```

<210> SEQ ID NO 279
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 279

```
aaagcaggaa tgacaaagct tgcttttctg gtatgttcta ggtgtattgt gacttttact      60
gttatattaa ttgccaatat aagtaaatat agattatata tgtatagtgt ttcacaaagc     120
ttagaccttt accttccagc cacccacag tgcttgatat ttcagagtca gtcattggtt     180
atacatgtgt agtccaaag cacataagct agaanaanaa atatttctag ggagcactac     240
catctgtttt cacatgaaat gccacacaca tagaactcca acatcaattt cattgcacag     300
a                                                                    301
```

<210> SEQ ID NO 280

<211> LENGTH: 301
<212> TYPE: DNA
<213> ORGANISM: Homo sapien

<400> SEQUENCE: 280

```
ggtactggag ttttcctccc ctgtgaaaac gtaactactg ttgggagtga attgaggatg      60
tagaaaggtg gtggaaccaa attgtggtca atggaaatag gagaatatgg ttctcactct     120
tgagaaaaaa acctaagatt agcccaggta gttgcctgta acttcagttt ttctgcctgg     180
gtttgatata gtttagggtt ggggttagat taagatctaa attacatcag gacaaagaga     240
cagactatta actccacagt taattaagga ggtatgttcc atgtttattt gttaaagcag     300
t                                                                    301
```

<210> SEQ ID NO 281
<211> LENGTH: 301
<212> TYPE: DNA
<213> ORGANISM: Homo sapien

<400> SEQUENCE: 281

```
aggtacaaga aggggaatgg gaaagagctg ctgctgtggc attgttcaac ttggatattc      60
gccgagcaat ccaaatcctg aatgaagggg catcttctga aaaggagat ctgaatctca     120
atgtggtagc aatggcttta tcgggttata cggatgagaa gaactccctt tggagagaaa     180
tgtgtagcac actgcgatta cagctaaata acccgtattt gtgtgtcatg tttgcatttc     240
tgacaagtga aacaggatct tacgatggag ttttgtatga aaacaaagtt gcagtacctc     300
g                                                                    301
```

<210> SEQ ID NO 282
<211> LENGTH: 301
<212> TYPE: DNA
<213> ORGANISM: Homo sapien

<400> SEQUENCE: 282

```
caggtactac agaattaaaa tactgacaag caagtagttt cttggcgtgc acgaattgca      60
tccagaaccc aaaaattaag aaattcaaaa agacattttg tgggcacctg ctagcacaga     120
agcgcagaag caaagcccag gcagaaccat gctaacctta cagctcagcc tgcacagaag     180
cgcagaagca agcccaggc agaaccatgc taaccttaca gctcagcctg cacagaagcg     240
cagaagcaaa gcccaggcag aacatgctaa ccttacagct cagcctgcac agaagcacag     300
a                                                                    301
```

<210> SEQ ID NO 283
<211> LENGTH: 301
<212> TYPE: DNA
<213> ORGANISM: Homo sapien

<400> SEQUENCE: 283

```
atctgtatac ggcagacaaa ctttatarag tgtagagagg tgagcgaaag gatgcaaaag      60
cactttgagg gctttataat aatatgctgc ttgaaaaaaa aaatgtgtag ttgatactca     120
gtgcatctcc agacatagta aggggttgct ctgaccaatc aggtgatcat tttttctatc     180
acttcccagg ttttatgcaa aaattttgtt aaattctata atggtgatat gcatctttta     240
ggaaacatat acatttttaa aaatctattt tatgtaagaa ctgacagacg aatttgcttt     300
g                                                                    301
```

<210> SEQ ID NO 284
<211> LENGTH: 301
<212> TYPE: DNA
<213> ORGANISM: Homo sapien

<400> SEQUENCE: 284

| caggtacaaa acgctattaa gtggcttaga atttgaacat ttgtggtctt tatttacttt | 60 |
| gcttcgtgtg tgggcaaagc aacatcttcc ctaaatatat attaccaaga aaagcaagaa | 120 |
| gcagattagg ttttgacaa acaaacagg ccaaaggggg ctgacctgg agcagagcat | 180 |
| ggtgagaggc aaggcatgag agggcaagtt tgttgtggac agatctgtgc ctactttatt | 240 |
| actggagtaa aagaaaacaa agttcattga tgtcgaagga tatatacagt gttagaaatt | 300 |
| a | 301 |

<210> SEQ ID NO 285
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 285

| acatcaccat gatcggatcc cccacccatt atacgttgta tgtttacata aatactcttc | 60 |
| aatgatcatt agtgttttaa aaaaaatact gaaaactcct tctgcatccc aatctctaac | 120 |
| caggaaagca aatgctattt acagacctgc aagcccctccc tcaaacnaaa ctatttctgg | 180 |
| attaaatatg tctgacttct tttgaggtca cacgactagg caaatgctat ttacgatctg | 240 |
| caaaagctgt ttgaagagtc aaagccccca tgtgaacacg atttctggac cctgtaacag | 300 |
| t | 301 |

<210> SEQ ID NO 286
<211> LENGTH: 301
<212> TYPE: DNA
<213> ORGANISM: Homo sapien

<400> SEQUENCE: 286

| taccactgca ttccagcctg ggtgacagag tgagactccg tctccaaaaa aaactttgct | 60 |
| tgtatattat ttttgcctta cagtggatca ttctagtagg aaaggacagt aagattttt | 120 |
| atcaaaatgt gtcatgccag taagagatgt tatattcttt tctcatttct tccccaccca | 180 |
| aaaataagct accatatagc ttataagtct caaattttg cctttactaa aaatgtgatt | 240 |
| gtttctgttc attgtgtatg cttcatcacc tatattaggc aaattccatt ttttcccttg | 300 |
| t | 301 |

<210> SEQ ID NO 287
<211> LENGTH: 301
<212> TYPE: DNA
<213> ORGANISM: Homo sapien

<400> SEQUENCE: 287

| tacagatctg ggaactaaat attaaaaatg agtgtggctg gatatatgga gaatgttggg | 60 |
| cccagaagga acgtagagat cagatattac aacagctttg ttttgagggt tagaaatatg | 120 |
| aaatgatttg gttatgaacg cacagtttag gcagcagggc cagaatcctg accctctgcc | 180 |
| ccgtggttat ctcctcccca gcttggctgc ctcatgttat cacagtattc cattttgttt | 240 |

```
gttgcatgtc ttgtgaagcc atcaagattt tctcgtctgt tttcctctca ttggtaatgc      300
t                                                                     301
```

<210> SEQ ID NO 288
<211> LENGTH: 301
<212> TYPE: DNA
<213> ORGANISM: Homo sapien

<400> SEQUENCE: 288

```
gtacacctaa ctgcaaggac agctgaggaa tgtaatgggc agccgctttt aaagaagtag      60
agtcaatagg aagacaaatt ccagttccag ctcagtctgg gtatctgcaa agctgcaaaa     120
gatctttaaa gacaatttca agagaatatt tccttaaagt tggcaatttg agatcatac      180
aaaagcatct gcttttgtga tttaatttag ctcatctggc cactggaaga atccaaacag     240
tctgccttaa ttttggatga atgcatgatg gaaattcaat aatttagaaa gttaaaaaaa     300
a                                                                     301
```

<210> SEQ ID NO 289
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 289

```
ggtacactgt ttccatgtta tgtttctaca cattgctacc tcagtgctcc tggaaactta      60
gcttttgatg tctccaagta gtccaccttc atttaactct ttgaaactgt atcatctttg     120
ccaagtaaga gtggtggcct atttcagctg ctttgacaaa atgactggct cctgacttaa     180
cgttctataa atgaatgtgc tgaagcaaag tgcccatggt ggcggcgaan aagagaaaga     240
tgtgttttgt tttggactct ctgtggtccc ttccaatgct gtgggtttcc aaccagngga     300
a                                                                     301
```

<210> SEQ ID NO 290
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 290

```
acactgagct cttcttgata aatatacaga atgcttggca tatacaagat tctatactac      60
tgactgatct gttcatttct ctcacagctc ttaccccaa aagcttttcc accctaagtg      120
ttctgacctc cttttctaat cacagtaggg atagaggcag anccacctac aatgaacatg     180
gagttctatc aagaggcaga aacagcacag aatcccagtt ttaccattcg ctagcagtgc     240
tgccttgaac aaaaacattt ctccatgtct cattttcttc atgcctcaag taacagtgag     300
a                                                                     301
```

<210> SEQ ID NO 291
<211> LENGTH: 301
<212> TYPE: DNA
<213> ORGANISM: Homo sapien

<400> SEQUENCE: 291

```
caggtaccaa tttcttctat cctagaaaca tttcatttta tgttgttgaa acataacaac      60
tatatcagct agattttttt tctatgcttt acctgctatg gaaaatttga cacattctgc     120
tttactcttt tgtttatagg tgaatcacaa aatgtatttt tatgtattct gtagttcaat     180
agccatggct gtttacttca tttaatttat ttagcataaa gacattatga aaaggcctaa     240
acatgagctt cacttcccca ctaactaatt agcatctgtt atttcttaac cgtaatgcct     300
a                                                                    301
```

<210> SEQ ID NO 292
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 292

```
acctttagt agtaatgtct aataataaat aagaaatcaa ttttataagg tccatatagc      60
tgtattaaat aattttaag tttaaaagat aaataccat cattttaaat gttggtattc       120
aaaaccaaag natataaccg aaaggaaaaa cagatgagac ataaaatgat ttgcnagatg     180
ggaaatatag tasttyatga atgttnatta aattccagtt ataatagtgg ctacacactc     240
tcactacaca cacagaccc acagtcctat atgccacaaa cacatttcca taacttgaaa     300
a                                                                    301
```

<210> SEQ ID NO 293
<211> LENGTH: 301
<212> TYPE: DNA
<213> ORGANISM: Homo sapien

<400> SEQUENCE: 293

```
ggtaccaagt gctggtgcca gcctgttacc tgttctcact gaaaagtctg gctaatgctc      60
ttgtgtagtc acttctgatt ctgacaatca atcaatcaat ggcctagagc actgactgtt     120
aacacaaacg tcactagcaa agtagcaaca gctttaagtc taaatacaaa gctgttctgt     180
gtgagaattt tttaaaaggc tacttgtata ataacccttg tcattttaa tgtacctcgg      240 ccgcgaccac gctaagccga attctgcaga tatccatcac actggcggcc gctcgagcat     300
g                                                                    301
```

<210> SEQ ID NO 294
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 294

```
tgacccataa caatatacac tagctatctt tttaactgtc catcattagc accaatgaag      60
attcaataaa attaccttta ttcacacatc tcaaaacaat tctgcaaatt cttagtgaag     120
tttaactata gtcacaganc ttaaatattc acattgtttt ctatgtctac tgaaaataag     180
ttcactactt ttctgggata ttctttacaa aatcttatta aaattcctgg tattatcacc     240
cccaattata cagtagcaca accaccttat gtagttttta catgatagct ctgtagaggt     300
```

```
t                                                                          301

<210> SEQ ID NO 295
<211> LENGTH: 305
<212> TYPE: DNA
<213> ORGANISM: Homo sapien

<400> SEQUENCE: 295
gtactctttc tctcccctcc tctgaattta attctttcaa cttgcaattt gcaaggatta      60
cacatttcac tgtgatgtat attgtgttgc aaaaaaaaaa gtgtctttgt ttaaaattac     120
ttggtttgtg aatccatctt gcttttccc cattggaact agtcattaac ccatctctga     180
actggtagaa aaacrtctga agagctagtc tatcagcatc tgacaggtga attggatggt     240
tctcagaacc atttcaccca gacagcctgt ttctatcctg tttaataaat tagttttgggt    300 tctct                                                                305

<210> SEQ ID NO 296
<211> LENGTH: 301
<212> TYPE: DNA
<213> ORGANISM: Homo sapien

<400> SEQUENCE: 296
aggtactatg ggaagctgct aaataatat ttgatagtaa aagtatgtaa tgtgctatct      60
cacctagtag taaactaaaa ataaactgaa actttatgga atctgaagtt attttccttg    120
attaaataga attaataaac caatatgagg aaacatgaaa ccatgcaatc tactatcaac    180
tttgaaaaag tgattgaacg aaccacttag ctttcagatg atgaacactg ataagtcatt    240
tgtcattact ataaatttta aaatctgtta ataagatggc ctatagggag gaaaaagggg    300
c                                                                   301

<210> SEQ ID NO 297
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 297
actgagtttt aactggacgc caagcaggca aggctggaag gttttgctct ctttgtgcta      60
aaggttttga aaaccttgaa ggagaatcat tttgacaaga agtacttaag agtctagaga    120
acaaagangt gaaccagctg aaagctctcg ggggaancttt acatgtgttg ttaggcctgt    180
tccatcattg ggagtgcact ggccatccct caaaatttgt ctgggctggc ctgagtggtc    240
accgcacctc ggccgcgacc acgctaagcc gaattctgca gatatccatc acactggcgg    300

<210> SEQ ID NO 298
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 298
tatggggttt gtcacccaaa agctgatgct gagaaaggcc tccctggggc ccctcccgcg      60
ggcatctgag agacctggtg ttccagtgtt tctggaaatg ggtcccagtg ccgccggctg    120
```

```
tgaagctctc agatcaatca cgggaagggc ctggcggtgg tggccacctg gaaccaccct    180
gtcctgtctg tttacatttc actaycaggt tttctctggg cattacnatt tgttccccta    240
caacagtgac ctgtgcattc tgctgtggcc tgctgtgtct gcaggtggct ctcagcgagg    300
t                                                                   301

<210> SEQ ID NO 299
<211> LENGTH: 301
<212> TYPE: DNA
<213> ORGANISM: Homo sapien

<400> SEQUENCE: 299
gttttgagac ggagtttcac tcttgttgcc cagactggac tgcaatggca gggtctctgc     60
tcactgcacc ctctgcctcc caggttcgag caattctcct gcctcagcct cccaggtagc    120
tgggattgca ggctcacgcc accataccca gctaattttt ttgtattttt agtagagacg    180
gagtttcgcc atgttggcca gctggtctca aactcctgac ctcaagcgac ctgcctgcct    240
cggcctccca agtgctggaa ttataggca tgagtcaaca cgcccagcct aaagatattt    300
t                                                                   301

<210> SEQ ID NO 300
<211> LENGTH: 301
<212> TYPE: DNA
<213> ORGANISM: Homo sapien

<400> SEQUENCE: 300
attcagtttt atttgctgcc ccagtatctg taaccaggag tgccacaaaa tcttgccaga     60
tatgtcccac acccactggg aaaggctccc acctggctac ttcctctatc agctgggtca    120
gctgcattcc acaaggttct cagcctaatg agtttcacta cctgccagtc tcaaaactta    180
gtaaagcaag accatgacat tcccccacgg aaatcagagt ttgccccacc gtcttgttac    240
tataaagcct gcctctaaca gtccttgctt cttcacacca atcccgagcg catcccccat    300
g                                                                   301

<210> SEQ ID NO 301
<211> LENGTH: 301
<212> TYPE: DNA
<213> ORGANISM: Homo sapien

<400> SEQUENCE: 301
ttaaattttt gagaggataa aaaggacaaa taatctagaa atgtgtcttc ttcagtctgc     60
agaggacccc aggtctccaa gcaaccacat ggtcaagggc atgaataatt aaaagttggt    120
gggaactcac aaagaccctc agagctgaga cacccacaac agtgggagct cacaaagacc    180
ctcagagctg agacacccac aacagtggga gctcacaaag accctcagag ctgagacacc    240
cacaacagca cctcgttcag ctgccacatg tgtgaataag gatgcaatgt ccagaagtgt    300
t                                                                   301

<210> SEQ ID NO 302
<211> LENGTH: 301
<212> TYPE: DNA
<213> ORGANISM: Homo sapien

<400> SEQUENCE: 302
aggtacacat ttagcttgtg gtaaatgact cacaaaactg attttaaaat caagttaatg     60
```

-continued

```
tgaattttga aaattactac ttaatcctaa ttcacaataa caatggcatt aaggtttgac    120
ttgagttggt tcttagtatt atttatggta aataggctct taccacttgc aaataactgg    180
ccacatcatt aatgactgac ttcccagtaa ggctctctaa ggggtaagta ggaggatcca    240
caggatttga gatgctaagg ccccagagat cgtttgatcc aaccctctta ttttcagagg    300
g                                                                    301
```

<210> SEQ ID NO 303
<211> LENGTH: 301
<212> TYPE: DNA
<213> ORGANISM: Homo sapien

<400> SEQUENCE: 303

```
aggtaccaac tgtggaaata ggtagaggat catttttct ttccatatca actaagttgt     60
atattgtttt ttgacagttt aacacatctt cttctgtcag agattctttc acaatagcac    120
tggctaatgg aactaccgct tgcatgttaa aaatggtggt ttgtgaaatg atcataggcc    180
agtaacgggt atgttttct aactgatctt tgctcgttc caagggacc tcaagacttc       240 catcgatttt atatctgggg tctagaaaag gagttaatct gttttccctc ataaattcac    300
c                                                                    301
```

<210> SEQ ID NO 304
<211> LENGTH: 301
<212> TYPE: DNA
<213> ORGANISM: Homo sapien

<400> SEQUENCE: 304

```
acatggatgt tattttgcag actgtcaacc tgaatttgta tttgcttgac attgcctaat    60
tattagtttc agtttcagct tacccacttt ttgtctgcaa catgcaraas agacagtgcc    120 cttttagtg tatcatatca ggaatcatct cacattggtt tgtgccatta ctggtgcagt    180
gactttcagc cacttgggta aggtggagtt ggccatatgt ctccactgca aaattactga    240
ttttcctttt gtaattaata agtgtgtgtg tgaagattct ttgagatgag gtatatatct    300
c                                                                    301
```

<210> SEQ ID NO 305
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 305

```
gangtacagc gtggtcaagg taacaagaag aaaaaaatgt gagtggcatc ctgggatgag    60 caggggaca gacctggaca gacacgttgt catttgctgc tgtgggtagg aaaatgggcg     120
taaaggagga gaaacagata caaaatctcc aactcagtat taaggtattc tcatgcctag    180
aatattggta gaaacaagaa tacattcata tgcaaataa ctaaccatgg tggaacaaaa     240
ttctgggatt taagttggat accaangaaa ttgtattaaa agagctgttc atggaataag    300
a                                                                    301
```

<210> SEQ ID NO 306
<211> LENGTH: 8
<212> TYPE: PRT
<213> ORGANISM: Homo sapien

<400> SEQUENCE: 306

Val Leu Gly Trp Val Ala Glu Leu
 1               5

<210> SEQ ID NO 307
<211> LENGTH: 637
<212> TYPE: DNA
<213> ORGANISM: Homo sapien

<400> SEQUENCE: 307

| acagggratg aagggaaagg gagaggatga ggaagccccc ctggggattt ggtttggtcc | 60 |
| ttgtgatcag gtggtctatg gggcttatcc ctacaaagaa gaatccagaa ataggggcac | 120 |
| attgaggaat gatacttgag cccaaagagc attcaatcat tgttttattt gccttmtttt | 180 |
| cacaccattg gtgagggagg gattaccacc ctggggttat gaagatggtt gaacacccca | 240 |
| cacatagcac cggagatatg agatcaacag tttcttagcc atagagattc acagcccaga | 300 |
| gcaggaggac gcttgcacac catgcaggat gacatggggg atgcgctcgg gattggtgtg | 360 |
| aagaagcaag gactgttaga ggcaggcttt atagtaacaa gacggtgggg caaactctga | 420 |
| tttccgtggg ggaatgtcat ggtcttgctt tactaagttt tgagactggc aggtagtgaa | 480 |
| actcattagg ctgagaacct tgtggaatgc acttgaccca sctgatagag gaagtagcca | 540 |
| ggtgggagcc tttcccagtg ggtgtgggac atatctggca agattttgtg gcactcctgg | 600 |
| ttacagatac tggggcagca aataaaactg aatcttg | 637 |

<210> SEQ ID NO 308
<211> LENGTH: 647
<212> TYPE: DNA
<213> ORGANISM: Homo sapien
<220> FEATURE:
<221> NAME/KEY: misc_feature
<222> LOCATION: (1)...(647)
<223> OTHER INFORMATION: n = A,T,C or G

<400> SEQUENCE: 308

| acgattttca ttatcatgta aatcgggtca ctcaaggggc caaccacagc tgggagccac | 60 |
| tgctcagggg aaggttcata tgggactttc tactgcccaa ggttctatac aggatataaa | 120 |
| ggngcctcac agtatagatc tggtagcaaa gaagaagaaa caaacactga tctctttctg | 180 |
| ccaccoctct gacccttttgg aactcctctg acccttttaga acaagcctac ctaatatctg | 240 |
| ctagagaaaa gaccaacaac ggcctcaaag gatctcttac catgaaggtc tcagctaatt | 300 |
| cttggctaag atgtgggttc cacattaggt tctgaatatg gggggaaggg tcaatttgct | 360 |
| cattttgtgt gtggataaag tcaggatgcc caggggccag agcaggggc tgcttgcttt | 420 |
| gggaacaatg gctgagcata taaccatagg ttatggggaa caaaacaaca tcaaagtcac | 480 |
| tgtatcaatt gccatgaaga cttgagggac ctgaatctac cgattcatct taaggcagca | 540 |
| ggaccagttt gagtggcaac aatgcagcag cagaatcaat ggaaacaaca gaatgattgc | 600 |
| aatgtccttt tttttctcct gcttctgact tgataaaagg ggaccgt | 647 |

<210> SEQ ID NO 309
<211> LENGTH: 460
<212> TYPE: DNA
<213> ORGANISM: Homo sapien

<400> SEQUENCE: 309

| actttatagt ttaggctgga cattggaaaa aaaaaaaagc cagaacaaca tgtgatagat | 60 |

```
aatatgattg gctgcacact tccagactga tgaatgatga acgtgatgga ctattgtatg      120
gagcacatct tcagcaagag ggggaaatac tcatcatttt tggccagcag ttgtttgatc      180
accaaacatc atgccagaat actcagcaaa ccttcttagc tcttgagaag tcaaagtccg      240
ggggaattta ttcctggcaa ttttaattgg actccttatg tgagagcagc ggctacccag      300
ctggggtggt ggagcgaacc cgtcactagt ggacatgcag tggcagagct cctggtaacc      360
acctagagga atacacaggc acatgtgtga tgccaagcgt gacacctgta gcactcaaat      420
ttgtcttgtt tttgtctttc ggtgtgtaag attcttaagt                            460

<210> SEQ ID NO 310
<211> LENGTH: 539
<212> TYPE: DNA
<213> ORGANISM: Homo sapien

<400> SEQUENCE: 310
acgggactta tcaaataaag ataggaaaag aagaaaactc aaatattata ggcagaaatg       60
ctaaaggttt taaaatatgt caggattgga agaaggcatg gataaagaac aaagttcagt      120
taggaaagag aaacacagaa ggaagagaca caataaaagt cattatgtat tctgtgagaa      180
gtcagacagt aagatttgtg ggaaatgggt tggtttgttg tatggtatgt attttagcaa      240
taatctttat ggcagagaaa gctaaaatcc tttagcttgc gtgaatgatc acttgctgaa      300
ttcctcaagg taggcatgat gaaggagggt ttagaggaga cacagacaca atgaactgac      360
ctagatagaa agccttagta tactcagcta ggaatagtga ttctgagggc acactgtgac      420
atgattatgt cattacatgt atggtagtga tggggatgat aggaaggaag aacttatggc      480
atattttcac ccccacaaaa gtcagttaaa tattgggaca ctaaccatcc aggtcaaga      539

<210> SEQ ID NO 311
<211> LENGTH: 526
<212> TYPE: DNA
<213> ORGANISM: Homo sapien
<220> FEATURE:
<221> NAME/KEY: misc_feature
<222> LOCATION: (1)...(526)
<223> OTHER INFORMATION: n = A,T,C or G

<400> SEQUENCE: 311
caaatttgag ccaatgacat agaattttac aaatcaagaa gcttattctg gggccatttc       60
ttttgacgtt ttctctaaac tactaaagag gcattaatga tccataaatt atattatcta      120
catttacagc atttaaaatg tgttcagcat gaaatattag ctacagggga agctaaataa      180
attaaacatg gaataaagat ttgtccttaa atataatcta caagaagact ttgatatttg      240
tttttcacaa gtgaagcatt cttataaagt gtcataacct ttttggggaa actatgggaa      300
aaaatgggga aactctgaag ggttttaagt atcttacctg aagctacaga ctccataacc      360
tctctttaca gggagctcct gcagcccta cagaaatgag tggctgagat tcttgattgc      420
acagcaagag cttctcatct aaacccttc cctttttagt atctgtgtat caagtataaa      480
agttctataa actgtagtnt acttatttta atccccaaag cacagt                    526

<210> SEQ ID NO 312
<211> LENGTH: 500
<212> TYPE: DNA
<213> ORGANISM: Homo sapien
<220> FEATURE:
<221> NAME/KEY: misc_feature
<222> LOCATION: (1)...(500)
```

<223> OTHER INFORMATION: n = A,T,C or G

<400> SEQUENCE: 312

```
cctctctctc cccaccccct gactctagag aactgggttt tctcccagta ctccagcaat     60
tcatttctga aagcagttga gccactttat tccaaagtac actgcagatg ttcaaactct    120
ccatttctct ttccttcca cctgccagtt ttgctgactc tcaacttgtc atgagtgtaa    180
gcattaagga cattatgctt cttcgattct gaagacaggc cctgctcatg gatgactctg    240
gcttcttagg aaaatatttt tcttccaaaa tcagtaggaa atctaaactt atccctctt    300
tgcagatgtc tagcagcttc agacatttgg ttaagaaccc atgggaaaaa aaaaaatcct    360
tgctaatgtg gtttcctttg taaaccanga ttcttatttg nctggtatag aatatcagct    420
ctgaacgtgt ggtaaagatt tttgtgtttg aatataggag aaatcagttt gctgaaaagt    480
tagtcttaat tatctattgg                                                500
```

<210> SEQ ID NO 313
<211> LENGTH: 718
<212> TYPE: DNA
<213> ORGANISM: Homo sapien
<220> FEATURE:
<221> NAME/KEY: misc_feature
<222> LOCATION: (1)...(718)
<223> OTHER INFORMATION: n = A,T,C or G

<400> SEQUENCE: 313

```
ggagatttgt gtggtttgca gccgagggag accaggaaga tctgcatggt gggaaggacc     60
tgatgataca gaggtgagaa ataagaaagg ctgctgactt taccatctga ggccacacat    120
ctgctgaaat ggagataatt aacatcacta gaaacagcaa gatgacaata taatgtctaa    180
gtagtgacat gttttttgcac atttccagcc cttttaaata tccacacaca caggaagcac    240
aaaaggaagc acagagatcc ctgggagaaa tgcccggccg ccatcttggg tcatcgatga    300
gcctcgccct gtgcctgntc ccgcttgtga gggaaggaca ttagaaaatg aattgatgtg    360
ttccttaaag gatggcagga aaacagatcc tgttgtggat atttatttga acgggattac    420
agatttgaaa tgaagtcaca aagtgagcat taccaatgag aggaaaacag acgagaaaat    480
cttgatggtt cacaagacat gcaacaaaca aaatggaata ctgtgatgac acgagcagcc    540
aactggggag gagataccac ggggcagagg tcaggattct ggccctgctg cctaactgtg    600
cgttatacca atcatttcta tttctaccct caaacaagct gtngaatatc tgacttacgg    660
ttcttntggc ccacattttc atnatccacc ccntcntttt aannttantc caaantgt     718
```

<210> SEQ ID NO 314
<211> LENGTH: 358
<212> TYPE: DNA
<213> ORGANISM: Homo sapien

<400> SEQUENCE: 314

```
gtttatttac attacagaaa aaacatcaag acaatgtata ctatttcaaa tatatccata     60
cataatcaaa tatagctgta gtacatgttt tcattggtgt agattaccac aaatgcaagg    120
caacatgtgt agatctcttg tcttattctt ttgtctataa tactgtattg tgtagtccaa    180
gctctcggta gtccagccac tgtgaaacat gctccccttta gattaacctc gtggacgctc    240
ttgttgtatt gctgaactgt agtgccctgt attttgcttc tgtctgtgaa ttctgttgct    300
tctggggcat tccttgtga tgcagaggac caccacacag atgacagcaa tctgaatt      358
```

<210> SEQ ID NO 315
<211> LENGTH: 341
<212> TYPE: DNA
<213> ORGANISM: Homo sapien

<400> SEQUENCE: 315

| | | | | | |
|---|---|---|---|---|---|
| taccacctcc | ccgctggcac | tgatgagccg | catcaccatg | gtcaccagca | ccatgaaggc | 60 |
| ataggtgatg | atgaggacat | ggaatgggcc | cccaaggatg | gtctgtccaa | agaagcgagt | 120 |
| gacccccatt | ctgaagatgt | ctggaacctc | taccagcagg | atgatgatag | ccccaatgac | 180 |
| agtcaccagc | tccccgacca | gccggatatc | gtccttaggg | gtcatgtagg | cttcctgaag | 240 |
| tagcttctgc | tgtaagaggg | tgttgtcccg | ggggctcgtg | cggttattgg | tcctgggctt | 300 |
| gaggggcgg | tagatgcagc | acatggtgaa | gcagatgatg | t | | 341 |

<210> SEQ ID NO 316
<211> LENGTH: 151
<212> TYPE: DNA
<213> ORGANISM: Homo sapien

<400> SEQUENCE: 316

| | | | | | |
|---|---|---|---|---|---|
| agactgggca | agactcttac | gccccacact | gcaatttggt | cttgttgccg | tatccattta | 60 |
| tgtgggcctt | tctcgagttt | ctgattataa | acaccactgg | agcgatgtgt | tgactggact | 120 |
| cattcaggga | gctctggttg | caatattagt | t | | | 151 |

<210> SEQ ID NO 317
<211> LENGTH: 151
<212> TYPE: DNA
<213> ORGANISM: Homo sapien

<400> SEQUENCE: 317

| | | | | | |
|---|---|---|---|---|---|
| agaactagtg | gatcctaatg | aaatacctga | aacatatatt | ggcatttatc | aatggctcaa | 60 |
| atcttcattt | atctctggcc | ttaaccctgg | ctcctgaggc | tgcggccagc | agatcccagg | 120 |
| ccagggctct | gttcttgcca | cacctgcttg | a | | | 151 |

<210> SEQ ID NO 318
<211> LENGTH: 151
<212> TYPE: DNA
<213> ORGANISM: Homo sapien

<400> SEQUENCE: 318

| | | | | | |
|---|---|---|---|---|---|
| actggtggga | ggcgctgttt | agttggctgt | tttcagaggg | gtctttcgga | gggacctcct | 60 |
| gctgcaggct | ggagtgtctt | tattcctggc | gggagaccgc | acattccact | gctgaggctg | 120 |
| tgggggcggt | ttatcaggca | gtgataaaca | t | | | 151 |

<210> SEQ ID NO 319
<211> LENGTH: 151
<212> TYPE: DNA
<213> ORGANISM: Homo sapien

<400> SEQUENCE: 319

| | | | | | |
|---|---|---|---|---|---|
| aactagtgga | tccagagcta | taggtacagt | gtgatctcag | ctttgcaaac | acattttcta | 60 |
| catagatagt | actaggtatt | aatagatatg | taaagaaaga | aatcacacca | ttaataatgg | 120 |
| taagattggg | tttatgtgat | tttagtgggt | a | | | 151 |

<210> SEQ ID NO 320
<211> LENGTH: 150
<212> TYPE: DNA

<213> ORGANISM: Homo sapien

<400> SEQUENCE: 320

| aactagtgga tccactagtc cagtgtggtg gaattccatt gtgttggggt tctagatcgc | 60 |
| gagcggctgc cctttttttt tttttttttg gggggaatt tttttttttt aatagttatt | 120 |
| gagtgttcta cagcttacag taaataccat | 150 |

<210> SEQ ID NO 321
<211> LENGTH: 151
<212> TYPE: DNA
<213> ORGANISM: Homo sapien

<400> SEQUENCE: 321

| agcaactttg tttttcatcc aggttatttt aggcttagga tttcctctca cactgcagtt | 60 |
| tagggtggca ttgtaaccag ctatggcata ggtgttaacc aaaggctgag taaacatggg | 120 |
| tgcctctgag aaatcaaagt cttcatacac t | 151 |

<210> SEQ ID NO 322
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 322

| atccagcatc ttctcctgtt tcttgccttc cttttcttc ttcttasatt ctgcttgagg | 60 |
| tttgggcttg gtcagtttgc cacagggctt ggagatggtg acagtcttct ggcattcggc | 120 |
| attgtgcagg gctcgcttca nacttccagt t | 151 |

<210> SEQ ID NO 323
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 323

| tgaggacttg tkttctttt ctttatttt aatcctctta ckttgtaaat atattgccta | 60 |
| nagactcant tactacccag tttgtggttt twtgggagaa atgtaactgg acagttagct | 120 |
| gttcaatyaa aaagacactt ancccatgtg g | 151 |

<210> SEQ ID NO 324
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 324

| acctgtgtgg aatttcagct ttcctcatgc aaaaggattt tgtatcccg gcctacttga | 60 |
| agaagtggtc agctaaagga atccaggttg ttggttggac tgttaatacc tttgatgaaa | 120 |
| agagttacta cgaatcccat cttggttcca gctatatcac tgcacgcatg gtagaagact | 180 |
| gcgaacctca cttctagact ttcacggtgg gacgaaacgg gttcagaaac tgccaggggc | 240 |

```
ctcatacagg gatatcaaaa tacccttgt gctacccagg ccctgggaa tcaggtgact    300 cacacaaatg caatagttgg tcactgcatt tttacctgaa ccaaagctaa acccggtgtt    360
gccaccatgc accatggcat gccagagttc aacactgttg ctcttgaaaa ttgggtctga    420
aaaaacgcac aagagcccct gccctgccct agctgangca c                       461
```

<210> SEQ ID NO 325
<211> LENGTH: 400
<212> TYPE: DNA
<213> ORGANISM: Homo sapien

<400> SEQUENCE: 325

```
acactgtttc catgttatgt ttctacacat tgctacctca gtgctcctgg aaacttagct     60
tttgatgtct ccaagtagtc caccttcatt taactctttg aaactgtatc atctttgcca    120
agtaagagtg gtggcctatt tcagctgctt tgacaaaatg actggctcct gacttaacgt    180
tctataaatg aatgtgctga agcaaagtgc ccatggtggc ggcgaagaag agaaagatgt    240
gttttgtttt ggactctctg tggtcccttc caatgctgtg ggtttccaac caggggaagg    300 gtccctttg cattgccaag tgccataacc atgagcacta cgctaccatg gttctgcctc    360
ctggccaagc aggctggttt gcaagaatga aatgaatgat                         400
```

<210> SEQ ID NO 326
<211> LENGTH: 1215
<212> TYPE: DNA
<213> ORGANISM: Homo sapien

<400> SEQUENCE: 326

```
ggaggactgc agcccgcact cgcagccctg gcaggcggca ctggtcatgg aaaacgaatt     60
gttctgctcg ggcgtcctgg tgcatccgca gtgggtgctg tcagccgcac actgtttcca    120
gaactcctac accatcgggc tgggcctgca cagtcttgag gccgaccaag agccagggag    180
ccagatggtg gaggccagcc tctccgtacg gcacccagag tacaacagac ccttgctcgc    240
taacgacctc atgctcatca gttggacga atccgtgtcc gagtctgaca ccatccggag    300
catcagcatt gcttcgcagt gccctaccgc ggggaactct tgcctcgttt ctggctgggg    360
tctgctggcg aacggcagaa tgcctaccgt gctgcagtgc gtgaacgtgt cggtggtgtc    420
tgaggaggtc tgcagtaagc tctatgaccc gctgtaccac cccagcatgt tctgcgccgg    480
cggagggcaa gaccagaagg actcctgcaa cggtgactct gggggcccc tgatctgcaa    540 cgggtacttg cagggccttg tgtctttcgg aaaagcccg tgtggccaag ttggcgtgcc    600
aggtgtctac accaacctct gcaaattcac tgagtggata gagaaaaccg tccaggccag    660
ttaactctgg ggactgggaa cccatgaaat tgacccccaa atacatcctg cggaaggaat    720
tcaggaatat ctgttcccag cccctcctcc ctcaggccca ggagtccagg cccccagccc    780
ctcctccctc aaaccaaggg tacagatccc cagcccctcc tccctcagac caggagtcc    840 agacccccca gccctcctc cctcagaccc aggagtccag cccctcctcc ctcagaccca    900
ggagtccaga ccccagcc cctcctccct cagacccagg ggtccaggcc cccaaccct    960 cctccctcag actcagagt ccaagccccc aaccctcct tccccagacc cagaggtcca    1020
ggtcccagcc cctcctccct cagacccagc ggtccaatgc cacctagact ctccctgtac    1080
acagtgcccc cttgtggcac gttgacccaa ccttaccagt tggttttca ttttttgtcc    1140 cttcccta gatccagaaa taaagtctaa gagaagcgca aaaaaaaaaa aaaaaaaaa    1200
```
aaaaaaaaaa aaaaa                                                        1215

<210> SEQ ID NO 327
<211> LENGTH: 220
<212> TYPE: PRT
<213> ORGANISM: Homo sapien

<400> SEQUENCE: 327

Glu Asp Cys Ser Pro His Ser Gln Pro Trp Gln Ala Ala Leu Val Met
1               5                   10                  15

Glu Asn Glu Leu Phe Cys Ser Gly Val Leu Val His Pro Gln Trp Val
            20                  25                  30

Leu Ser Ala Ala His Cys Phe Gln Asn Ser Tyr Thr Ile Gly Leu Gly
        35                  40                  45

Leu His Ser Leu Glu Ala Asp Gln Glu Pro Gly Ser Gln Met Val Glu
    50                  55                  60

Ala Ser Leu Ser Val Arg His Pro Glu Tyr Asn Arg Pro Leu Leu Ala
65                  70                  75                  80

Asn Asp Leu Met Leu Ile Lys Leu Asp Glu Ser Val Ser Glu Ser Asp
                85                  90                  95

Thr Ile Arg Ser Ile Ser Ile Ala Ser Gln Cys Pro Thr Ala Gly Asn
            100                 105                 110

Ser Cys Leu Val Ser Gly Trp Gly Leu Leu Ala Asn Gly Arg Met Pro
        115                 120                 125

Thr Val Leu Gln Cys Val Asn Val Ser Val Val Ser Glu Glu Val Cys
    130                 135                 140

Ser Lys Leu Tyr Asp Pro Leu Tyr His Pro Ser Met Phe Cys Ala Gly
145                 150                 155                 160

Gly Gly Gln Asp Gln Lys Asp Ser Cys Asn Gly Asp Ser Gly Gly Pro
                165                 170                 175

Leu Ile Cys Asn Gly Tyr Leu Gln Gly Leu Val Ser Phe Gly Lys Ala
            180                 185                 190

Pro Cys Gly Gln Val Gly Val Pro Gly Val Tyr Thr Asn Leu Cys Lys
        195                 200                 205

Phe Thr Glu Trp Ile Glu Lys Thr Val Gln Ala Ser
    210                 215                 220

<210> SEQ ID NO 328
<211> LENGTH: 234
<212> TYPE: DNA
<213> ORGANISM: Homo sapien

<400> SEQUENCE: 328
cgctcgtctc tggtagctgc agccaaatca taaacggcga ggactgcagc ccgcactcgc      60
agccctggca ggcggcactg gtcatggaaa acgaattgtt ctgctcgggc gtcctggtgc     120
atccgcagtg ggtgctgtca gccacacact gtttccagaa ctcctacacc atcgggctgg     180
gcctgcacag tcttgaggcc gaccaagagc cagggagcca gatggtggag gcca           234

<210> SEQ ID NO 329
<211> LENGTH: 77
<212> TYPE: PRT
<213> ORGANISM: Homo sapien

<400> SEQUENCE: 329

Leu Val Ser Gly Ser Cys Ser Gln Ile Ile Asn Gly Glu Asp Cys Ser
1               5                   10                  15

Pro His Ser Gln Pro Trp Gln Ala Ala Leu Val Met Glu Asn Glu Leu
            20                  25                  30

Phe Cys Ser Gly Val Leu Val His Pro Gln Trp Val Leu Ser Ala Thr
             35                  40                  45

His Cys Phe Gln Asn Ser Tyr Thr Ile Gly Leu Gly Leu His Ser Leu
         50                  55                  60

Glu Ala Asp Gln Glu Pro Gly Ser Gln Met Val Glu Ala
 65                  70                  75

<210> SEQ ID NO 330
<211> LENGTH: 70
<212> TYPE: DNA
<213> ORGANISM: Homo sapien

<400> SEQUENCE: 330
cccaacacaa tggcccgatc ccatccctga ctccgccctc aggatcgctc gtctctggta    60
gctgcagcca                                                          70

<210> SEQ ID NO 331
<211> LENGTH: 22
<212> TYPE: PRT
<213> ORGANISM: Homo sapien

<400> SEQUENCE: 331

Gln His Asn Gly Pro Ile Pro Ser Leu Thr Pro Pro Ser Gly Ser Leu
 1               5                  10                  15

Val Ser Gly Ser Cys Ser
            20

<210> SEQ ID NO 332
<211> LENGTH: 2507
<212> TYPE: DNA
<213> ORGANISM: Homo sapien

<400> SEQUENCE: 332
tggtgccgct gcagccggca gagatggttg agctcatgtt cccgctgttg ctcctccttc      60
tgcccttcct tctgtatatg gctgcgcccc aaatcaggaa aatgctgtcc agtggggtgt    120
gtacatcaac tgttcagctt cctgggaaag tagttgtggt cacaggagct aatacaggta    180
tcgggaagga gacagccaaa gagctggctc agagaggagc tcgagtatat tagcttgcc     240 gggatgtgga aaaggggaa ttggtggcca agagatccca gaccacgaca gggaaccagc     300
aggtgttggt gcggaaactg gacctgtctg atactaagtc tattcgagct tttgctaagg    360
gcttcttagc tgaggaaaag cacctccacg ttttgatcaa caatgcagga gtgatgatgt    420
gtccgtactc gaagacagca gatggctttg agatgcacat aggagtcaac cacttgggtc    480
acttcctcct aacccatctg ctgctagaga actaaaagga atcagcccca tcaaggatag    540
taaatgtgtc ttccctcgca catcacctgg gaaggatcca cttccataac ctgcagggcg    600
agaaattcta caatgcaggc ctggcctact gtcacagcaa gctagccaac atcctcttca    660
cccaggaact ggcccggaga ctaaaaggct ctggcgttac gacgtattct gtacaccctg    720
gcacagtcca atctgaactg gttcggcact catctttcat gagatggatg tggtggcttt    780 tctcctttt catcaagact cctcagcagg gagcccagac cagcctgcac tgtgccttaa    840
cagaaggtct tgagattcta agtgggaatc atttcagtga ctgtcatgtg gcatgggtct    900
ctgcccaagc tcgtaatgag actatagcaa ggcggctgtg ggacgtcagt tgtgacctgc    960
tgggcctccc aatagactaa caggcagtgc cagttggacc caagagaaga ctgcagcaga   1020

```
ctacacagta cttcttgtca aaatgattct ccttcaaggt tttcaaaacc tttagcacaa    1080
agagagcaaa accttccagc cttgcctgct tggtgtccag ttaaaactca gtgtactgcc    1140
agattcgtct aaatgtctgt catgtccaga tttactttgc ttctgttact gccagagtta    1200
ctagagatat cataatagga taagaagacc ctcatatgac ctgcacagct cattttcctt    1260
ctgaaagaaa ctactaccta ggagaatcta agctatagca gggatgattt atgcaaattt    1320
gaactagctt ctttgttcac aattcagttc ctcccaacca accagtcttc acttcaagag    1380
ggccacactg caacctcagc ttaacatgaa taacaaagac tggctcagga gcagggcttg    1440
cccaggcatg gtggatcacc ggaggtcagt agttcaagac cagcctggcc aacatggtga    1500
aaccccacct ctactaaaaa ttgtgtatat ctttgtgtgt cttcctgttt atgtgtgcca    1560
agggagtatt ttcacaaagt tcaaacagc cacaataatc agagatggag caaccagtg     1620
ccatccagtc tttatgcaaa tgaaatgctg caaagggaag cagattctgt atatgttggt    1680
aactacccac caagagcaca tgggtagcag ggaagaagta aaaaagaga aggagaatac     1740
tggaagataa tgcacaaaat gaagggacta gttaaggatt aactagccct ttaaggatta    1800
actagttaag gattaatagc aaaagayatt aaatatgcta acatagctat ggaggaattg    1860
agggcaagca cccaggactg atgaggtctt aacaaaaacc agtgtggcaa aaaaaaaaa    1920
aaaaaaaaa aaaatccta aaacaaaca acaaaaaa acaattcttc attcagaaaa         1980
attatcttag ggactgatat tggtaattat ggtcaattta ataatatttt ggggcatttc    2040
cttacattgt cttgacaaga ttaaaatgtc tgtgccaaaa ttttgtattt tatttggaga    2100
cttcttatca aaagtaatgc tgccaaagga agtctaagga attagtagtg ttcccatcac    2160
ttgtttggag tgtgctattc taaagatttt tgatttcctg gaatgacaat tatattttaa    2220
cttttggtggg ggaaagagtt ataggaccac agtcttcact tctgatactt gtaaattaat   2280
cttttattgc acttgtttg accattaagc tatatgttta gaaatggtca ttttacggaa     2340
aaattagaaa aattctgata atagtgcaga ataaatgaat taatgttta cttaatttat    2400
attgaactgt caatgacaaa taaaaattct ttttgattat tttttgtttt catttaccag    2460
aataaaaacg taagaattaa agtttgatt acaaaaaaaa aaaaaaa                   2507
```

<210> SEQ ID NO 333
<211> LENGTH: 3030
<212> TYPE: DNA
<213> ORGANISM: Homo sapien

<400> SEQUENCE: 333

```
gcaggcgact tgcgagctgg gagcgattta aaacgctttg gattccccg gcctgggtgg      60
ggagagcgag ctgggtgccc cctagattcc ccgccccgc acctcatgag ccgaccctcg    120
gctccatgga gcccggcaat tatgccacct tggatggagc caaggatatc gaaggcttgc    180
tgggagcggg aggggggcgg aatctggtcg cccactcccc tctgaccagc cacccagcgg    240
cgcctacgct gatgcctgct gtcaactatg ccccccttgga tctgccaggc tcggcggagc    300
cgccaaagca atgccaccca tgccctgggg tgccccaggg gacgtcccca gctcccgtgc    360
cttatggtta ctttggaggc gggtactact cctgccgagt gtcccggagc tcgctgaaac    420
cctgtgccca ggcagccacc ctggccgcgt accccgcgga gactcccacg gccggggaag    480
agtacccag ycgccccact gagtttgcct tctatccggg atatccggga acctaccagc    540
ctatggccag ttacctggac gtgtctgtgg tgcagactct gggtgctcct ggagaaccgc    600
```

```
gacatgactc cctgttgcct gtggacagtt accagtcttg ggctctcgct ggtggctgga      660
acagccagat gtgttgccag ggagaacaga acccaccagg tcccttttgg aaggcagcat      720
ttgcagactc cagcgggcag caccctcctg acgcctgcgc ctttcgtcgc ggccgcaaga      780
aacgcattcc gtacagcaag gggcagttgc gggagctgga gcgggagtat gcggctaaca      840
agttcatcac caaggacaag aggcgcaaga tctcggcagc caccagcctc tcggagcgcc      900
agattaccat ctggtttcag aaccgccggg tcaaagagaa gaaggttctc gccaaggtga      960
agaacagcgc taccccttaa gagatctcct tgcctgggtg ggaggagcga agtgggggt     1020 gtcctgggga gaccaggaac ctgccaagcc caggctgggg ccaaggactc tgctgagagg     1080
cccctagaga caacacccctt cccaggccac tggctgctgg actgttcctc aggagcggcc     1140
tgggtaccca gtatgtgcag ggagacggaa ccccatgtga cagcccactc caccagggtt     1200
cccaaagaac ctggcccagt cataatcatt catcctgaca gtggcaataa tcacgataac     1260
cagtactagc tgccatgatc gttagcctca tattttctat ctagagctct gtagagcact     1320
ttagaaaccg ctttcatgaa ttgagctaat tatgaataaa tttggaaggc gatccctttg     1380
cagggaagct ttctctcaga ccccccttcca ttacacctct caccctggta acagcaggaa     1440
gactgaggag aggggaacgg gcagattcgt tgtgtggctg tgatgtccgt ttagcatttt     1500
tctcagctga cagctgggta ggtggacaat tgtagaggct gtctcttcct ccctccttgt     1560 ccacccata gggtgtaccc actggtcttg gaagcaccca tccttaatac gatgattttt     1620
ctgtcgtgtg aaaatgaagc cagcaggctg cccctagtca gtccttcctt ccagagaaaa     1680
agagatttga gaaagtgcct gggtaattca ccattaattt cctcccccaa actctctgag     1740
tcttccctta atatttctgg tggttctgac caaagcaggt catggttttgt tgagcatttg     1800 ggatcccagt gaagtagatg tttgtagcct tgcatactta gcccttccca ggcacaaacg     1860
gagtggcaga gtggtgccaa ccctgttttc ccagtccacg tagacagatt cacagtgcgg     1920
aattctggaa gctggagaca gacgggctct ttgcagagcc gggactctga gagggacatg     1980
agggcctctg cctctgtgtt cattctctga tgtcctgtac ctgggctcag tgcccggtgg     2040
gactcatctc ctggccgcgc agcaaagcca gcgggttcgt gctggtcctt cctgcacctt     2100
aggctggggg tggggggcct gccggcgcat tctccacgat tgagcgcaca ggcctgaagt     2160
ctggacaacc cgcagaaccg aagctccgag cagcgggtcg gtggcgagta gtgggtcgg     2220 tggcgagcag ttggtggtgg gccgcggccg ccactacctc gaggacattt ccctcccgga     2280
gccagctctc ctagaaaccc cgcggcggcc gccgcagcca agtgtttatg gcccgcggtc     2340
gggtgggatc ctagccctgt ctcctctcct gggaaggagt gagggtggga cgtgacttag     2400
acacctacaa atctatttac caaagaggag cccgggactg agggaaaagg ccaaagagtg     2460
tgagtgcatg cggactgggg gttcagggga agaggacgag gaggaggaag atgaggtcga     2520
tttcctgatt taaaaaatcg tccaagcccc gtggtccagc ttaaggtcct cggttacatg     2580
cgccgctcag agcaggtcac tttctgcctt ccacgtcctc cttcaaggaa gccccatgtg     2640
ggtagctttc aatatcgcag gttcttactc ctctgcctct ataagctcaa acccaccaac     2700
gatcgggcaa gtaaaccccc tccctcgccg acttcggaac tggcgagagt tcagcgcaga     2760
tgggcctgtg gggaggggc aagatagatg aggggagcg gcatggtgcg gggtgacccc     2820
ttggagagag gaaaaaggcc acaagagggg ctgccaccgc cactaacgga gatggccctg     2880
gtagagacct ttgggggtct ggaacctctg gactccccat gctctaactc ccacactctg     2940
ctatcagaaa cttaaacttg aggattttct ctgttttca ctcgcaataa aytcagagca     3000
```

```
                                                                                  -continued aacaaaaaaa aaaaaaaaaa aaaactcgag                                                        3030

<210> SEQ ID NO 334
<211> LENGTH: 2417
<212> TYPE: DNA
<213> ORGANISM: Homo sapien

<400> SEQUENCE: 334
ggcggccgct ctagagctag tgggatcccc cgggctgcac gaattcggca cgagtgagtt        60
ggagttttac ctgtattgtt ttaatttcaa caagcctgag gactagccac aaatgtaccc       120
agtttacaaa tgaggaaaca ggtgcaaaaa ggttgttacc tgtcaaaggt cgtatgtggc       180
agagccaaga tttgagccca gttatgtctg atgaacttag cctatgctct ttaaacttct       240
gaatgctgac cattgaggat atctaaactt agatcaattg cattttccct ccaagactat       300
ttacttatca atacaataat accaccttta ccaatctatt gttttgatac gagactcaaa       360
tatgccagat atatgtaaaa gcaacctaca agctctctaa tcatgctcac ctaaaagatt       420
cccgggatct aataggctca agaaacttc ttctagaaat ataaaagaga aaattggatt        480
atgcaaaaat tcattattaa ttttttttcat ccatccttta attcagcaaa catttatctg      540
ttgttgactt tatgcagtat ggccttttaa ggattggggg acaggtgaag aacggggtgc       600
cagaatgcat cctcctacta atgaggtcag tacacatttg cattttaaaa tgccctgtcc       660
agctgggcat ggtggatcat gcctgtaatc tcaacattgg aaggccaagg caggaggatt       720
gcttcagccc aggagttcaa gaccagcctg gcaacatag aaagacccca tctctcaatc        780
aatcaatcaa tgccctgtct ttgaaaataa aactctttaa gaaaggttta atgggcaggg       840
tgtggtagct catgcctata atacagcact ttgggaggct gaggcaggag gatcacttta       900
gcccagaagt tcaagaccag cctgggcaac aagtgacacc tcatctcaat tttttaataa       960
aatgaataca tacataagga aagataaaaa gaaaagttta atgaaagaat acagtataaa      1020
acaaatctct tggacctaaa agtattttttg ttcaagccaa atattgtgaa tcacctctct     1080
gtgttgagga tacagaatat ctaagcccag gaaactgagc agaaagttca tgtactaact      1140
aatcaacccg aggcaaggca aaaatgagac taactaatca atccgaggca aggggcaaat      1200
tagacggaac ctgactctgg tctattaagc gacaactttc cctctgttgt atttttcttt      1260
tattcaatgt aaaaggataa aaactctcta aaactaaaaa caatgtttgt caggagttac      1320
aaaccatgac caactaatta tggggaatca taaaatatga ctgtatgaga tcttgatggt      1380
ttacaaagtg tacccactgt taatcacttt aaacattaat gaacttaaaa atgaatttac      1440
ggagattgga atgtttcttt cctgttgtat tagttggctc aggctgccat aacaaaatac      1500
cacagactgg gaggcttaag taacagaaat tcatttctca cagttctggg ggctggaagt      1560
ccacgatcaa ggtgcaggaa aggcaggctt cattctgagg cccctctctt ggctcacatg      1620
tggccaccct cccactgcgt gctcacatga cctctttgtg ctcctggaaa gagggtgtgg      1680
gggacagagg gaaagagaag gagagggaac tctctggtgt ctcgtctttc aaggacccta    1740
acctgggcca ctttggccca ggcactgtgg ggtgggggt tgtggctgct ctgctctgag      1800
tggccaagat aaagcaacag aaaaatgtcc aaagctgtgc agcaaagaca agccaccgaa      1860
cagggatctg ctcatcagtg tggggacctc caagtcggcc accctggagg caagccccca      1920
cagagcccat gcaaggtggc agcagcagaa gaagggaatt gtccctgtcc ttggcacatt      1980
cctcaccgac ctggtgatgc tggacactgc gatgaatggt aatgtggatg agaatatgat      2040
```

-continued

```
ggactcccag aaaaggagac ccagctgctc aggtggctgc aaatcattac agccttcatc    2100
ctggggagga actgggggcc tggttctggg tcagagagca gcccagtgag ggtgagagct    2160
acagcctgtc ctgccagctg gatcccagt cccggtcaac cagtaatcaa ggctgagcag    2220
atcaggcttc ccggagctgg tcttgggaag ccagccctgg ggtgagttgg ctcctgctgt    2280
ggtactgaga caatattgtc ataaattcaa tgcgcccttg tatccctttt tctttttat    2340 ctgtctacat ctataatcac tatgcatact agtctttgtt agtgtttcta ttcmacttaa    2400
tagagatatg ttatact                                                   2417
```

<210> SEQ ID NO 335
<211> LENGTH: 2984
<212> TYPE: DNA
<213> ORGANISM: Homo sapien

<400> SEQUENCE: 335

```
atccctcctt ccccactctc ctttccagaa ggcacttggg gtcttatctg ttggactctg      60
aaaacacttc aggcgccctt ccaaggcttc cccaaacccc taagcagccg cagaagcgct     120
cccgagctgc cttctcccac actcaggtga tcgagttgga gaggaagttc agccatcaga    180
agtacctgtc ggcccctgaa cgggcccacc tggccaagaa cctcaagctc acggagaccc    240
aagtgaagat atggttccag aacagacgct ataagactaa gcgaaagcag ctctcctcgg    300
agctggagag cttggagaag cactcctctt tgccggccct gaaagaggag gccttctccc    360
gggcctccct ggtctccgtg tataacagct atccttacta cccatacctg tactgcgtgg    420
gcagctggag cccagctttt tggtaatgcc agctcaggtg acaaccatta tgatcaaaaa    480
ctgccttccc cagggtgtct ctatgaaaag cacaaggggc caaggtcagg gagcaagagg    540
tgtgcacacc aaagctattg agatttgcg tggaaatctc asattcttca ctggtgagac    600
aatgaaacaa cagagacagt gaaagtttta atacctaagt cattccccca gtgcatactg    660
taggtcattt ttttgcttc tggctacctg tttgaagggg agagagggaa aatcaagtgg    720
tattttccag cactttgtat gattttggat gagctgtaca cccaaggatt ctgttctgca    780
actccatcct cctgtgtcac tgaatatcaa ctctgaaaga gcaaacctaa caggagaaag    840
gacaaccagg atgaggatgt caccaactga attaaactta agtccagaag cctcctgttg    900
gccttggaat atggccaagg ctctctctgt ccctgtaaaa gagagggca aatagagagt    960 ctccaagaga acgccctcat gctcagcaca tatttgcatg ggaggggag atgggtggga    1020 ggagatgaaa atatcagctt ttcttattcc tttttattcc ttttaaaatg gtatgccaac    1080
ttaagtattt acagggtggc ccaaatagaa caagatgcac tcgctgtgat tttaagacaa    1140
gctgtataaa cagaactcca ctgcaagagg gggggccggg ccaggagaat ctccgcttgt    1200
ccaagacagg ggcctaagga gggtctccac actgctgcta ggggctgttg catttttta    1260 ttagtagaaa gtggaaaggc ctcttctcaa cttttttccc ttgggctgga gaatttagaa    1320
tcagaagttt cctggagttt tcaggctatc atatatactg tatcctgaaa ggcaacataa    1380
ttcttccttc cctccttta aaattttgtg ttccttttg cagcaattac tcactaaagg    1440
gcttcatttt agtccagatt tttagtctgg ctgcacctaa cttatgcctc gcttatttag    1500
cccgagatct ggtctttttt tttttttttt tttttccgtc tccccaaagc tttatctgtc    1560 ttgactttt aaaaaagttt gggggcagat tctgaattgg ctaaaagaca tgcattttta    1620
aaactagcaa ctcttatttc tttcctttaa aaatacatag cattaaatcc caaatcctat    1680
ttaaagacct gacagcttga gaaggtcact actgcattta taggaccttc tggtggttct    1740
```

-continued

```
gctgttacgt ttgaagtctg acaatccttg agaatctttg catgcagagg aggtaagagg    1800
tattggattt tcacagagga agaacacagc gcagaatgaa gggccaggct tactgagctg    1860
tccagtggag ggctcatggg tgggacatgg aaaagaaggc agcctaggcc ctggggagcc    1920
cagtccactg agcaagcaag ggactgagtg agccttttgc aggaaaaggc taagaaaaag    1980
gaaaaccatt ctaaaacaca acaagaaact gtccaaatgc tttgggaact gtgtttattg    2040
cctataatgg gtccccaaaa tgggtaacct agacttcaga gagaatgagc agagagcaaa    2100
ggagaaatct ggctgtcctt ccattttcat tctgttatct caggtgagct ggtagagggg    2160
agacattaga aaaaaatgaa acaacaaaac aattactaat gaggtacgct gaggcctggg    2220
agtctcttga ctccactact taattccgtt tagtgagaaa cctttcaatt ttcttttatt    2280
agaagggcca gcttactgtt ggtggcaaaa ttgccaacat aagttaatag aaagttggcc    2340
aatttcaccc catttctgt ggtttgggct ccacattgca atgttcaatg ccacgtgctg    2400
ctgacaccga ccggagtact agccagcaca aaaggcaggg tagcctgaat tgctttctgc    2460
tctttacatt tcttttaaaa taagcattta gtgctcagtc cctactgagt actctttctc    2520
tcccctcctc tgaatttaat tctttcaact tgcaatttgc aaggattaca catttcactg    2580
tgatgtatat tgtgttgcaa aaaaaaaaaa aagtgtcttt gtttaaaatt acttggtttg    2640
tgaatccatc ttgcttttc cccattggaa ctagtcatta acccatctct gaactggtag    2700
aaaaacatct gaagagctag tctatcagca tctgacaggt gaattggatg ttctcagaa    2760 ccatttcacc cagacagcct gtttctatcc tgtttaataa attagtttgg gttctctaca    2820
tgcataacaa accctgctcc aatctgtcac ataaaagtct gtgacttgaa gtttagtcag    2880
cacccccacc aaactttatt tttctatgtg tttttttgcaa catatgagtg ttttgaaaat    2940
aaagtaccca tgtctttatt agaaaaaaaa aaaaaaaaaa aaaa                     2984
```

<210> SEQ ID NO 336
<211> LENGTH: 147
<212> TYPE: PRT
<213> ORGANISM: Homo sapien

<400> SEQUENCE: 336

```
Pro Ser Phe Pro Thr Leu Leu Ser Arg Arg His Leu Gly Ser Tyr Leu
 1               5                  10                  15

Leu Asp Ser Glu Asn Thr Ser Gly Ala Leu Pro Arg Leu Pro Gln Thr
                20                  25                  30

Pro Lys Gln Pro Gln Lys Arg Ser Arg Ala Ala Phe Ser His Thr Gln
            35                  40                  45

Val Ile Glu Leu Glu Arg Lys Phe Ser His Gln Lys Tyr Leu Ser Ala
        50                  55                  60

Pro Glu Arg Ala His Leu Ala Lys Asn Leu Lys Leu Thr Glu Thr Gln
 65                  70                  75                  80

Val Lys Ile Trp Phe Gln Asn Arg Arg Tyr Lys Thr Lys Arg Lys Gln
                85                  90                  95

Leu Ser Ser Glu Leu Gly Asp Leu Glu Lys His Ser Ser Leu Pro Ala
               100                 105                 110

Leu Lys Glu Glu Ala Phe Ser Arg Ala Ser Leu Val Ser Val Tyr Asn
            115                 120                 125

Ser Tyr Pro Tyr Pro Tyr Leu Tyr Cys Val Gly Ser Trp Ser Pro
        130                 135                 140

Ala Phe Trp
```

```
145

<210> SEQ ID NO 337
<211> LENGTH: 9
<212> TYPE: PRT
<213> ORGANISM: Homo sapien

<400> SEQUENCE: 337

Ala Leu Thr Gly Phe Thr Phe Ser Ala
 1               5

<210> SEQ ID NO 338
<211> LENGTH: 9
<212> TYPE: PRT
<213> ORGANISM: Homo sapien

<400> SEQUENCE: 338

Leu Leu Ala Asn Asp Leu Met Leu Ile
 1               5
```